United States Patent
Miller et al.

(10) Patent No.: US 9,587,266 B2
(45) Date of Patent: Mar. 7, 2017

(54) MUTANT LUCIFERASES

(75) Inventors: Stephen C. Miller, Cambridge, MA (US); David Mofford, Marlborough, MA (US); Katryn Harwood, North Bethesda, MD (US)

(73) Assignee: University of Massachusetts, Boston, MA (US)

( * ) Notice: Subject to any disclaimer, the term of this patent is extended or adjusted under 35 U.S.C. 154(b) by 237 days.

(21) Appl. No.: 13/984,506

(22) PCT Filed: Feb. 9, 2012

(86) PCT No.: PCT/US2012/024526
§ 371 (c)(1),
(2), (4) Date: Mar. 24, 2014

(87) PCT Pub. No.: WO2012/109470
PCT Pub. Date: Aug. 16, 2012

(65) Prior Publication Data
US 2014/0201855 A1 Jul. 17, 2014

Related U.S. Application Data

(60) Provisional application No. 61/441,136, filed on Feb. 9, 2011.

(51) Int. Cl.
*C12Q 1/66* (2006.01)
*C12N 9/02* (2006.01)

(52) U.S. Cl.
CPC .............. *C12Q 1/66* (2013.01); *C12N 9/0069* (2013.01); *C12Y 113/12007* (2013.01); *A01K 2267/0393* (2013.01); *C07K 2319/00* (2013.01); *C07K 2319/02* (2013.01); *C07K 2319/23* (2013.01); *C07K 2319/30* (2013.01); *C07K 2319/31* (2013.01); *C07K 2319/50* (2013.01)

(58) Field of Classification Search
CPC ................................................ C07K 2319/00
See application file for complete search history.

(56) References Cited

FOREIGN PATENT DOCUMENTS

WO WO 2007/019634 * 2/2007

OTHER PUBLICATIONS

GenBank Acc#ACH87777 from Day et al, Mol. Phylogenet. Evol. 50 (1), 93-101 (2009). Alignment with SEQ ID No. 5.*
UniProt_201602 database accession No. Q2ACC9_LUCCR from Oba et al, Identification of paralogous genes of firefly luciferase in the Japanese firefly, Luciola cruciata Gene 368:53-60(2006). Alignment with SEQ ID No. 5 with X218 and X342.*
Branchini et al, The Role of Active Site Residue Arginine 218 in Firefly Luciferase Bioluminescence. Biochemistry 2001, 40, 2410-2418.*
Branchini et al, A Mutagenesis Study of the Putative Luciferin Binding Site Residues of Firefly Luciferase. Biochemistry 2003, 42, 10429-10436.*
International Preliminary Report on Patentability for International Application No. PCT/US2012/024526 dated Aug. 13, 2013 (7 pages).
G. R. Reddy et al., "Robust Light Emission from Cyclic Alkylaminoluciferin Substrates for Firefly Luciferase," Journal of American Chemical Society, vol. 132, No. 39, pp. 13586-13587 (Oct. 6, 2010).
Notification of Transmittal of the International Search Report and the Written Opinion of the International Searching Authority, or the Declaration for International Application No. PCT/US2012/024526, dated Sep. 19, 2012, 12 pages.
Adams Jr., S. T. et al., "Firefly Luciferase Mutants Allow Substrate-Selective Bioluminescence Imaging in the Mouse Brain", Angew. Chem. Int. Ed. 2016, vol. 55:4943-4946.
Branchini, B. R. et al, "A mutagenesis study of the putative luciferin binding site residues of firefly luciferase", Biochemistry 2003, vol. 42:10429-10436.
Fujii, H, et al., "Increase in bioluminescence intensity of firefly luciferase using genetic modification", Analytical Biochemistry 2007, vol. 366:131-136.
Woodroofe, C. C. et al., "N-alkylated 6' aminoluciferins are bioluminescent substrates for Ultra-Glo and QuantiLum luciferase: new potential scaffolds for bioluminescent assays", Biochemistry 2008, vol. 47:10383-10393.

* cited by examiner

*Primary Examiner* — Sheridan Swope
(74) *Attorney, Agent, or Firm* — Fish & Richardson P.C.

(57) ABSTRACT

Described are mutant luciferases, nucleic acids that encode them, cells and animals expressing them, methods of use thereof, and kits.

16 Claims, 39 Drawing Sheets

```
1    MENMENDENIVVGPKPFYPIEEGSAGTQLRKYMERYAKL-GAIAFTNAVTGVDYSYAEYLEKSCCLGKALQNYGLVVDGR      79
1    MENMENDENIVYGPEPFYPIEEGSAGAQLRKYMDRYAKL-GAIAFTNALFGVDYTYAEYLEKSCCLGEALKNYGLVVDGR      79
1    MR-MEKEENVVYGPLPFYPIEEEPHPLADGTAGEQMFYALSRVADISGCIALTNAHTKENVLYEEFLKLSCRLAESFKKYGLKQNDT  78
1    ME----DKNILYGPEEPHPLADGTAGEQMFYALSRVADISGCIALTNAHTKENVLYEEFLKLSCRLAESFKKYGLKQNDT    76
1    ---MEDAKNIKKGPAPFYPLEDGTAGEQLHRAMKRYALVPGTIAFTDAHIEVNITYAEYYEMSVRLAEAMKRYGLNTNHR     77

80   IALCSENCEEFFIPVIAGLFTGVGVAPTNEIYTLRELVHSLGISKPTIVFSSKKGLDKVITVQKTVTTIKTIVILDSKVD      159
80   IALCSENCEEFFIPVLAGLFICVGVAPTNEIYTLRELVHSLGISKPTIVFSSKKGLDKVITVQKTVTAIKTIVILDSKVD      159
79   IALCSENCEEFFIPVLAGLYLGIIAAPVSDKYIERELIESLGIVKRFIIFCSKNTFQKVLNVKSKLKYVETHILDLNED      158
77   IAVCSENGLQFFLPLIASLYLGIIAAPVSDKYIERELIESLGIVKRFIIFCSKNTFQKVLNVKSKLKYVETHILDLNED      156
78   IVVCSENSLQFFMPVLGALFTGVAVAPANDIYNERELLNSMNISQPTVVFVSKKGLQKILNVQKKLPIIQKIIMDSKID      157

160  YRGYQCLDTFIKRNTPGFQASSFKTVEV-DRKEQVALIMNSSGSTGLPKGVQLTHENVTRFSHARDPIYGNJVSPGTA      238
160  YRGYQSMDNFIKKNTPQGFKGSSFKTVEV-NRKEQVALIMNSSGSTGLPKGVQLTHENAVIRFSHARDPIYGNJVSPGTA      238
159  FGGHDCMETFIKKHVELGFQPSSFVPIDVANRKQHVALIMNSSGSTGLPKGVRITHEGAVTRFSHAKDPIYGNJVSPGTA      238
157  LGGYQCLNNFISQNSDINLDVKKFKPNSF-NRDDQVALVMFSSGTGVSKGVMLTHKNIVARFSHCKDPTFGNAINPTTA      235
158  YQGFQSMYTFVTSHLPGFNEYQFVPESF-DRKTIALIMNSSGSTGLPKGVALPHRTACVRFSHARDPLFGNDIIPDTA      236

239  VILTVVPFHHGFGMFTTLGYLICGFRVVMLITKFDEETFLKTLQDYKCTSVIILVPTLFAILNKSELLNKYDLSNLVFEIASGG     318
239  ILTVVPFHHGFGMFTTLGYLTCGFRIVMLTKFDEETFLKTLQDYKCSSVIILVPTLFAILNRSELLDKYDLSNLVEIASGG      318
239  ILTVVPFHHGFGMFTTLGYFACGYRVVMLTKFDEELFIRTLQDYKCTSVIILVPTLFAILNKSELIDKFDLSNLFEIASGG      318
236  ILFVIPFHHGFCMITTLGYFTCGFRVALMTFEEKLFLQSLQDYKVESTLLVPTLMAFFPKSALVEKYDLSHIKEIASGG      315
237  ILSVVPFHHGFGMFTTLGYLICGFRVVLMIRFEEELFLRSLQDYKIQSALLVPTLFSFAKSTLIDKYDLSNLHEIASGG      316

319  APLSKEVGEAVARRFNLPGVRQGYGLTETTSAIITPEGDDKPGASGKVVPLFKAKVIDLDTKKSLGPNRRGEVCVKGPM      398
319  APLSKEIGEAVARRFNLPGVRQGYGLTETTSAIITPEGDDKPGASGKVVPLFKAKVIDLETKKTLGPNRRGEVCVKGPM      398
319  APLAKEVGEAVARRFNLPGVRQGYGLTETTSAFIITPEGDDKPGASGKVVPLFKVKVIDLDTKKTLGVNRRGEICVKGPS      398
316  APLSKEIGEMVKKREKLNFVRQGYGLTETTSAVLITPDTDVRPGSTGKIVPFHAVKVVDPTTGKILGPNETGELYFKGFM      395
317  APLSKEVGEAVAKRFHLPGHRQGYGLTETTSALLITPEGDDKPGVGKVVFFEAKVVDLDTGKTLGVNQRGELCVRGPM      396

399  LMKGYVNNPEATKELIDEEGWLHTGDIGYDEEKHFFTIVDRLKSLIKYKGYQVPPAELESVLLQHPSIFDAGVPDPV      478
399  LMKGYVNNPEATREIIDEEGWLHTGDIGYDEEKHFFIVDRLKSLIKYKGYQVPPAELESVLLQHPNIFDAGVAGVFDPI      478
399  LMLGYSNNPEATRETIDEEGMLHTGDIGYDEDEHFFIVDRLKSLIKYGYQVPPAELESVLLQHPVIFDAGVAGVPDPD      478
396  IMKSYYNNEEATKAIINKDGWLRSGDIAYYNDGHFYIVDRLKSLIKYKGYSVSTAKWLRGGVKFLDEIPKGSTGKIDRKVLRQMFEKHK----SKL  475
397  IMSGYVNNPEATNALIDKDGWLHSGDIAYWDEDEHFFIVDRLKSLIKYKGYQVAPAELESILLQHPNIFDAGVAGLFDDO      477

479  AGELPGAVVVLESCKNMTEKEVMDYVASQVSNAKRLRGGVRFVDEVPKGLTGKIDCRAIREILKK----PVAKM        548  SEQ ID NO:1
479  AGELPGAVVVLEKGKSMTEKEVMDYVASQVSNAKRLGGVRFVDEVPKGLTGKIDGKAIREILKK----PVAKM        548  SEQ ID NO:2
479  AGELPGAVVVMEKGKTMTEKEIVDYVNSQVVNHKRLRGGVRFVDEVPKGLTGKIDAKVIREILKK----PQAKM        548  SEQ ID NO:3
476  AGELPAAGVVVCTGKYLNEQIVQNFVSSQVSTAKWLRGGVKFLDEIPKGSTGKIDRKVLRQMFEKHK----SKL        545  SEQ ID NO:4
477  AGELPAAVVVLEHGKTMTEKEIVDYVASQVTTAKKLRGGVTPKGLTGKLDARKIREILIKAKKGGKSKL        550  SEQ ID NO:5
```

MUTANT LUCIFERASES

CLAIM OF PRIORITY

This application is a National Stage application under 35 U.S.C. 371 of International Application No. PCT/US2012/024526, having an International Filing Date of Feb. 9, 2012, which claims the benefit of U.S. Provisional Patent Application Ser. No. 61/441,136, filed on Feb. 9, 2011. The contents of the above applications are hereby incorporated by reference in their entirety.

FEDERALLY FUNDED RESEARCH OR DEVELOPMENT

This invention was made with government support under Grant No. R21 CA127196-02 awarded by the National Institutes of Health. The government has certain rights in the invention.

TECHNICAL FIELD

This invention relates to mutant luciferases, nucleic acids that encode them, cells and animals expressing them, and methods of use thereof.

BACKGROUND

Firefly luciferase exhibits burst kinetics: upon contact with the substrate, an initial burst of light is followed by a significant drop in the rate of light output.

There has been great disagreement as to the molecular basis for the observation that luciferase light output decreases (fairly rapidly) over time, giving rise to "burst kinetics". Three explanations have been proposed: 1) product inhibition by oxyluciferin, 2) inhibition by the off-pathway formation of dehydroluciferyl-AMP, and 3) free-radical damage of the luciferase by the light-generating reaction itself. These explanations are not mutually exclusive.

Oxyluciferin itself has an affinity for luciferase that is similar to D-luciferin, while the binding affinity of AMP is significantly lower. For these products to have a substantial effect on the light output of luciferase by virtue of product inhibition, a cooperative effect on dissociation, or the trapping of the luciferase in an inactive oxyluciferin-ATP-bound state are the most likely possible scenarios.

Another potential source of product inhibition is from the "dark" side product, L-AMP. This compound can be produced from LH2-AMP by oxidation to give the dehydroluciferin rather than formation of the excited state oxyluciferin. No light is produced, and the phosphate ester linkage is not cleaved. This "bidentate" product therefore has significantly higher binding affinity than D-luciferin, oxyluciferin, or AMP alone.

When firefly luciferase and D-luciferin are treated with coenzyme A (CoASH), some rescue of light output is obtained. This has been interpreted as arising from the conversion of L-AMP into L-CoA and AMP, which have lower binding affinity and can therefore more readily diffuse away from the binding pocket.

Light emission from firefly luciferase is fundamentally limited by its access to D-luciferin and the inherent photophysical properties of the D-luciferin substrate (Reddy et al., J. Am. Chem. Soc 132, 13586-13587, 2010). Replacement of the 6'-hydroxyl group of D-luciferin with a 6'-amino group results in red-shifted light emission (White et al., J. Am. Chem. Soc. 88, 2015-2019, 1966) and higher affinity for luciferase, but lower maximal light emission and lower cell-permeability (Shinde et al., Biochemistry 45, 11103-12, 2006). Although D-luciferin is the superior substrate for maximal light emission under most conditions, the unique chemistry of 6'-aminoluciferin has expanded the scope of luciferase applications. For example, the liberation of 6'-aminoluciferin from "dark" pro-luciferin protease substrates has been exploited to allow the coupled bioluminescent detection of protease activity, both in vitro (Monsees et al., Anal. Biochem. 221, 329-34, 1994; Moravec et al., Anal. Biochem 387, 294-302, 2009) and in vivo (Shah et al., Mol Ther 11, 926-931, 2005; Dragulescu-Andrasi et al., Bioconjug Chem 20, 1660-1666, 2009; Hickson et al., Cell Death Differ 17, 1003-1010, 2010; Scabini et al., Apoptosis 16, 198-207, 2011).

6'-alkylaminoluciferins can also be substrates for luciferase (Woodroofe et al., Biochemistry 47, 10383-1039, 2008; Reddy et al., J. Am. Chem. Soc 132, 13586-13587, 2010; Takakura et al., Chem Asian J 5, 2053-2061, 2010). These substrates generally have even higher affinity for luciferase than 6'-aminoluciferin, and emit light at even longer wavelengths. Many modifications are tolerated, including long-chain 6'-alkylaminoluciferins, 5',6'-cyclic alkylaminoluciferins, and even dialkylaminoluciferins. Synthetic modulation of the properties of these molecules thus presents an opportunity to develop new bioluminescent probes and to optimize luciferase light output for different applications. However, with wild-type *Photinus pyralis* firefly luciferase, most of these substrates give a rapid burst of light followed by weak sustained emission (Reddy et al., J. Am. Chem. Soc 132, 13586-13587, 2010).

The detergent-stable proprietary mutant luciferase Ultra-Glo (Promega) is capable of high sustained light emission with aminoluciferin substrates, particularly in combination with the P450-Glo buffer (Woodroofe et al., Biochemistry 47, 10383-1039, 2008; Reddy et al., J. Am. Chem. Soc 132, 13586-13587, 2010). The use of aminoluciferins with this luciferase and buffer therefore has potential for novel in vitro screening applications, such as the coupled detection of enzymatic activity (Fan and Wood, Assay Drug. Dev. Technol. 5, 127-136, 2007). However, Ultra-Glo is a proprietary luciferase reagent that is not available as a genetic construct that can be expressed in cells. Furthermore, the detergent stability of Ultra-Glo and the use of the P450-Glo buffer are important for the light emission behavior. Cellular and in vivo applications such as the detection of gene expression (de Wet et al., Mol Cell Biol 7, 725-737, 1987) and bioluminescent imaging (Prescher and Contag, Curr. Op. Chem. Biol. 14, 80-89, 2010) necessitate a genetically-encodable luciferase that is capable of efficient utilization of aminoluciferins under physiological buffer conditions.

To monitor gene expression in mammalian cells or perform bioluminescence imaging in whole organisms, a genetically-encoded luciferase capable of efficient light emission with aminoluciferins is necessary.

SUMMARY

The wild-type luciferase suffers product inhibition with all aminoluciferins that limits their use in vivo and in vitro (see, e.g., Reddy et al., J. Am. Chem. Soc. 132, 13586 (2010)). The luciferase mutants disclosed here allow efficient light emission from aminoluciferins, in vitro with the purified proteins, in mammalian cell lysates, and in live mammalian cells. The mutant luciferases in combination with synthetic aminoluciferin substrates can give higher light output in live mammalian cells than D-luciferin over a wide concentration range. Moreover, discrimination was observed between substrates with different mutants, thereby allowing the construction of orthogonal luciferases.

Thus, in a first aspect, the invention provides mutant luciferases with one or more of the following mutations: F247V; F247S; F247R; F247Q; F247T; T251N; T251Q; T251V; T251I; T251S; L286T; L286Y; L286S; L286M; S347C; S347T; S347H; Q338W; R218V; R218Y; R218S; R218T; A313F; A313N; A313L; A313G; L286A; and/or A348G (numbering relative to SEQ ID NO:5).

In an additional aspect, the invention provides mutant luciferases with two or more of the following mutations: L342A; F247A; F247L; F247V; F247S; F247R; F247Q; F247T T251N; T251Q; T251V; T251I; T251S; L286T; L286Y; L286S; L286M; S347C; S347T; S347H; Q338W; R218K; R218V; R218Y; R218S; R218T; A313F; A313N; A313L; A313G; L286A; S347A; A348G; E311A; I351A; and/or R337A (numbering relative to SEQ ID NO:5).

In a further aspect, the invention provides mutant luciferases with one of the following sets of mutations: S347A+L286M; S347A+T251 S; S347A+F247V; S347A+ F247S; S347A+F247L; F247L+L286M; F247S+T251S; T251S+L286M; F247L+T251S; A313G+F247L; R218K+ T251S; R218K+S347A; R218K+T251M; R218K+L286M; R218K+T251E; R218K+T251Q; R218K+F247L; R218K+ F247Q; R218K+F247T; L286M+T251S; L286M+S347A; R218K+L342A; L286M+L342A; T251S+L286M+S347A; F247L+S347A+T251 S; F247L+S347A+L286M; F247L+ T251S+L286M; R218K+T251S+S347H; R218K+L286M+ S347A; or R218K+L286M+S347A+L342A (numbering relative to SEQ ID NO:5).

In some embodiments, the mutations comprise T251 S and L286M; F247L and L286M; F247L and S347A; L286M and S347A; R218K and L286M; or R218K and L342A (numbering relative to SEQ ID NO:5).

In some embodiments, the mutant luciferase comprises a mutated firefly luciferase (e.g., comprising SEQ ID NO:1 or 5), click beetle luciferase, or railroad worm luciferase.

In further aspects, the invention provides nucleic acids encoding the mutant luciferases described herein, vectors comprising the nucleic acids, and host cells harboring or expressing the nucleic acids. Also provided are transgenic animals, the germ and/or somatic cells of which comprise the nucleic acids described herein, as well as cells from the transgenic animals.

In another aspect, the invention provides kits including a mutant luciferase, nucleic acid, or vector as described herein, and a cognate luciferin substrate, preferably a D-luciferin analog, an aminoluciferin or alkylaminoluciferin substrate. As used herein a "cognate luciferin substrate" is a luciferin substrate that, when combined with a given mutant luciferase as described herein, produces bioluminescence. In some embodiments the substrate is not D-luciferin.

In yet another aspect, the invention provides methods for producing bioluminescence in a sample. The methods include providing a sample comprising a mutant luciferase with one or more of the following mutations: L342A; F247A; F247L; F247V; F247S; F247R; T251N; T251Q; T251V; T251I; T251S; L286T; L286Y; L286S; L286M; S347C; S347T; Q338W; R218K; R218V; R218Y; R218S; R218T; A313F; A313N; A313L; A313G; L286A; S347A; A348G; E311A; I351A; R337A; and contacting the sample with a cognate luciferin substrate, e.g., a D-luciferin analog, aminoluciferin substrate or alkylaminoluciferin substrate, wherein if the mutant comprises R218K, F247A, F247L, S347A, or L342A, the substrate is not D-luciferin (numbering relative to SEQ ID NO:5).

In an additional aspect, the invention provides methods for imaging a sample. The methods include providing a sample comprising a mutant luciferase with one or more of the following mutations: L342A; F247A; F247L; F247V; F247S; F247R; T251N; T251Q; T251V; T251I; T251S; L286T; L286Y; L286S; L286M; S347C; S347T; Q338W; R218K; R218V; R218Y; R218S; R218T; A313F; A313N; A313L; A313G; L286A; S347A; A348G; E311A; I351A; R337A; H245A; (numbering relative to SEQ ID NO:5); contacting the sample with a cognate substrate, e.g., a luciferin analog, aminoluciferin substrate or alkylaminoluciferin substrate, wherein if the mutant luciferase comprises R218K, F247A, F247L, S347A, or L342A, the substrate is not D-luciferin; and detecting luminescence in the sample (i.e., luminescence produced by the reaction of the mutant luciferase and the substrate), thereby imaging the sample.

In some embodiments, the sample comprises a living cell, a living animal, a tissue or organ, or a cell or tissue extract.

In another aspect, the invention provides methods for producing bioluminescence in a sample. The methods include providing a sample comprising a mutant luciferase, and contacting the sample with a cognate substrate, wherein:

(a) the mutant luciferase comprises mutations at F247L, A3136 A313N, R218K, L342A, R218K+F247L, or R218K+T251Q, and the cognate substrate is 6'-aminoluciferin;

(b) the mutant luciferase comprises mutations at S347A, S347T, L286M, T251S, F247S, F247V, R218K, L342A R218K+T251S, R218K+S347A, R218K+T251M, R218K+L286M, R218K+L342A, L286M+S347A, R218K+T251E, R218K+T251S+S347H, R218K+ L286M+S347A, L286M+S347A, L286M+T251S, or L286M+L342A, and the cognate substrate is CycLuc1;

(c) the mutant luciferase comprises mutations at S347A+ L286M and the cognate substrate is CycLuc1, CycLuc3, or MeNHLH2;

(d) the mutant luciferase comprises mutations at A313F, R218Y, R218T, R218S, R218K, L342A, R218K+ F247Q, R218K+F247T, R218K+L342A, L286M+ L342A, or R218K+L286M+S347A and the cognate substrate is CycLuc4;

(e) the mutant luciferase comprises mutations at L286M+ S347A and the cognate substrate is CycLuc1 and/or CycLuc3;

(f) the mutant luciferase comprises mutations at F247L+ S347A and the cognate substrate is MeNHLH2;

(g) the mutant luciferase comprises mutations at R218K, L342A, R218K+L342A, R218K+L286M+S347A, R218K+T251M, or R218K+F247L and the cognate substrate is CycLuc2;

(h) the mutant luciferase comprises mutations at R218K+ L268M+S347A, R218K+L342A, R218K+S347A, R218K+T251S, R218K+L286M+S347A+L342A, or L286M+L342A and the cognate substrate is CycLuc7;

(i) the mutant luciferase comprises mutations at A313F and the cognate substrate is MeNHLH2, CycLuc1, CycLuc2, CycLuc3 and/or CycLuc4;

(j) the mutant luciferase comprises mutations at R128K and the cognate substrate is CycLuc1-8', MeNH-LH2, iBuNH-LH2, (3-hydroxypropyl)NH-LH2, Me2N-LH2 and/or NH2-LH2;

(k) the mutant luciferase comprises mutations at L342A and the cognate substrate is CycLuc1-8', MeNH-LH2, iBuNH-LH2, (3-hydroxypropyl)NH-LH2, Me2N-LH2 and/or NH2LH2; and/or (l) the mutant luciferase comprises mutations at R218K+ L342A and the cognate substrate is CycLuc1-8, MeNH-LH2, iBuNH-LH2, (3-hydroxypropyl)NH-LH2, or Me2N-LH2.

In some embodiments, the methods further include detecting bioluminescence, i.e., bioluminescence produced by the reaction of the mutant luciferase and the substrate, in the sample. In some embodiments, the methods further include obtaining an image of the bioluminescence in the sample.

In some embodiments of the methods described herein, the mutant luciferase comprises a mutated firefly luciferase, click beetle luciferase, glow worm luciferase, or railroad worm luciferase. In some embodiments, the firefly luciferase comprises SEQ ID NO:1 or 5.

In some embodiments of the methods described herein, the sample is or includes a living cell, a living animal, a tissue or organ, or a cell or tissue extract.

In another aspect, the invention provides kits for use in a method of producing bioluminescence in a sample. The kits include a mutant luciferase, and a cognate substrate, wherein:

(a) the mutant luciferase comprises mutations at F247L, A313G, A313N, R218K, L342A, R218K+F247L, or R218K+T251Q, and the substrate is 6'-aminoluciferin;

(b) the mutant luciferase comprises mutations at S347A, S347T, L286M, T251S, F247S, F247V, R218K, L342A R218K+T251S, R218K+S347A, R218K+T251M, R218K+L286M, R218K+L342A, L286M+S347A, R218K+T251E, R218K+T251S+S347H, R218K+ L286M+S347A, L286M+S347A, L286M+T251S, or L286M+L342A, and the substrate is CycLuc1;

(c) the mutant luciferase comprises mutations at S347A+ L286M and the substrate is CycLuc1, CycLuc3, or MeNHLH2;

(d) the mutant luciferase comprises mutations at A313F, R218Y, R218T, R218S, R218K, L342A, R218K+ F247Q, R218K+F247T, R218K+L342A, L286M+ L342A, or R218K+L286M+S347A and the substrate is CycLuc4;

(e) the mutant luciferase comprises mutations at L286M+ S347A and the substrate is CycLuc1 and/or CycLuc3;

(f) the mutant luciferase comprises mutations at F247L+ S347A and the substrate is MeNHLH2;

(g) the mutant luciferase comprises mutations at R218K, L342A, R218K+L342A, R218K+L286M+S347A, R218K+T251M, or R218K+F247L and the substrate is CycLuc2;

(h) the mutant luciferase comprises mutations at R218K+ L268M+S347A, R218K+L342A, R218K+S347A, R218K+T251S, R218K+L286M+S347A+L342A, or L286M+L342A and the substrate is CycLuc7;

(i) the mutant luciferase comprises mutations at A313F and the substrate is MeNHLH2, CycLuc1, CycLuc2, CycLuc3 and/or CycLuc4;

(j) the mutant luciferase comprises mutations at R128K and the substrate is CycLuc1-8', MeNH-LH2, iBuNH-LH2, (3-hydroxypropyl)NH-LH2, Me2N-LH2 and/or NH2-LH2;

(k) the mutant luciferase comprises mutations at L342A and the substrate is CycLuc1-8', MeNH-LH2, iBuNH-LH2, (3-hydroxypropyl)NH-LH2, Me2N-LH2 and/or NH2LH2; and/or (l) the mutant luciferase comprises mutations at R218K+ L342A and the substrate is CycLuc1-8, MeNH-LH2, iBuNH-LH2, (3-hydroxypropyl)NH-LH2, or Me2N-LH2.

In some embodiments of the kits described herein, the mutant luciferase comprises a mutated firefly luciferase, click beetle luciferase, glow worm luciferase, or railroad worm luciferase. In some embodiments, the firefly luciferase comprises SEQ ID NO:1 or 5.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIG. 9 is a sequence alignment of the protein sequences of five firefly luciferases: SEQ ID NO:1—*Luciola cruciate* (Japanese firefly); SEQ ID NO:2—*Luciola lateralis*; SEQ ID NO:3—*Luciola mingrelica* (East European fireflies); SEQ ID NO:4—*Photuris pennsylvanica* (Pennsylvania firefly); and SEQ ID NO:5, *Photinus pyralis* (North America firefly).

DETAILED DESCRIPTION

Figure 1:
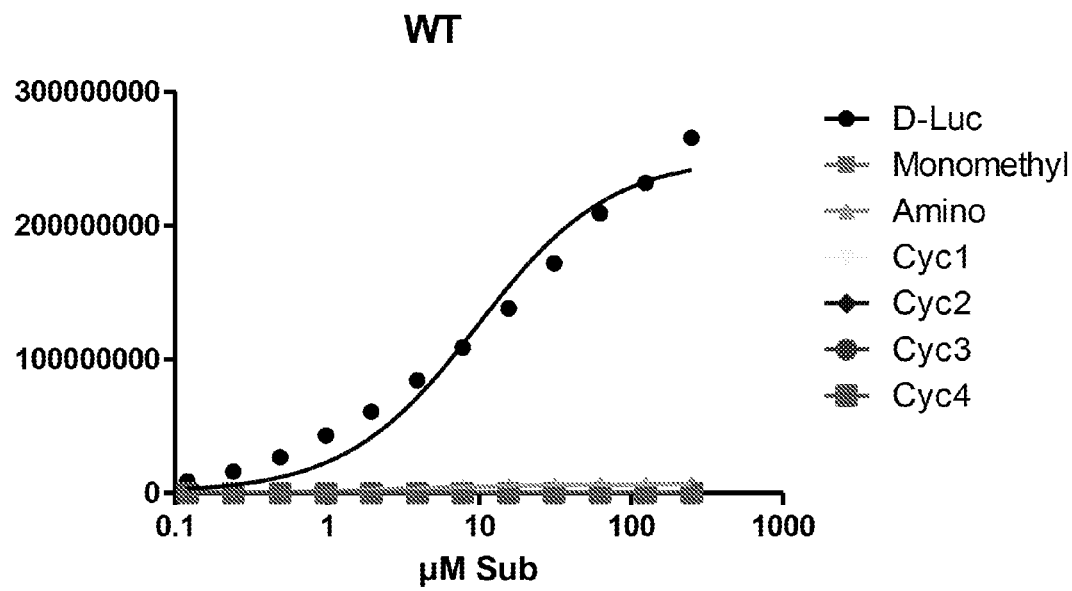
FIG. 1 is a line graph showing that D-luciferin was the best substrate for purified wild-type luciferase, followed by 6'-aminoluciferin, then CycLuc1. Alkylated aminoluciferins gave low light emission due in part to product inhibition. X-axis, μM substrate; Y-axis, Counts per second (cps). Photons were counted using a Turner Veritas luminometer. Curves were produced by curve fitting of the data with the Michaelis-Menten equation using GraphPad Prism 5.0.

To improve light emission from alkylaminoluciferin substrates, the present inventors synthesized a variety of synthetic luciferins in search of substrates that have high affinity for luciferase, efficient light emission, red-shifted light output, increased cell permeability, and reduced tendency to result in product inhibition (see, e.g., US2008/0226557). Mutant luciferases were screened for variants that exhibit improved and/or selective light output with synthetic alkylaminoluciferin substrates. Described herein are luciferases identified by those screens.

Isolated Mutant Luciferase Polypeptides

In another aspect, the invention features isolated mutant luciferase proteins. Mutant luciferase proteins can be isolated from cells or tissue sources using standard protein purification techniques. Mutant luciferase proteins can be produced by recombinant DNA techniques or synthesized chemically. The mutant luciferase proteins described herein have the ability to bind synthetic alkylaminoluciferin substrates and upon binding to produce luminescence. The mutant luciferase proteins have a sequence with one or more (e.g., two, three, four, or more) of the following mutations (numbering is based on SEQ ID NO:5, from the North American firefly: L342A; F247A; F247L; F247V; F247S; F247R; F247Q; F247T T251N; T251Q; T251V; T251I; T251S; L286T; L286Y; L286S; L286M; S347C; S347T; S347H; Q338W; R218K; R218V; R218Y; R218S; R218T; A313F; A313N; A313L; A313G; L286A; S347A; A348G; E311A; I351A; R337A and/or H245A.

Although the mutant luciferases exemplified herein were made by mutating a *Photinus pyralis* (North American or common eastern) firefly luciferase, mutant luciferases can also be made by mutating luciferases from other species, e.g., other species of fireflies, click beetles, railroad worms, etc. The amino acids to be mutated are identified by aligning the sequence to be mutated with the *P. pyralis* sequence to obtain the greatest identity (using methods known in the art), and mutating a residue (or multiple residues) that corresponds to a residue described herein, e.g., L342A; F247A; F247L; F247V; F247S; F247R; F247Q; F247T T251N; T251Q; T251V; T251I; T251S; L286T; L286Y; L286S; L286M; S347C; S347T; S347H; Q338W; R218K; R218V; R218Y; R218S; R218T; A313F; A313N; A313L; A313G; L286A; S347A; A348G; E311A; I351A; R337A and/or H245A. Sequences of wild type luciferases that can be mutated as described herein are known in the art, e.g., as described in de Wet et al., Mol Cell Biol. 7(2):725-37 (1987) or GenBank Acc. No. AAA29795.1 (*P. Pyralis*); Ye et al., Biochim. Biophys. Acta 1339:39-52 (1997) or GenBank Acc. No. AAB60897.1 (*P. pennsylvanica*); GenBank Acc. No. AAA29135.1 (*L. cruciate*); GenBank Acc. No. CAA47358.1 or Tatsumi et al., Biochim. Biophys. Acta 1131(2): 161-5 (1992) (*L. lateralis*); Devine et al., Biochim. Biophys. Acta 1173(2): 121-32 (1993) or GenBank Acc. No. AAB26932.1 (*L. mingrelica*); Choi et al., Comp Biochem Physiol B Biochem Mol Biol. 2003 February; 134(2):199-214 or GenBankk Acc. No. AAN40979.1 or AAN40976.1 (Hotaria tsushimana). See also Viviani, Cell Mol Life Sci. 59(11):1833-50 (2002); Viviani, Comp. Biochem. Physiol. B, Biochem. Mol. Biol. 139 (2), 151-156 (2004); Koksharov and Ugarova, Biochemistry (Mosc). 73(8):862-9 (2008); and de Wet et al., Proc Natl Acad Sci USA. 82(23):7870-3 (1985). An exemplary alignment of some firefly luciferases is shown in FIG. 9. Other luciferases can also be used, e.g., from the railroad worm (e.g., *Phrixothrix hirtus*: GenBank Acc. No. ACT68597.1 or AF139645.2; or *Phrixothrix vivianii*: GenBank Acc. No. AAD34542.1; see, e.g., Viviani et al., Biochemistry. 38(26):8271-9 (1999)); the click beetle (e.g., *Pyrophorus* sp., e.g., *Pyrophorus plagiophthalamus*: GenBank Acc. No. AAQ11734.1; *Pyrophorus angustus luscus*, GenBank Acc No. BAI66601.1; or *Pyrophorus mellifluous*, GenBank Acc. No. AAQ19141.1; see e.g. Wood et al., J Biolumin Chemilumin. 4(1):289-301 (1989)); GenBank Acc. No. AAW72003.1) or glow-worm (e.g., *Lampyris turkestanicus*: Alipour et al., Biochem. Biophys. Res. Commun. 325 (1), 215-222 (2004) or GenBank Acc. No. AAU85360.1; *Lampyris noctiluca*: GenBank Acc. No. AAW72003.1; or *Lampyris sardiniae*: GenBank Acc. No. ACH87788.1). Additional luciferase sequences can be identified, e.g., bioinformatically, using readily available tools such as the Basic Local Alignment Search Tool (BLAST) from the National Library of Medicine. Luciferases have the ability to produce bioluminescence in the presence of a luciferin substrate as described herein, and will have at least 40%, e.g., at least 50%, 60%, 70%, 80%, 90%, or 95% identity to a reference luciferase sequence described herein over at least 80%, e.g., at least 90%, 95%, 99%, or 100% of the length of the reference sequence.

Alternatively or in addition, a luciferase having one or more additional mutations can be used, e.g., as described in Rowe et al., Anal Chem. 2009 Nov. 1; 81(21):8662-8. Examples include thermostable luciferases (e.g., 4TS) as described in Koksharov and Ugarova, Protein Engineering, Design & Selection vol. 24 no. 11 pp. 835-844, 2011, e.g., comprising mutations at R211L, A217V, E356K and S364C in the *L. mingrelica* luciferase; additional thermostable luciferases are described in WO 99/14336 (e.g., Luc49-7C6; 78-0B10; or 90-1B5). Red-shifted mutant luciferases are described in Branchini et al., Analytical Biochemistry 396 (2010) 290-297. The ONE-GLO mutant luciferase can also be used (Promega). Other mutations are described in U.S. Pat. Nos. 7,452,663 and 7,723,502; and WO 99/14336.

In some embodiments the mutant luciferase protein differs from the reference luciferase sequence at positions in addition to the specific mutations described above. In some embodiments it differs by at least one but by less than 15, 10 or 5 amino acid residues. In another it differs from the corresponding sequence in FIG. 9 by at least one residue but less than 20%, 15%, 10% or 5% of the residues in it differ from the corresponding sequence in FIG. 9. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In some embodiments the differences are not in a domain that is conserved across the family shown in FIG. 9.

In some embodiments the protein contains one or more changes in amino acid sequence, e.g., a change in an amino acid residue which is not essential for activity. Such mutant luciferase proteins differ in amino acid sequence from those in FIG. 9, yet retain biological activity, i.e., the ability to bind synthetic alkylaminoluciferin substrates and upon binding to produce luminescence.

In one embodiment, the protein includes an amino acid sequence at least about 80%, 85%, 90%, 95%, 98% or more homologous to a sequence in FIG. 9.

Isolated Mutant Luciferase Nucleic Acid Molecules

In one aspect, the invention provides isolated nucleic acid molecules that encode a mutant luciferase polypeptide described herein. In some embodiments, an isolated nucleic acid molecule of the invention includes a nucleotide sequence encoding a protein with one or more (e.g., two, three, four, or more) of the following mutations (numbering is based on SEQ ID NO:5, from the North American firefly): L342A; F247A; F247L; F247V; F247S; F247R; F247Q; F247T T251N; T251Q; T251V; T251I; T251S; L286T; L286Y; L286S; L286M; S347C; S347T; S347H; Q338W; R218K; R218V; R218Y; R218S; R218T; A313F; A313N; A313L; A313G; L286A; S347A; A348G; E311A; I351A; H245A and/or R337A.

The nucleic acid molecules can be prepared by mutating a natural luciferase gene, e.g., a gene encoding a luciferase known in the art, e.g., the luciferase proteins described above. Examples include those described in de Wet et al., Mol Cell Biol. 7(2):725-37 (1987) or GenBank Acc. No. M15077.1 (*P. Pyralis*); Ye et al., Biochim. Biophys. Acta 1339:39-52 (1997) or EMBL-Bank Acc. No. U31240.1 (*P. pennsylvanica*); GenBank Acc. No. M26194.1 (*L. cruciate*); EMBL-Bank Acc. No. X66919.1 or Tatsumi et al., Biochim. Biophys. Acta 1131(2): 161-5 (1992) (*L. lateralis*); Devine et al., Biochim. Biophys. Acta 1173(2): 121-32 (1993) or EMBL-Bank Acc. No. S61961.1 (*L. mingrelica*). See also Viviani, Cell Mol Life Sci. 59(11):1833-50 (2002); Koksharov and Ugarova, Biochemistry (Mosc). 73(8):862-9 (2008); and de Wet et al., Proc Natl Acad Sci USA. 82(23): 7870-3 (1985).

In one embodiment, an isolated mutant luciferase nucleic acid molecule includes a nucleotide sequence that is at least about 85% or more homologous to the entire length of a natural luciferase nucleotide sequence. In some embodiments, the nucleotide sequence is at least about 90%, 91%, 92%, 93%, 94%, 95%, 96%, 97%, 98%, 99% or 100% to a natural luciferase nucleotide sequence.

In addition to mutations in the sequence made to effect the amino acid changes described above, the sequence may also be codon-optimized to improve expression in a host organism. In general, codon usage is believed to reflect the availability of tRNA isoforms in different organisms; the most efficiently expressed genes thus will utilize the most abundant tRNA isoforms. Mammalian cells prefer cytosine (C) or guanine (G) in the third codon position; codons containing adenine (A) or thymidine (T) occur infrequently. Sequence modifications can be used possible to yield codons more amenable to mammalian expression (Wada et al. Nucleic Acids Res. 20:2111-2118 (1992)). Methods for making such modifications are known in the art.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

Chimeric or Fusion Mutant Luciferase Proteins

In another aspect, the invention provides chimeric or fusion proteins. As used herein, a "chimeric protein" or "fusion protein" includes a mutant luciferase polypeptide as described herein linked to a non-luciferase polypeptide. A "non-luciferase polypeptide" refers to a polypeptide having an amino acid sequence corresponding to a protein which is not substantially homologous to the luciferase protein, e.g., a protein which is different from the luciferase protein and which is derived from the same or a different organism. The mutant luciferase polypeptide of the fusion protein can correspond to all or a portion of a mutant luciferase amino acid sequence. The non-luciferase polypeptide can be fused to the N-terminus or C-terminus of the mutant luciferase polypeptide.

The fusion protein can include a moiety which has a high affinity for a ligand. For example, the fusion protein can be a GST-mutant luciferase fusion protein in which the mutant luciferase sequences are fused to the C-terminus of the GST sequences. Such fusion proteins can facilitate the purification of recombinant mutant luciferase. Alternatively, the fusion protein can be a mutant luciferase protein containing a heterologous signal sequence at its N-terminus. In certain host cells (e.g., mammalian host cells), expression and/or secretion of mutant luciferase can be increased through use of a heterologous signal sequence.

Fusion proteins can include all or a part of a serum protein, e.g., an IgG constant region, or human serum albumin.

Expression vectors are commercially available that already encode a fusion moiety (e.g., a GST polypeptide). A mutant luciferase-encoding nucleic acid can be cloned into such an expression vector such that the fusion moiety is linked in-frame to the to mutant luciferase protein.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a mutant luciferase nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., mutant luciferase proteins, mutant luciferase fusion proteins, and the like).

The recombinant expression vectors of the invention can be designed for expression of mutant luciferase proteins in prokaryotic or eukaryotic cells. For example, polypeptides of the invention can be expressed in E. coli, insect cells (e.g., using baculovirus expression vectors), yeast cells or mammalian cells. Suitable host cells are discussed further in Goeddel, (1990) Gene Expression Technology: Methods in Enzymology 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

To maximize recombinant protein expression in E. coli is to express the protein in a host bacteria with an impaired capacity to proteolytically cleave the recombinant protein (Gottesman, S., (1990) Gene Expression Technology: Methods in Enzymology 185, Academic Press, San Diego, Calif. 119-128). Another strategy is to alter the nucleic acid sequence of the nucleic acid to be inserted into an expression vector so that the individual codons for each amino acid are those preferentially utilized in E. coli (Wada et al., (1992) Nucleic Acids Res. 20:2111-2118). Such alteration of nucleic acid sequences of the invention can be carried out by standard DNA synthesis techniques.

The mutant luciferase expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873, 316 and European Application Publication No. 264,166). Developmentally-regulated promoters are also encompassed, for example, the murine hox promoters (Kessel and Gruss (1990) *Science* 249:374-379) and the α-fetoprotein promoter (Campes and Tilghman (1989) *Genes Dev.* 3:537-546).

Another aspect the invention provides a host cell which includes a nucleic acid molecule described herein, e.g., a mutant luciferase nucleic acid molecule within a recombinant expression vector or a mutant luciferase nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a mutant luciferase protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Viral vectors, including retroviral, lentiviral, or adenoviral vectors, and known methods can also be used.

A host cell of the invention can be used to produce (i.e., express) a mutant luciferase protein. Accordingly, the invention further provides methods for producing a mutant luciferase protein using host cells. In some embodiments, the methods include culturing the host cell of the invention (into which a recombinant expression vector encoding a mutant luciferase protein has been introduced) in a suitable medium such that a mutant luciferase protein is produced. In another embodiment, the method further includes isolating a mutant luciferase protein from the medium or the host cell.

In another aspect, the invention features, a cell or purified preparation of cells which include a mutant luciferase transgene. The cell preparation can consist of human or non human cells, e.g., rodent cells, e.g., mouse or rat cells, rabbit cells, or pig cells. In preferred embodiments, the cell or cells include a mutant luciferase transgene. The mutant luciferase transgene can expressed in the cells.

In another aspect, the invention features a host cell, e.g., a mammalian cell, e.g., a stem cell or differentiated cell, transformed with nucleic acid that encodes a mutant luciferase polypeptide.

Transgenic Animals

Also described herein are non-human transgenic animals. As used herein, a "transgenic animal" is a non-human animal, preferably a mammal, more preferably a rodent such as a rat or mouse, in which one or more of the cells of the animal includes a transgene that encodes a mutant luciferase. Other examples of transgenic animals include non-human primates, sheep, dogs, cows, goats, chickens, amphibians, and the like. A transgene is exogenous DNA that is integrated into or occurs in the genome of the cells of a transgenic animal. A transgene can direct the expression of an encoded mutant luciferase gene product in one or more cell types or tissues of the transgenic animal. Thus, a transgenic animal can be one in which a mutant luciferase gene has been introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a mutant luciferase protein to particular cells. A transgenic founder animal can be identified based upon the presence of a mutant luciferase transgene in its genome and/or expression of mutant luciferase mRNA or protein in tissues or cells of the animals. A transgenic founder animal can then be used to breed additional animals carrying the transgene. Moreover, transgenic animals carrying a transgene encoding a mutant luciferase protein can further be bred to other transgenic animals carrying other transgenes.

Mutant luciferase proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal.

Methods of Use

The mutant luciferase proteins and fusion proteins described herein can be used in any assay or method in which native luciferase can be used, e.g., in any assay in which bioluminescence is desired.

The mutant luciferase proteins and fusion proteins described herein can be expressed in cells, and the cells can be contacted with a substrate as described herein, e.g., a luciferin or alkylaminoluciferin substrate, either intact or after lysis, and bioluminescence can be measured in the cell. For example, the mutant luciferase can be under the control of a specific promoter to produce luminescence in a particular cell or time during development, e.g., as part of a luciferase reporter assay to detect gene expression.

For example, the methods and compositions described herein can be used for in vivo imaging and may improve the speed, detection limit, and depth penetration of bioluminescence imaging. For example, the compounds described herein can be used for the rapid and inexpensive evaluation of tumor progression and response to anti-cancer therapeutics in small animals, e.g., using transgenic non-human animals, e.g., mice, that express a mutant luciferase reporter gene linked to a promoter or gene that is expressed, e.g., selectively expressed, in the cells that are desired to be imaged (Greer and Szalay, *Luminescence*, 2002, 17:43-74). In the same way, expression of a selected protein of interest can be imaged in real time in a living cell or animal, using a cell or transgenic animal that expresses a reporter construct including a nucleic acid encoding a mutant luciferase linked in frame to a nucleic acid encoding the selected protein of interest, or to the promoter for the selected protein.

In general, the methods can be performed on cells or animals (e.g., non-human mammals, e.g., experimental animals, such as rodents, e.g., rats or mice) that express a luciferase or a mutated luciferase reporter construct. One of skill in the art will readily be able to make such cells or animals using standard molecular biological techniques. Sufficient amounts of any of the luciferins described herein are then added or administered to the cells or animals, and images of the bioluminescence obtained using standard imaging methods. In this way, promoter activity, protein expression, protein subcellular localization, protein translocation, and protein half-life, can be evaluated in real time in living cells and animals.

When an experimental animal is used, the cells containing the bioluminescence can be identified and excised, and evaluated further, e.g., using assays for gene expression, protein expression, or other genetic or biochemical parameters.

The design and use of specific luciferin/luciferase pairs (e.g., with different emission maxima, e.g., D-luciferin with wt, and CycLuc1 with F247A) can allow for simultaneous imaging of bioluminescence from two or more luciferases.

The methods described herein can be practiced with any imaging system that can detect near infrared bioluminescence, e.g., the in vivo imaging systems described in Doyle et al., Cellular Microbiology (2004) 6(4):303-317. Common imaging systems are available from Xenogen (e.g., IVIS), Hamamatsu, Roper, and Kodak.

Luciferin Substrates—Aminoluciferins and Alkylaminoluciferins

The present luciferases can be used in combination with luciferin substrates or analogs thereof including D-Luciferin, aminoluciferins and alkylaminoluciferins, e.g., cyclic alkylaminoluciferins, known in the art or disclosed herein.

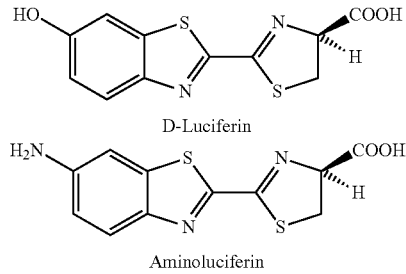

As shown above, aminoluciferin (aLuc) is luciferin with its 6-position hydroxyl group substituted with an amino group. As used herein, the term "alkylaminoluciferin" refers to an aminoluciferin that has been alkylated at the amino moiety of the aminoluciferin. For example, alkyl groups include a saturated hydrocarbon group having straight, branched or cyclic chain or any combination thereof. Examples of an alkyl group include methyl, ethyl, n-propyl, isopropyl, cyclopropyl, n-butyl, sec-butyl, isobutyl, tert-butyl, cyclopropylmethyl, n-pentyl, n-hexyl, and the like. In some embodiments, the amino group can be dialkylated, and the two alkyl groups together with the amino group to which they are attached form a cyclic group. The cyclic group together with the amino group form a 5- or 6-membered ring, i.e. a pyrrolidine or piperidine ring.

Figures 10, 11A:
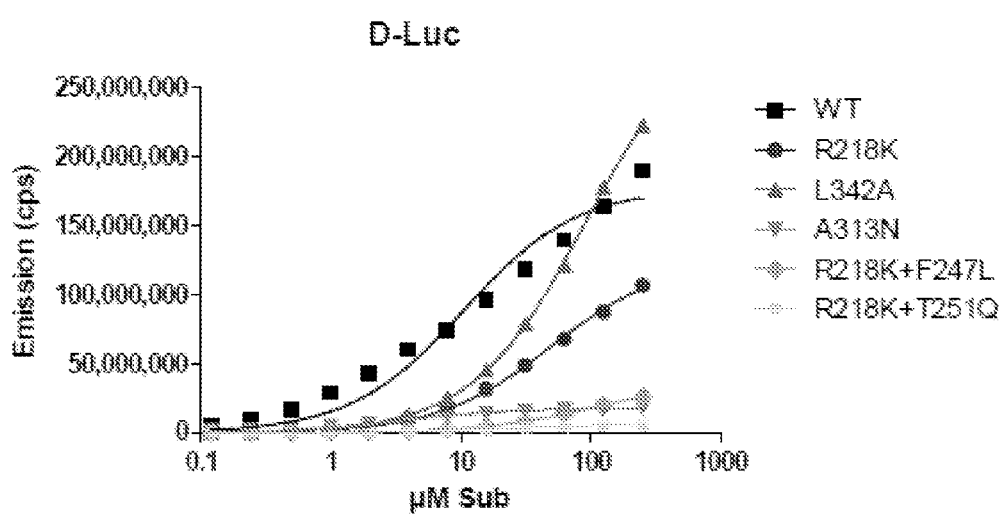
FIG. 10 shows the structures of a number of exemplary alkylaminoluciferins useful in the methods and kits described herein.
FIGS. 11A-B are line graphs showing several mutants that give improved bioluminescence with aminoluciferin as compared to wild type.

Exemplary alkylaminoluciferins include CycLuc1, CycLuc2, CycLuc3, CycLuc4, CycLuc5, CycLuc6, CycLuc7, CycLuc7', CycLuc8, and CycLuc8', as shown in FIG. 10, described below. Synthesis methods for CycLuc1, CycLuc2, Monomethylaminoluciferin (MeNHLH2), as well as Me2NLH2, are all described in Reddy et al., J Am Chem Soc. 132(39):13586-7 (2010). The methyl group in MeN-HLH2 can be replaced with other moieties, e.g., with ethyl, isopropyl, isobutyl, hydroxypropyl, or the like. CycLuc3-CycLuc8' can be synthesized using methods similar to those described in US2008/0226557, e.g., as set forth below. NH2-LH2 (6'-aminoluciferin) is described in White et al., J. Am. Chem. Soc., 88 (9):2015-2019 (1966) and Monsees et al., Anal Biochem 221, 329-34 (1994). Other alkylaminoluciferins useful in the present methods and kits are described in Meroni et al., ARKIVOC 2009 (i):265-288 (2009); U.S. Pat. No. 7,524,876; US2008/0226557; and the N-Alkylated 6'-Aminoluciferins described in Woodroofe et al., Biochemistry 47:10383-10393 (2008).

D-luciferin analogs can also be used, e.g., 5'-fluoroluciferin (U.S. Pat. No. 7,951,550), 7'-iodoluciferin (Lee et al., Bioorganic & Medicinal Chemistry Letters 14:1161-1163 (2004)), 4'-methylluciferin (Farace et al., J. Clin. Chem. Clin. Biochem. 28:471-474 (1990)); naphthyl- and quinolyl-luciferin (see, e.g., Branchini et al., Photochemistry and Photobiology 49(5):689-695 (1989)).

Additional analogs of luciferin are known in the art, see, e.g., U.S. Pat. No. 7,951,550; U.S. Pat. No. 7,524,876; US 20070155806; US 20040248225; U.S. Pat. No. 5,098,828; U.S. Pat. No. 5,035,999; and U.S. Pat. No. 6,160,024.

Kits

The present invention also includes kits that include one or more mutant luciferases as described herein, optionally in combination with a synthetic luciferin substrate, such as an aminoluciferin or alkylaminoluciferin substrate, e.g., a "cognate" substrate. As used herein, a cognate substrate is a substrate that has been shown to have desirable properties when used with a given mutant luciferase, e.g., 1) favorable Km; 2) reduced product inhibition; 3) sufficient or increased quantum yield of light emission; 4) desirable Vmax kinetics; 5) sufficient cell permeability, 6) selective utilization by a mutant luciferase over D-luciferin or another luciferin substrate. For example, the kit can include a combination such as:

6'-aminoluciferin with F247L, A313G, A313N, R218K, L342A, R218K+F247L, or R218K+T251Q;

CycLuc1 with S347A, S347T, L286M, T251S, F247S, F247V, R218K, L342A R218K+T251S, R218K+S347A, R218K+T251M, R218K+L286M, R218K+L342A, L286M+S347A, R218K+T251E, R218K+T251S+S347H, R218K+L286M+S347A, L286M+S347A, L286M+T251S, or L286M+L342A;

S347A+L286M with CycLuc1, CycLuc3, or MeNHLH2;

CycLuc4 with A313F, R218Y, R218T, R218S, R218K, L342A, R218K+F247Q, R218K+F247T, R218K+L342A, L286M+L342A, or R218K+L286M+S347A;

L286M+S347A with CycLuc1 and/or CycLuc3;

F247L+S347A with MeNHLH2;

CycLuc2 with R218K, L342A, R218K+L342A, R218K+L286M+S347A, R218K+T251M, or R218K+F247L;

CycLuc7 with R218K+L268M+S347A, R218K+L342A, R218K+S347A, R218K+T251S, R218K+L286M+S347A+L342A, or L286M+L342A, A313F with MeNHLH2, CycLuc1, CycLuc2, CycLuc3 and/or CycLuc4; and/or R128K with CycLuc1-8', MeNH-LH2, iBuNH-LH2, (3-hydroxypropyl)NH-LH2, Me2N-LH2 and/or NH2-LH2;

L342A with CycLuc1-8', MeNH-LH2, iBuNH-LH2, (3-hydroxypropyl)NH-LH2, Me2N-LH2 and/or NH2LH2;

R218K+L342A with CycLuc1-8, MeNH-LH2, iBuNH-LH2, (3-hydroxypropyl)NH-LH2, or Me2N-LH2. The kit can also contain other reagents useful in imaging methods, such as buffers and the like.

EXAMPLES

The invention is further described in the following examples, which do not limit the scope of the invention described in the claims.

Example 1

Generation of Mutant Luciferases

Initial efforts to improve luciferase light emission with alkylaminoluciferin substrates focused on rational mutation of phenylalanine 247 in the luciferin binding pocket. This residue is involved in a pi-stacking interaction with D-luciferin (Branchini et al., Biochemistry 42, 10429-36, 2003; Nakatsu et al., Nature 440, 372-376, 2006). Mutation of this residue to leucine and alanine has been previously reported by Branchini et al., who found that F247L lowers the affinity for D-luciferin but does not impair catalysis, while F247A is severely impaired in both Km and Vmax (Branchini et al., Biochemistry 42, 10429-36, 2003). It was therefore postulated that F247L would maintain catalytic function but allow improved product dissociation, helping to relieve product inhibition and allowing improvement in the sustained light emission from alkylaminoluciferin substrates.

Figure 2A:
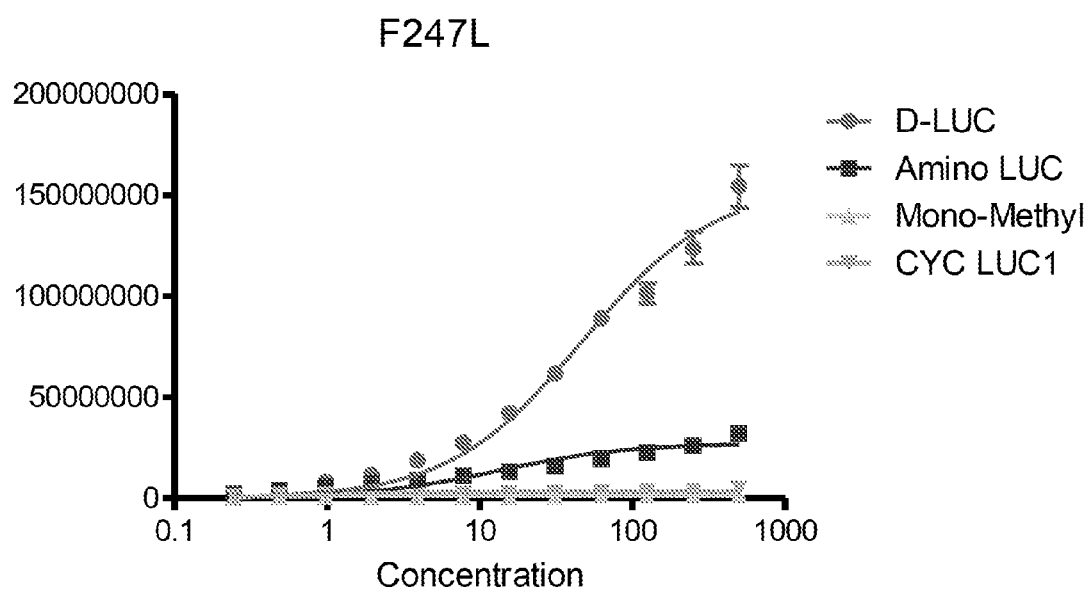
FIGS. 2A-H are line graphs showing light emission from purified single point mutant luciferases. Discrimination between substrates is evident. X-axis, μM substrate; Y-axis, Counts per second (cps). Photons were counted using a Turner Veritas luminometer. Curves were produced by curve fitting of the data with the Michaelis-Menten equation using GraphPad Prism 5.0.
Figure 2B:
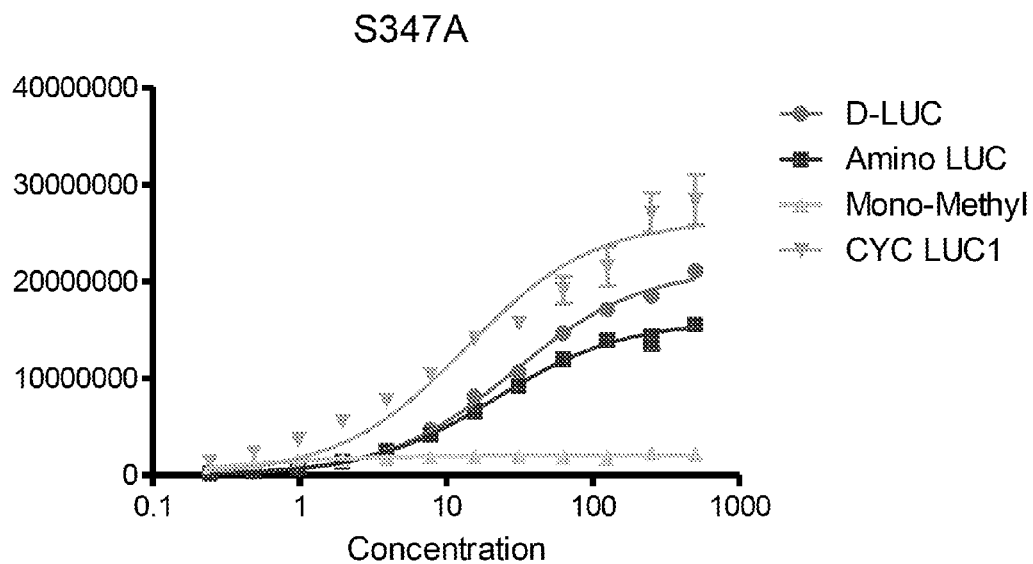
Figure 2C:
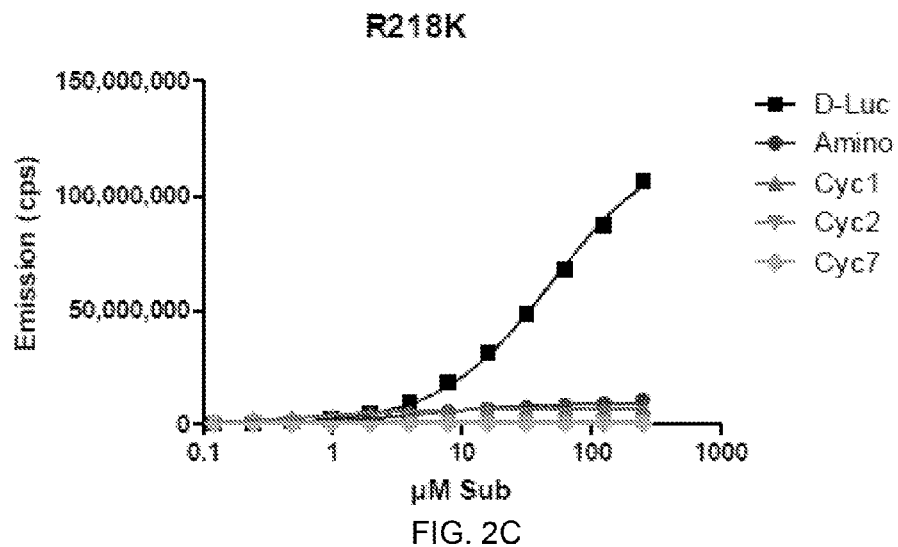
Figure 2D:
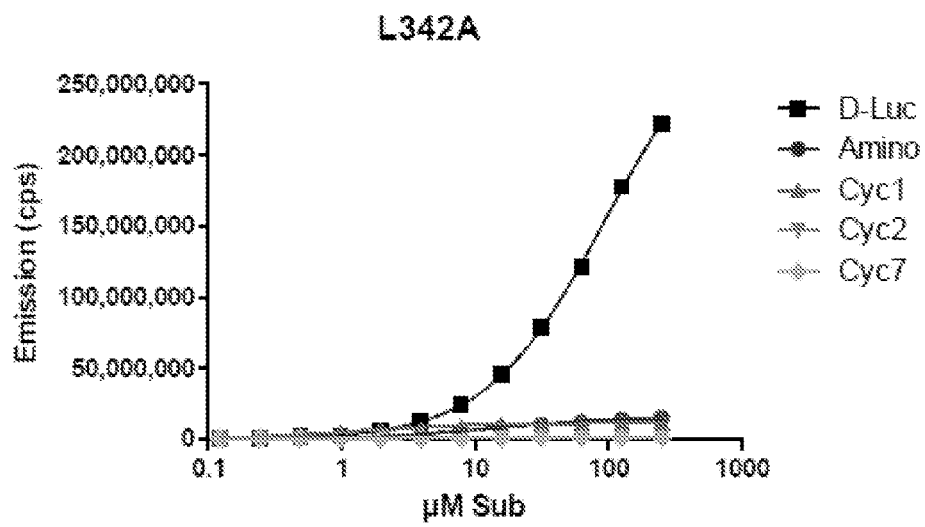
Figure 2E:
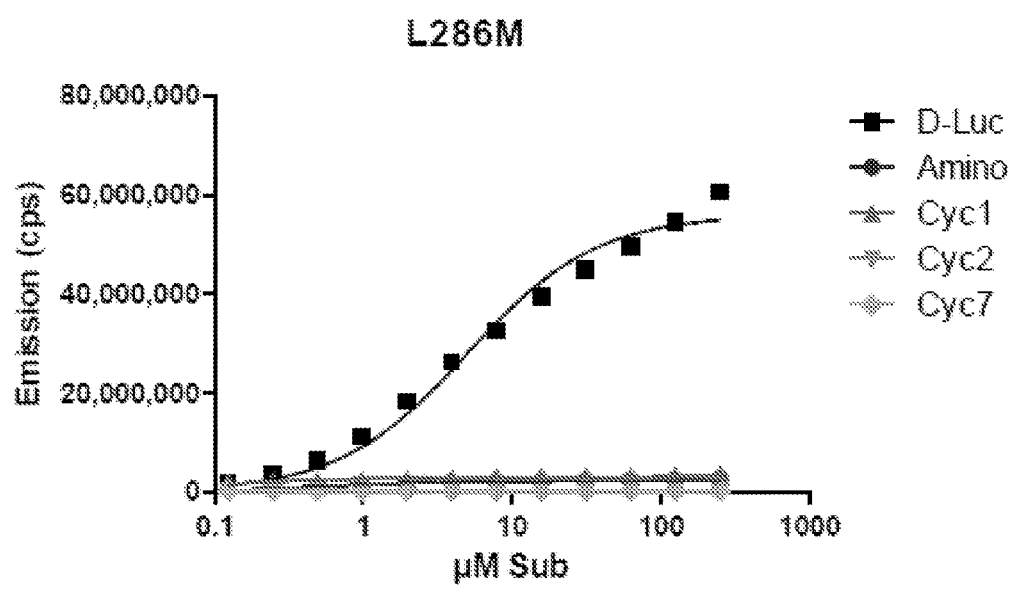
Figure 2F:
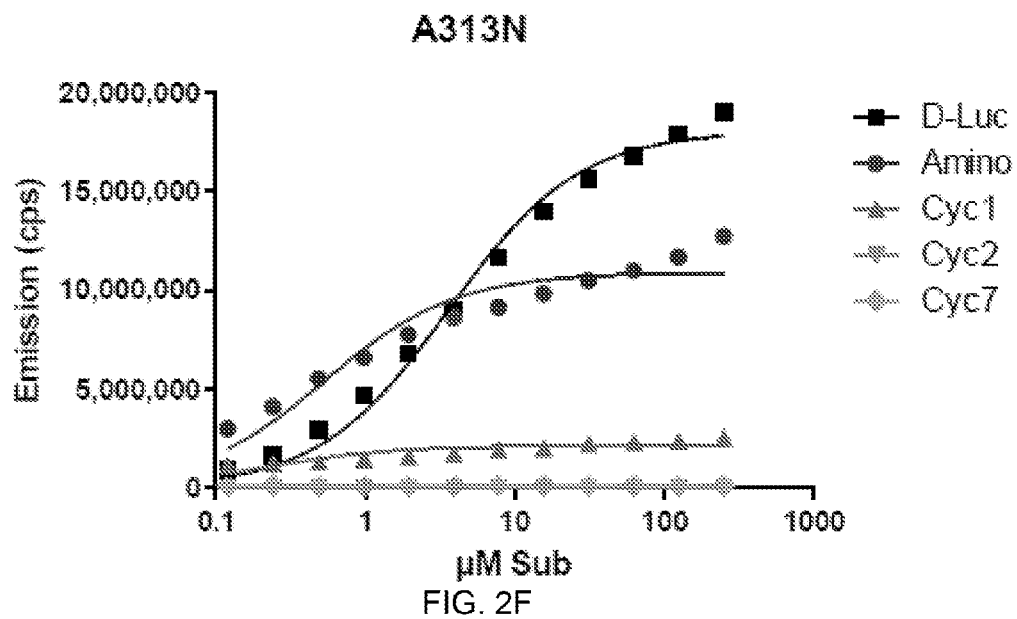
Figure 2G:
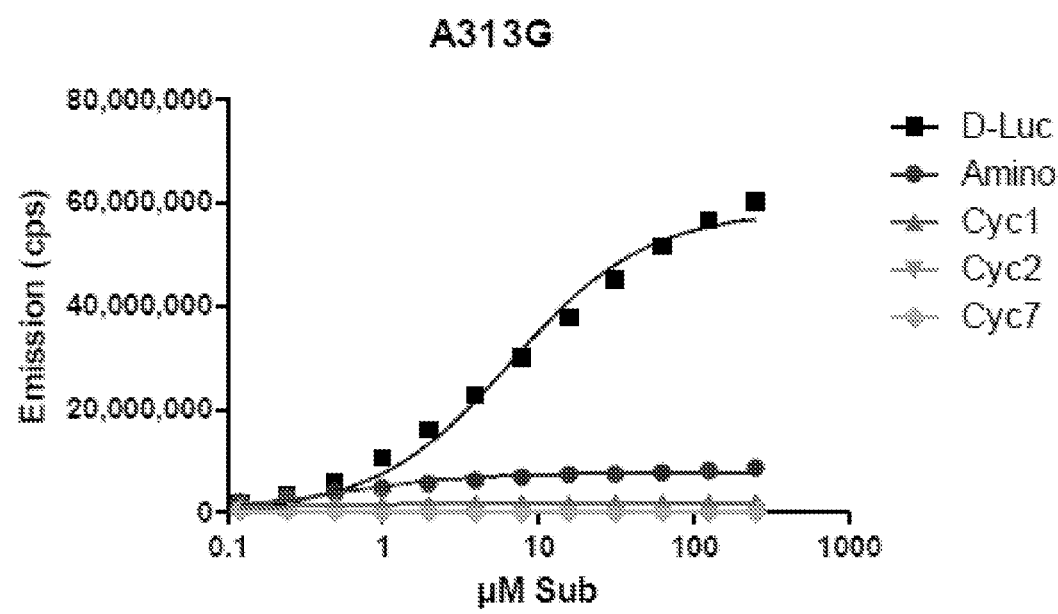
Figure 2H:
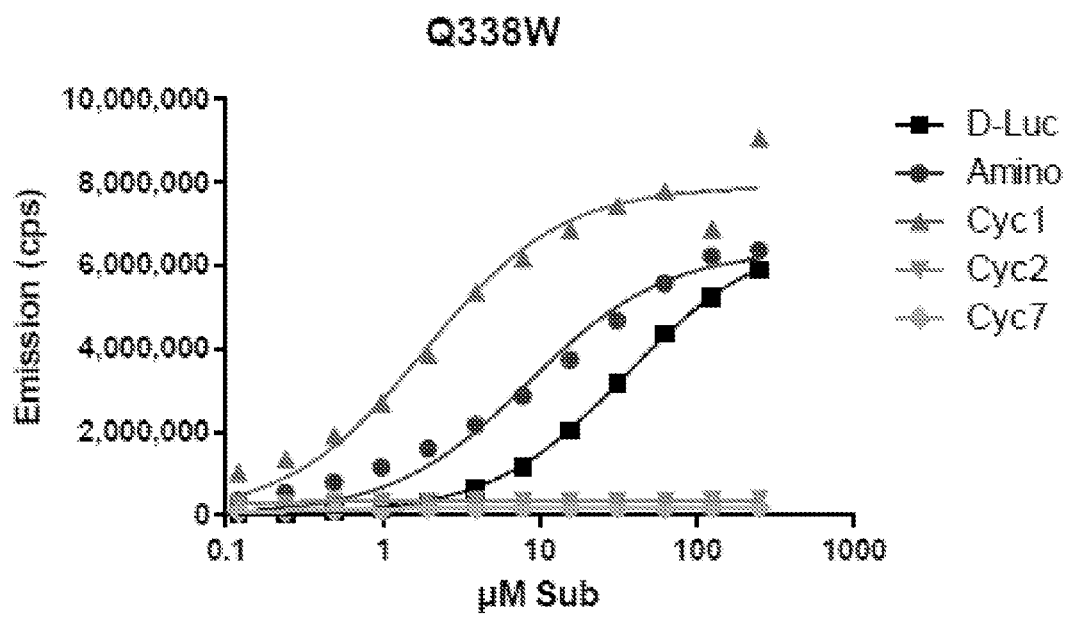
Figure 2I:
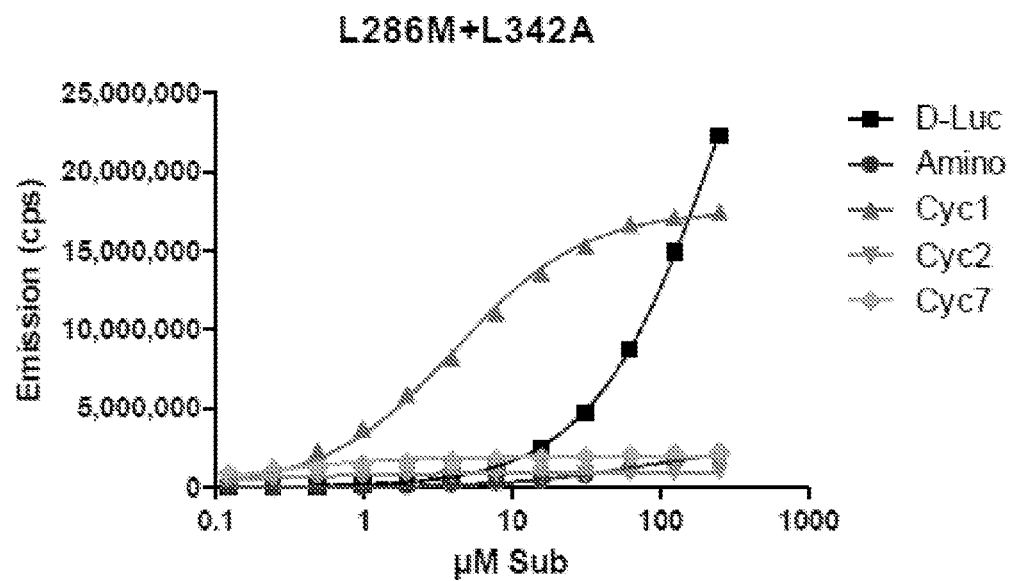
FIGS. 2I-O are line graphs showing light emission from purified double point mutant luciferases. Discrimination between substrates is evident. X-axis, μM substrate; Y-axis, Counts per second (cps). Photons were counted using a Turner Veritas luminometer. Curves were produced by curve fitting of the data with the Michaelis-Menten equation using GraphPad Prism 5.0.
Figure 2J:
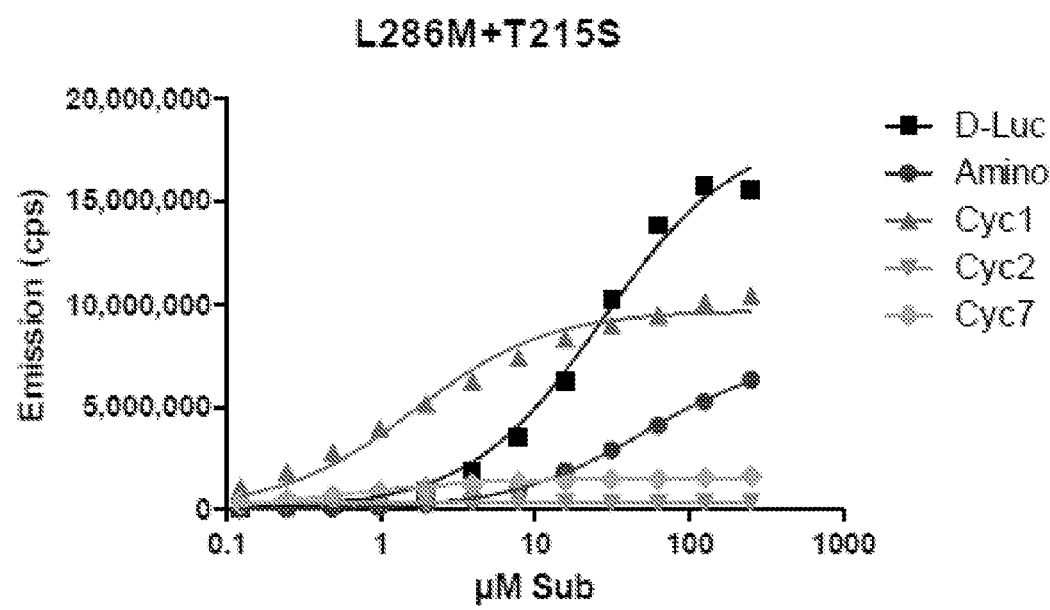
Figure 2K:
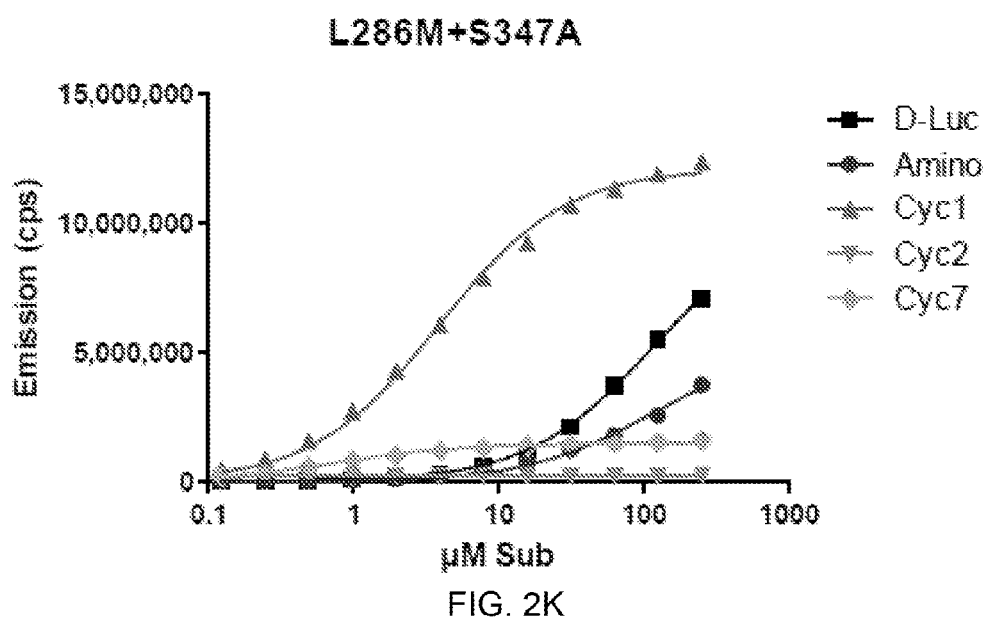
Figure 2L:
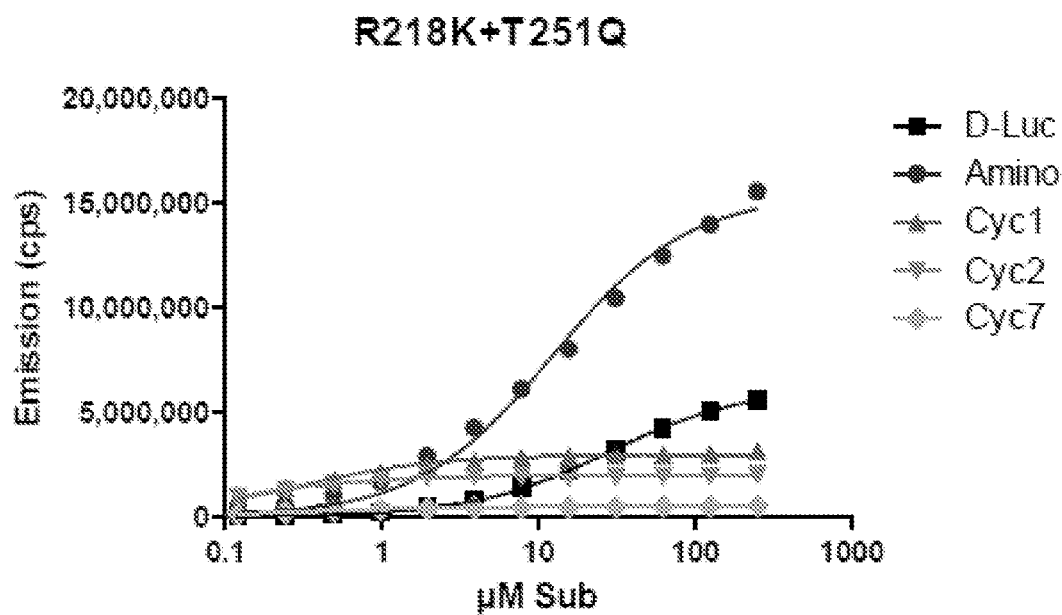
Figure 2M:
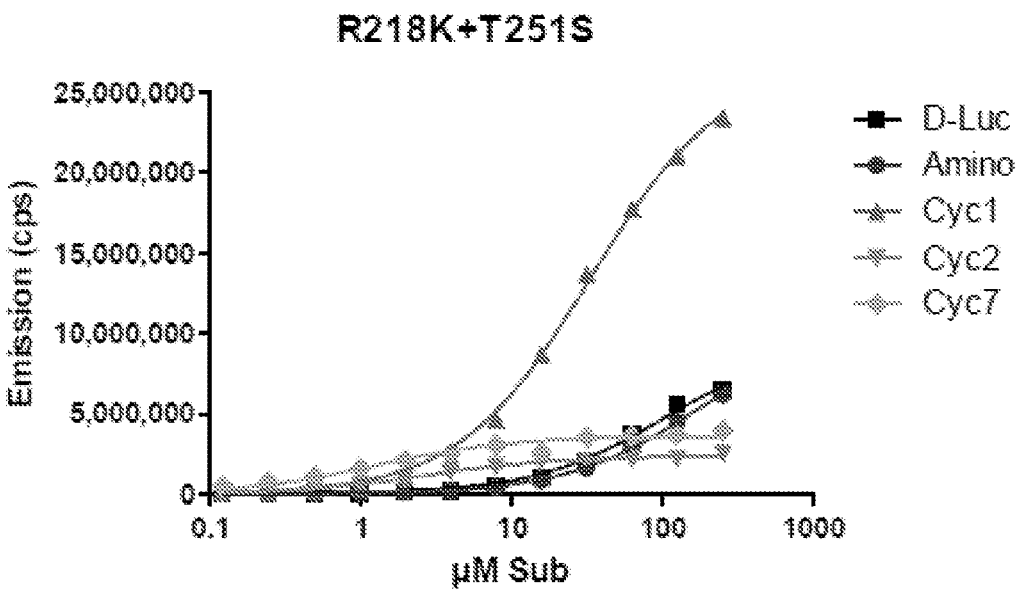
Figure 2N:
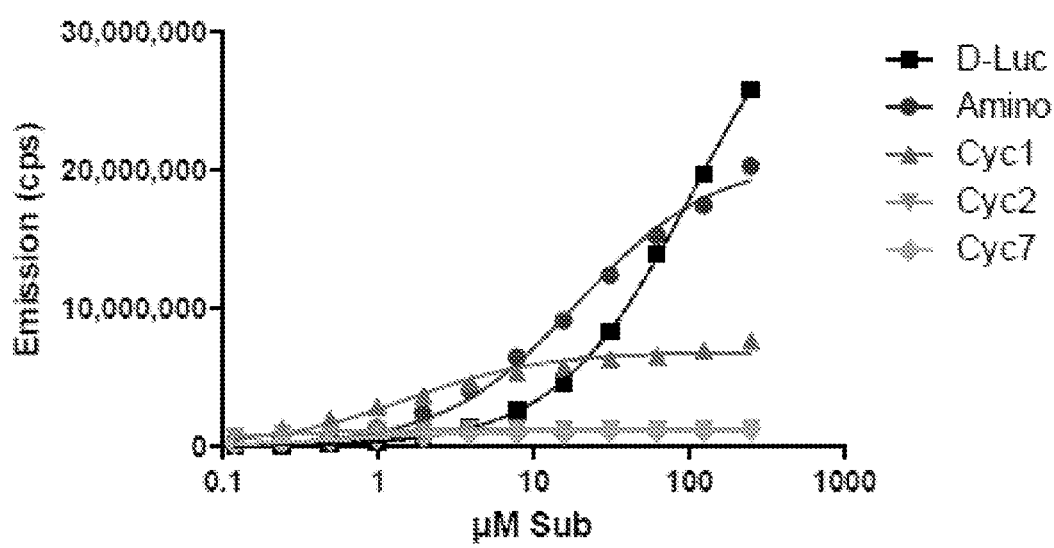
Figure 2O:
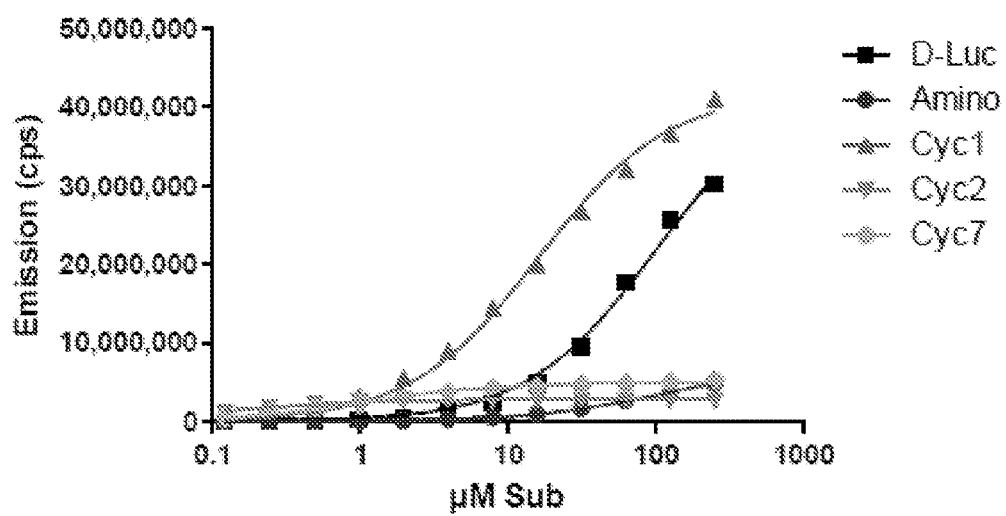
Figure 2P:
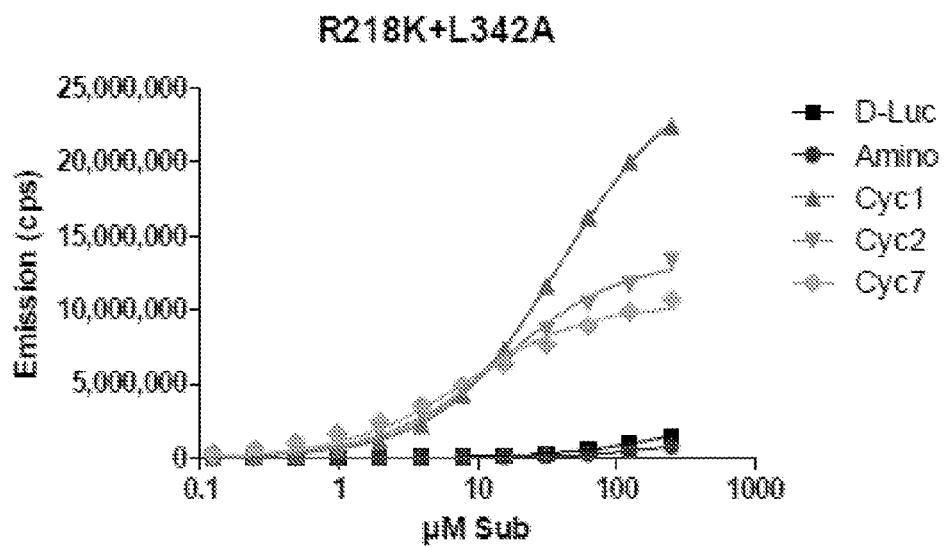
FIGS. 2P-X are line graphs showing loss of D-luciferin activity in double mutant luciferases. Discrimination between substrates is evident. X-axis, μM substrate; Y-axis, Counts per second (cps). Photons were counted using a Turner Veritas luminometer. Curves were produced by curve fitting of the data with the Michaelis-Menten equation using GraphPad Prism 5.0.
Figure 2Q:
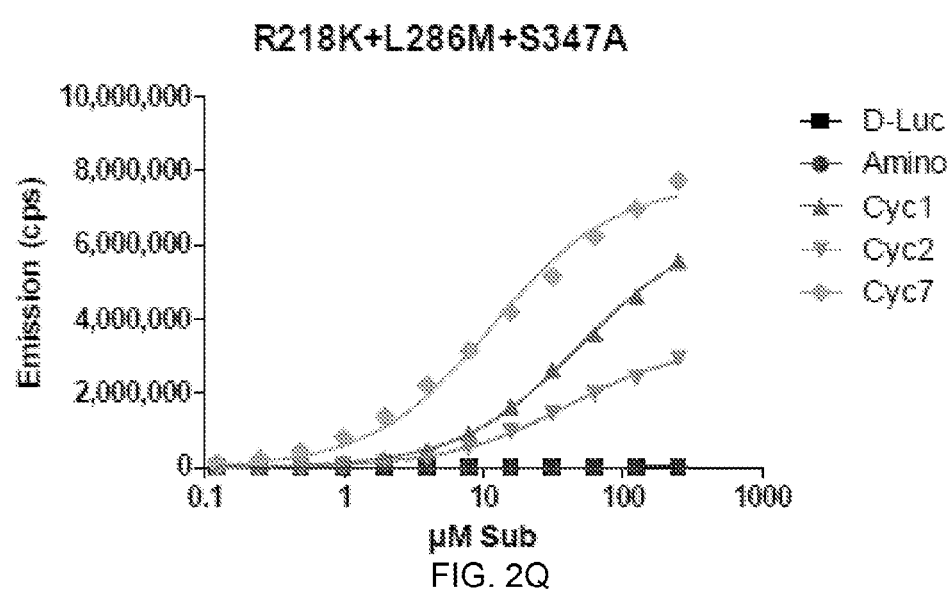
Figure 2R:
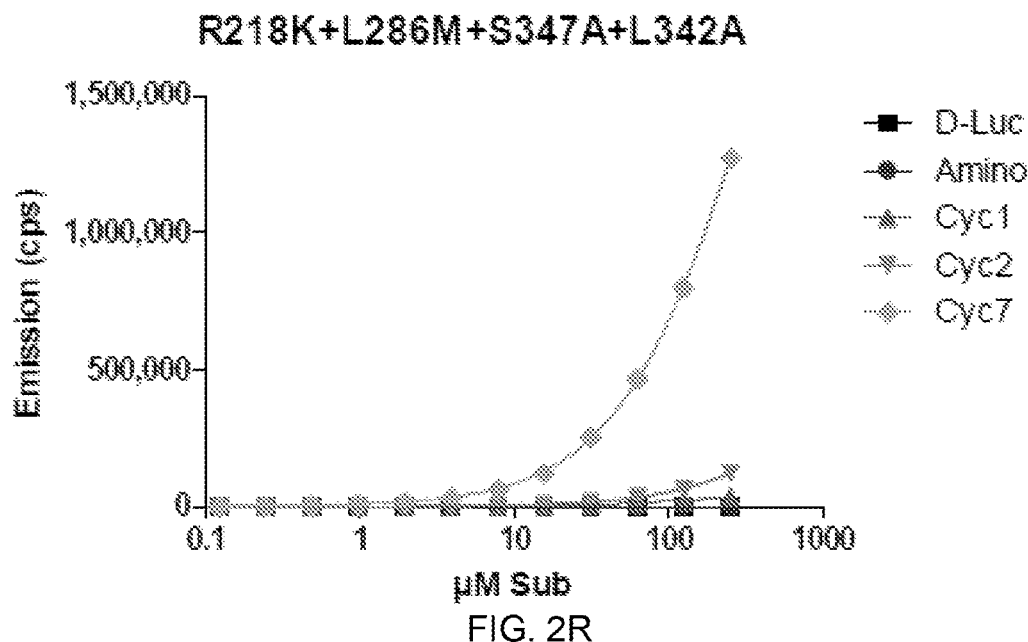
Figure 2S:
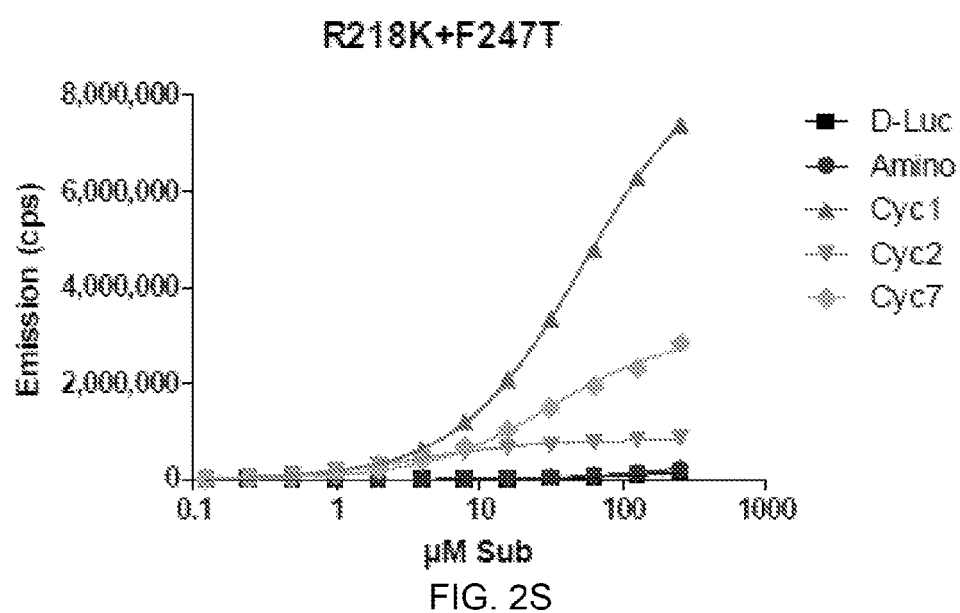
Figure 2T:
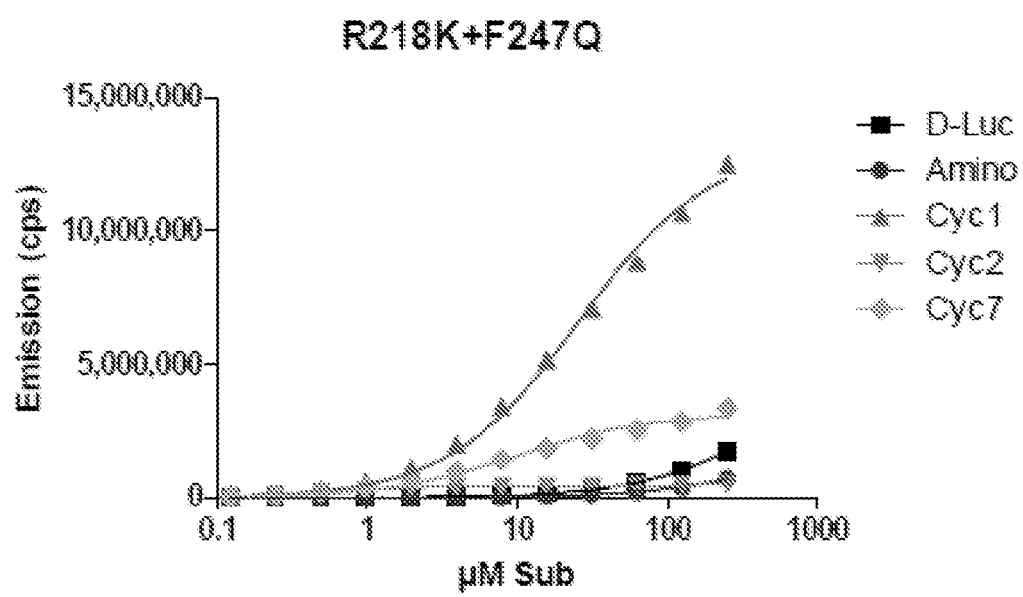
Figure 2U:
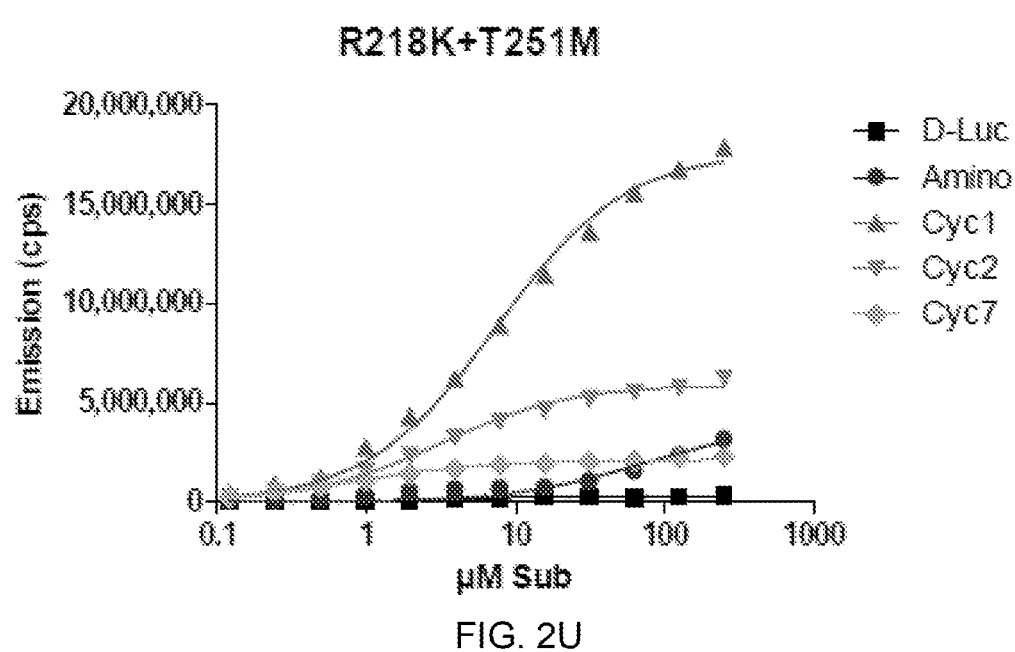
Figure 2V:
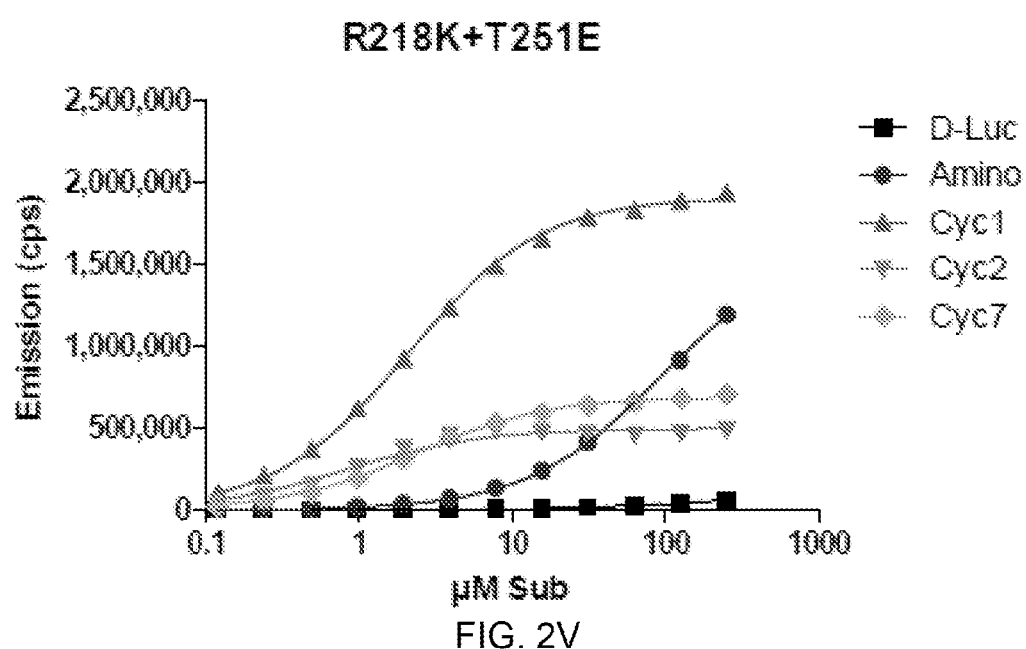
Figure 2W:
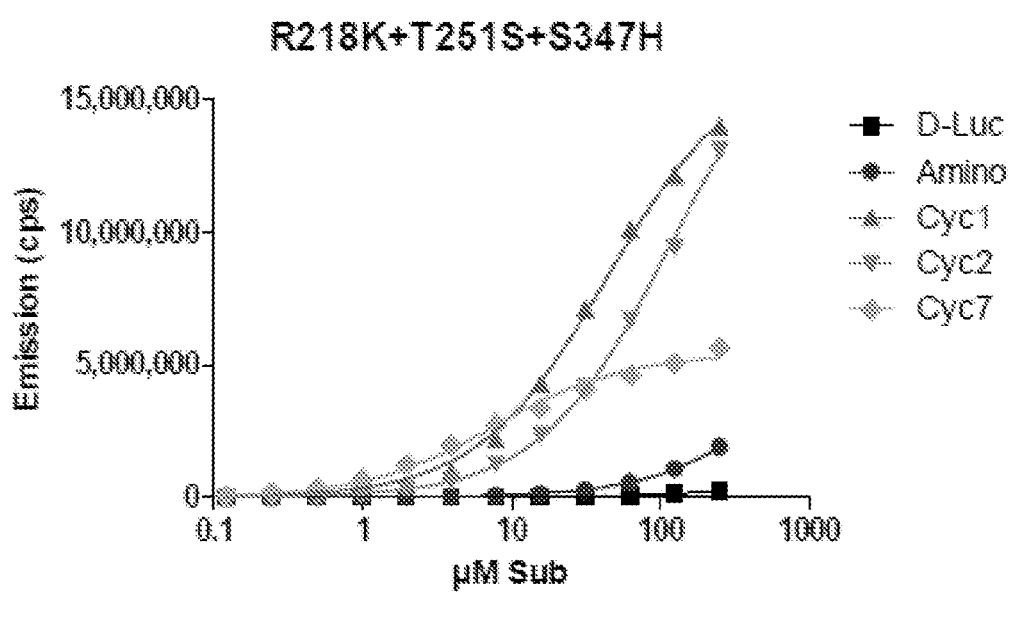
Figure 2X:
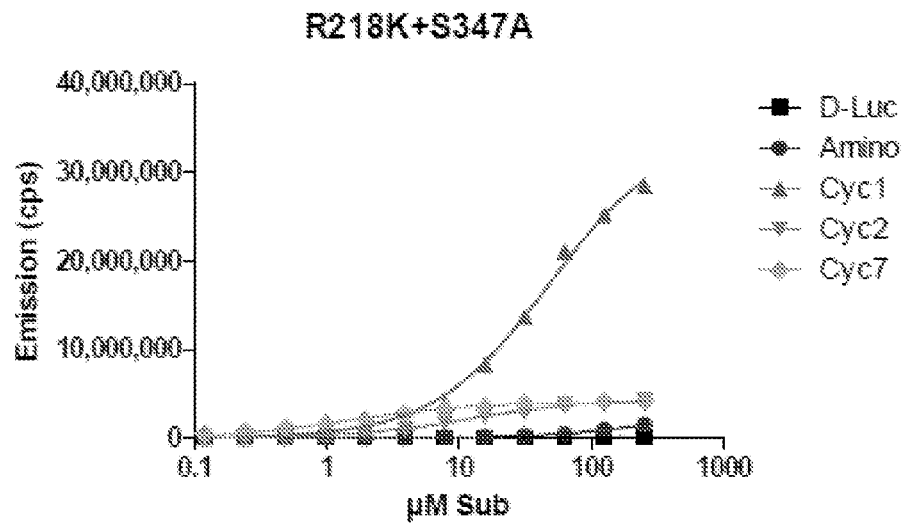
Figure 3A:
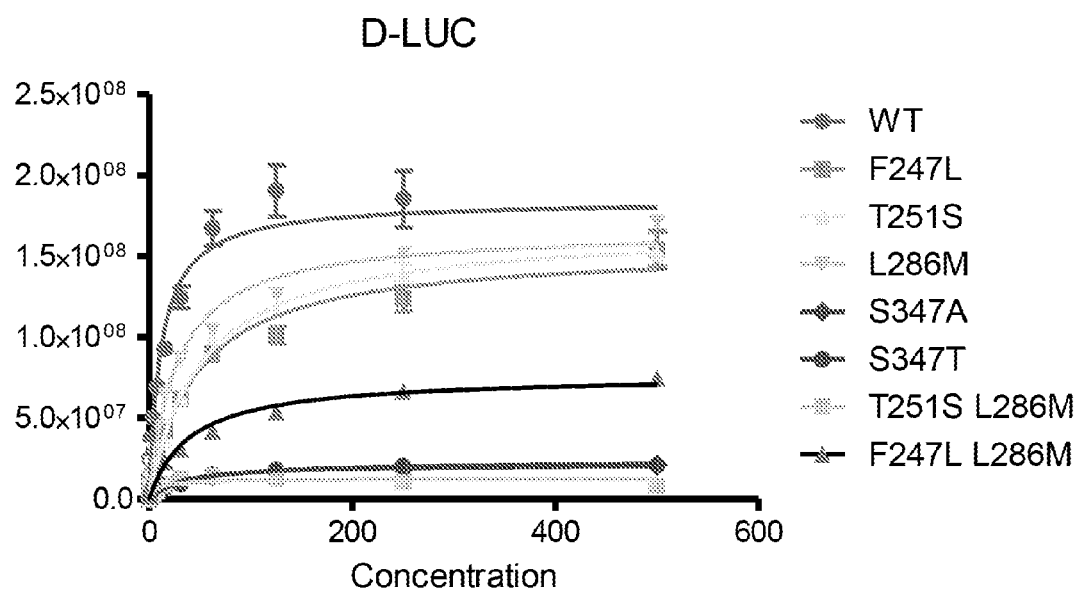
FIGS. 3A-C are line graphs showing relative light emission from purified mutant luciferases. Maximal light emission from D-luciferin was achieved by the wild-type luciferase. Light emission from 6'-aminoluciferin is enhanced by many of our mutants; maximal light emission is increased >5-fold by the mutant F247L. X-axis, substrate; Y-axis, Counts per second (cps). Photons were counted using a Turner Veritas luminometer. Curves were produced by curve fitting of the data with the Michaelis-Menten equation using GraphPad Prism 5.0.
Figure 3B:
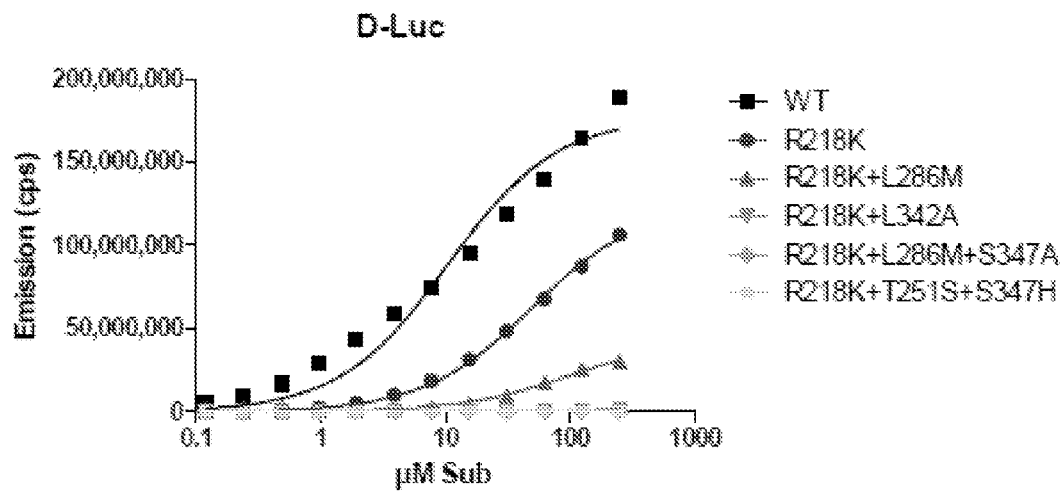
Figure 3C:
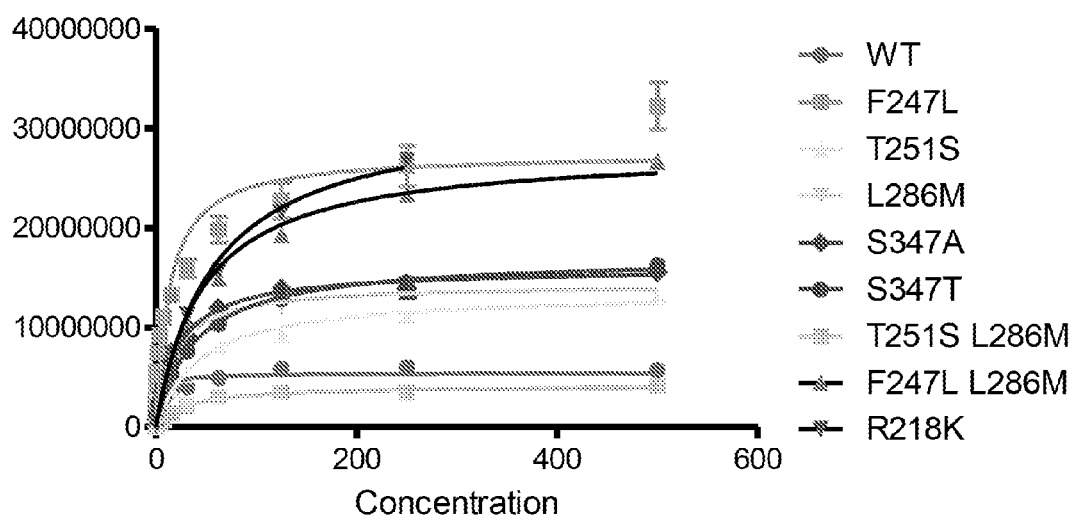
Figure 4A:
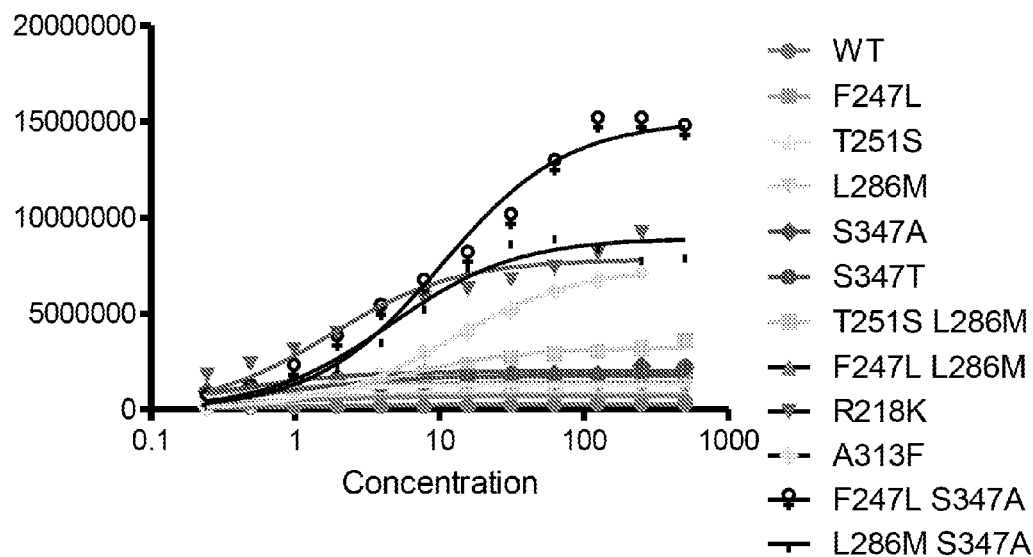
FIGS. 4A-E are line graphs showing that light emission from alkylaminoluciferins was significantly enhanced by mutation, and discrimination between substrates was achieved. X-axis, μM substrate; Y-axis, Counts per second (cps). Photons were counted using a Turner Veritas luminometer. Curves were produced by curve fitting of the data with the Michaelis-Menten equation using GraphPad Prism 5.0.
Figure 4B:
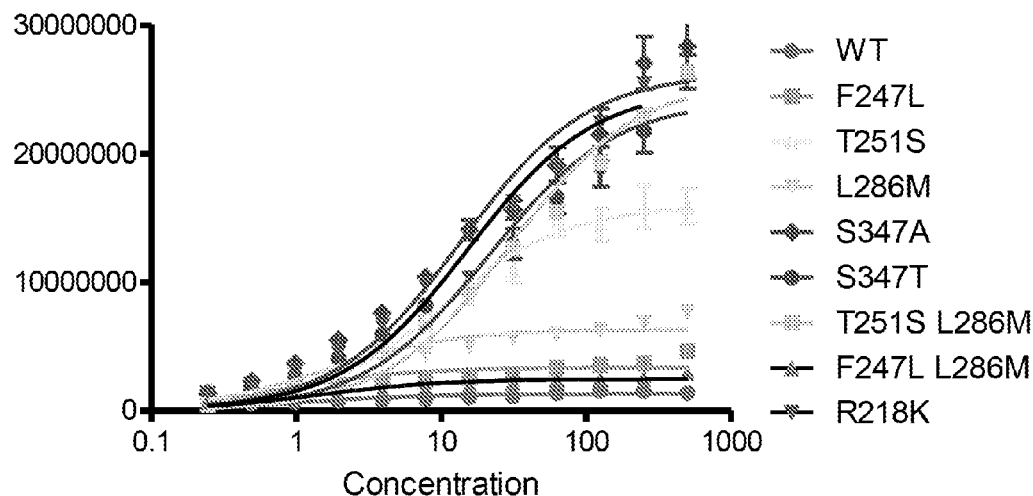
Figure 4C:
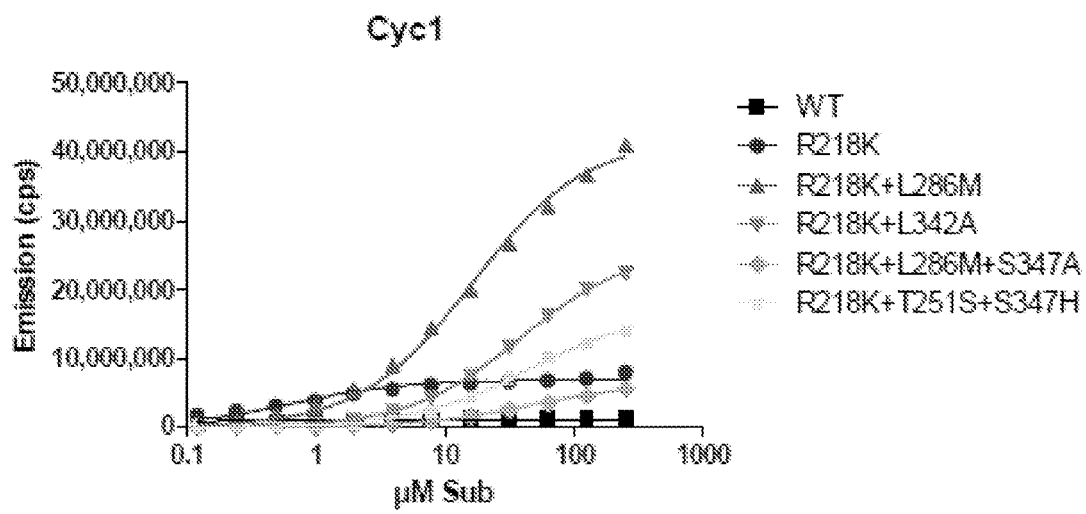
Figure 4D:
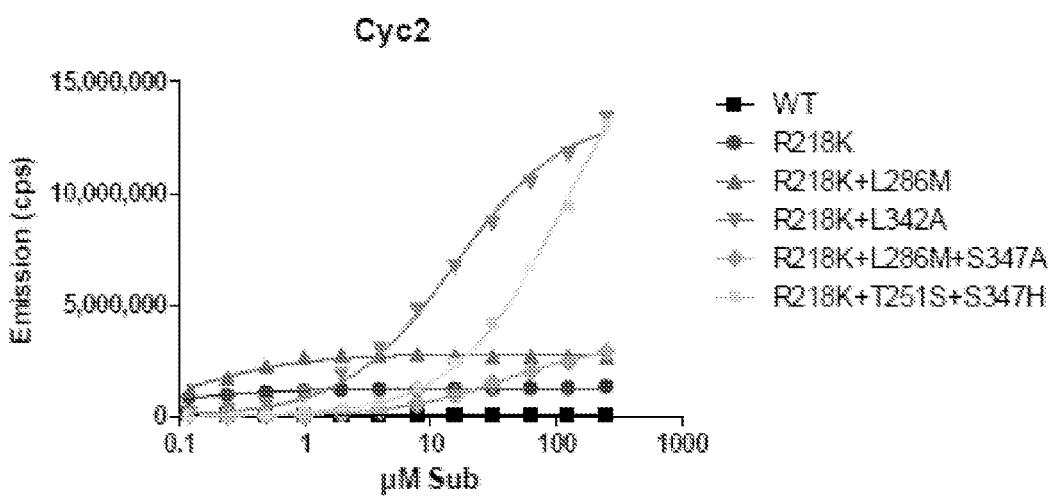
Figure 4E:
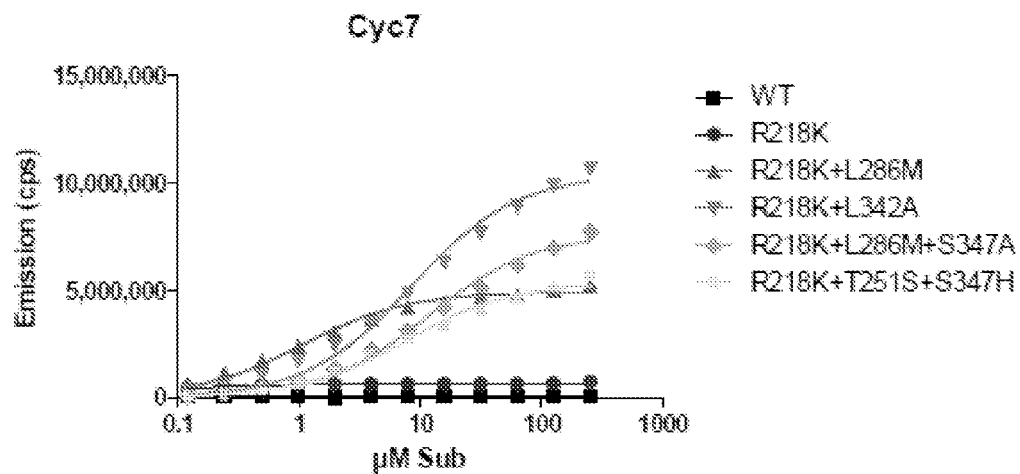
Figure 5A:
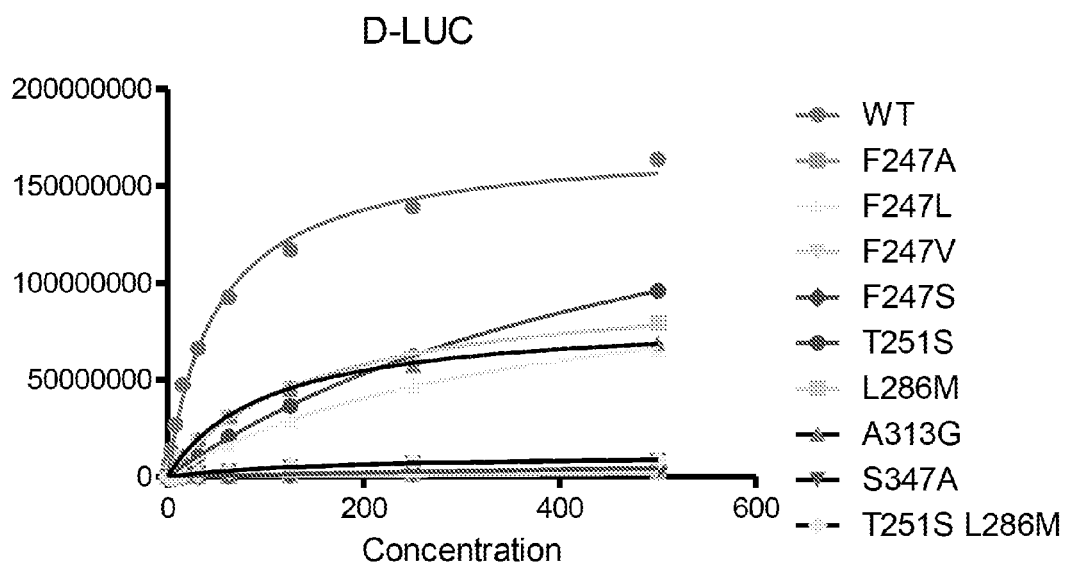
FIGS. 5A-C are line graphs showing light output from lysed CHO cells expressing mutant luciferases. X-axis, µM substrate; Y-axis, Counts per second (cps). Photons were counted using a Turner Veritas luminometer. Curves were produced by curve fitting of the data with the Michaelis-Menten equation using QraphPad Prism 5.0.
Figure 5B:
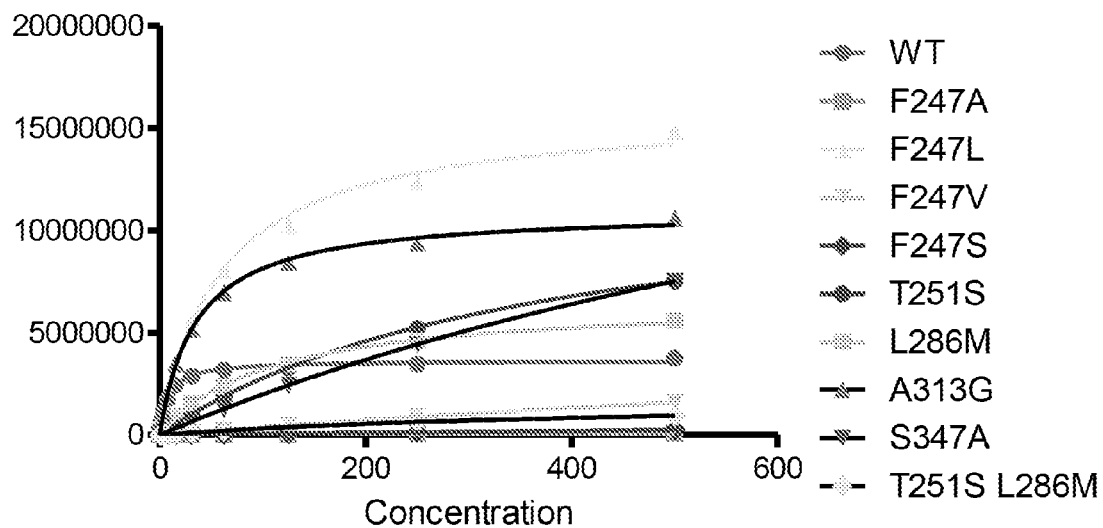
Figure 5C:
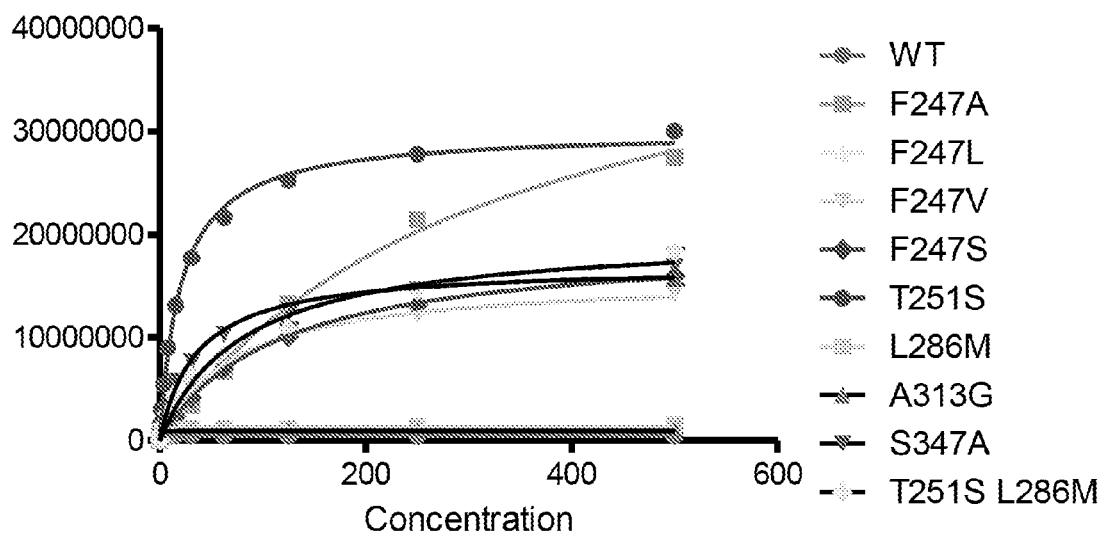
Figure 6:
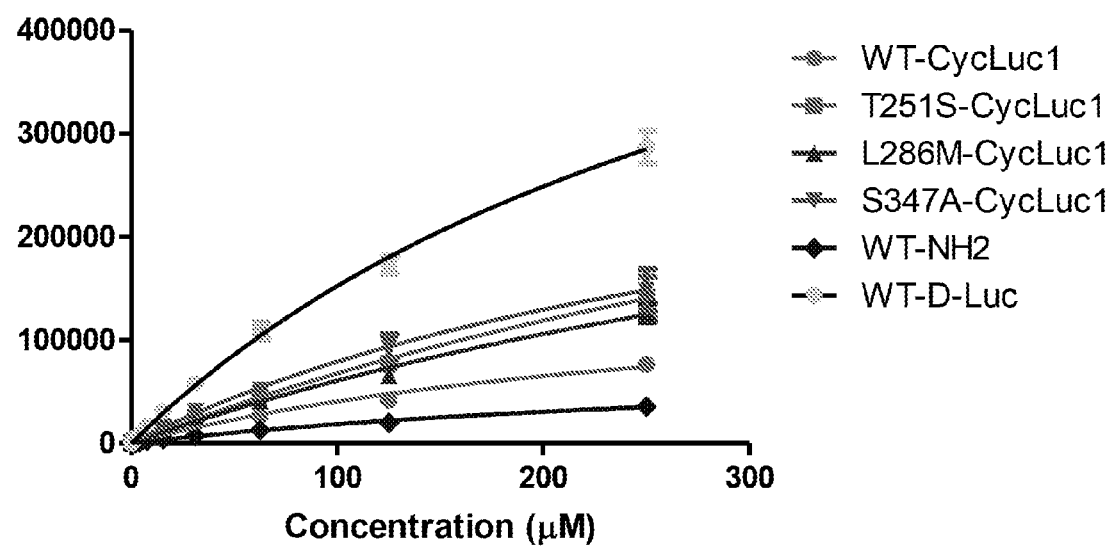
FIG. 6 is a line graph showing light emission from live, intact CHO cells expressing the indicated luciferase and treated with the indicated concentration of D-luciferin, 6'-aminoluciferin, or CycLuc1. Light output from CycLuc1 was superior to 6'-aminoluciferin, and was further improved by mutation of the luciferase. X-axis, µM substrate; Y-axis, Counts per second (cps). Photons were counted using a Turner Veritas luminometer. Curves were produced by curve fitting of the data with the Michaelis-Menten equation using GraphPad Prism 5.0.
Figure 7A:
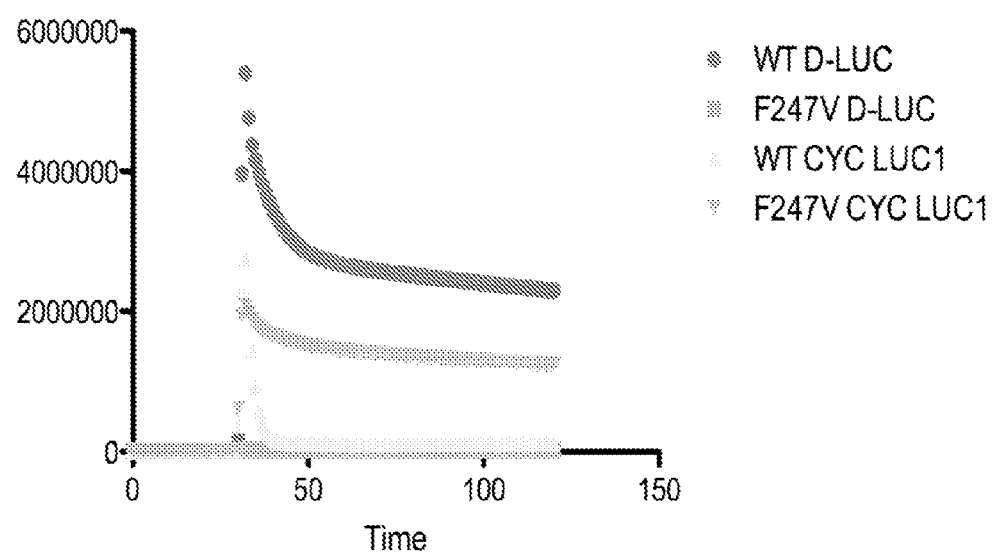
FIGS. 7A-I are graphs showing the kinetics of light emission immediately after rapid mixing of the luciferase and substrate. X-axis, time (seconds); Y-axis, Counts per second (cps).
Figure 7B:
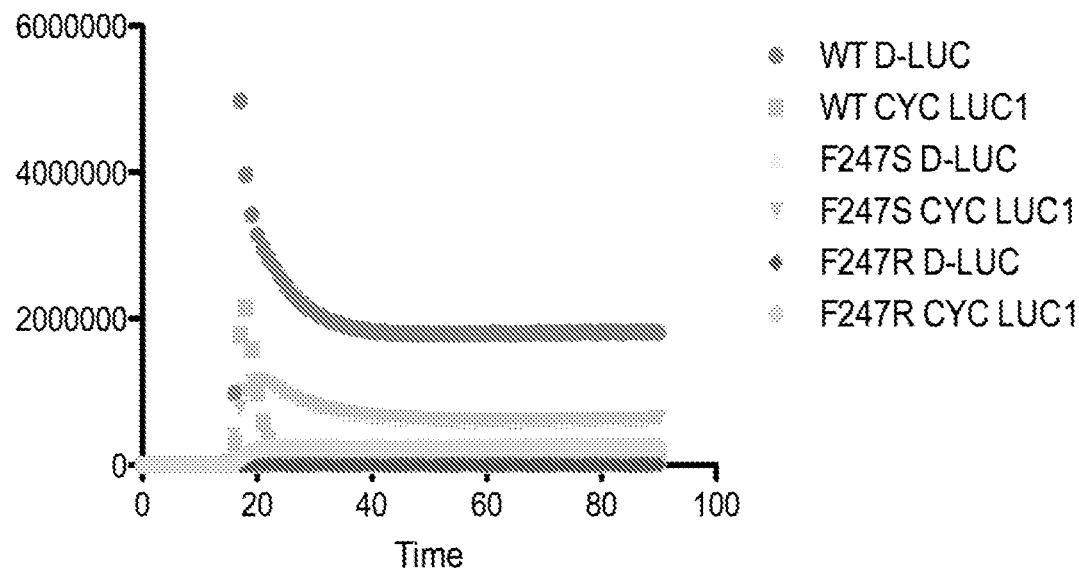
Figure 7C:
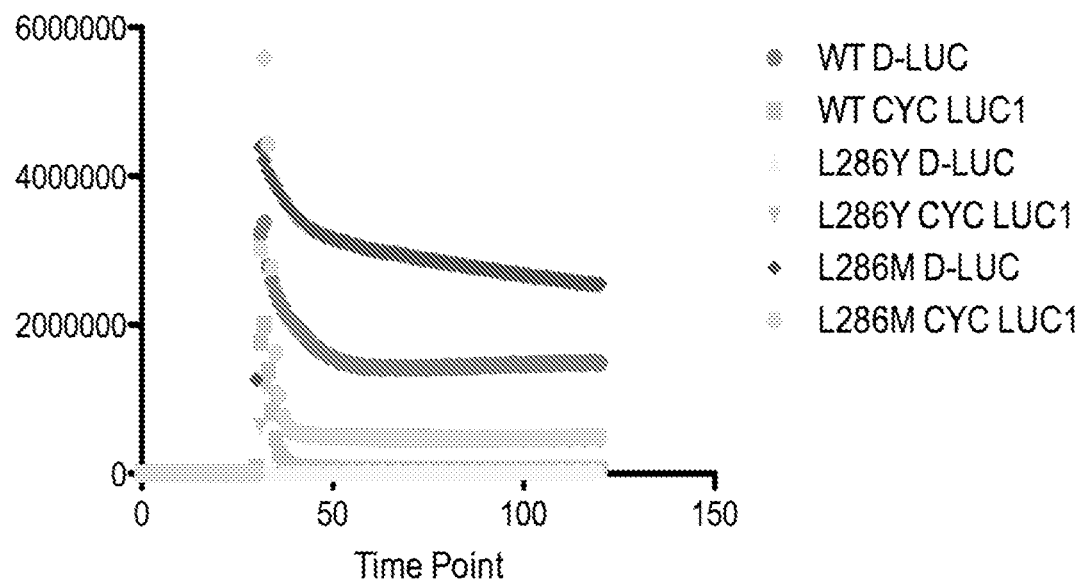
Figure 7D:
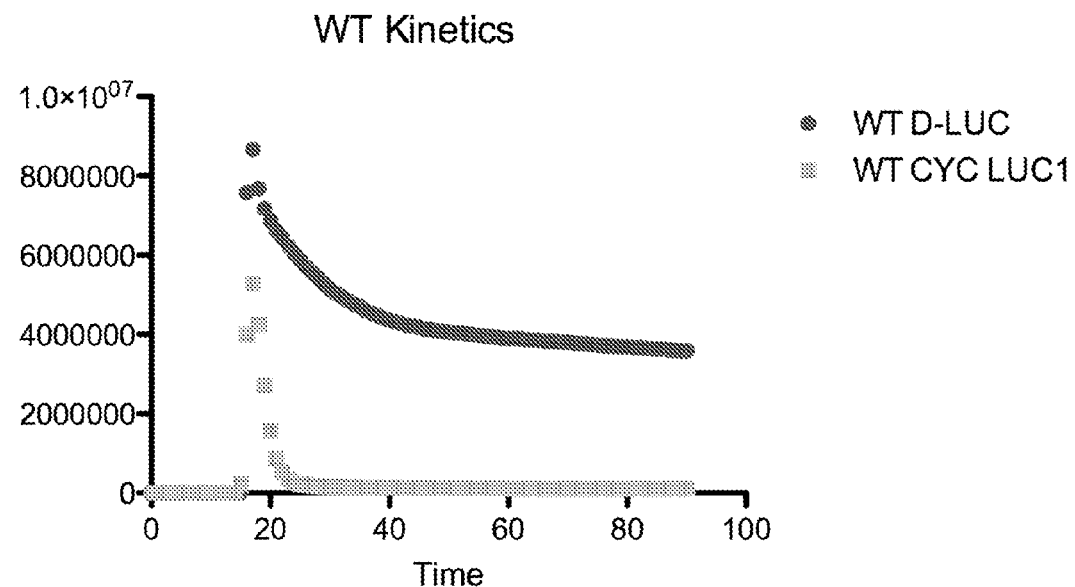
Figure 7E:
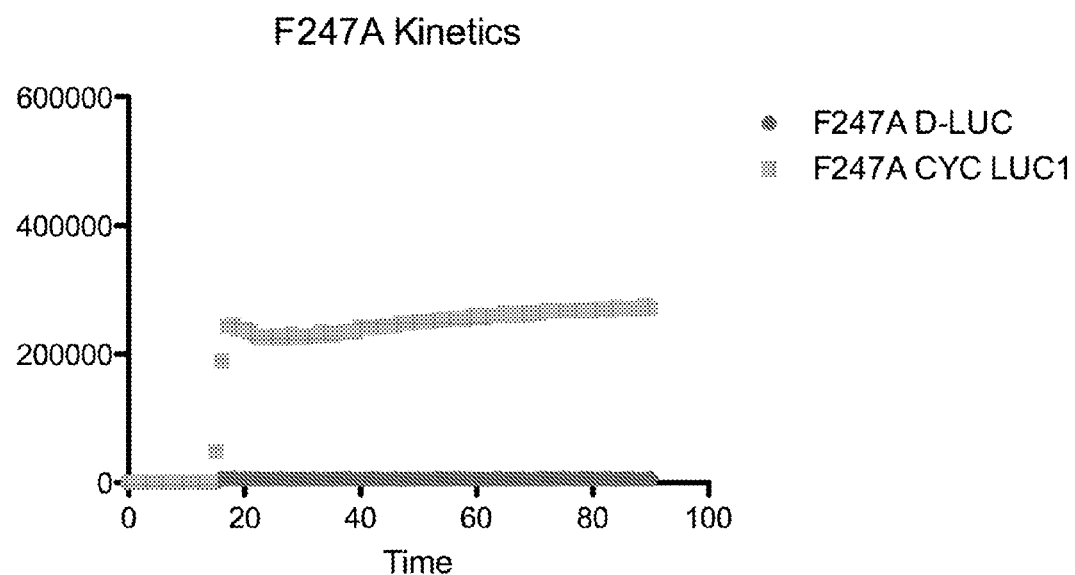
Figure 7F:
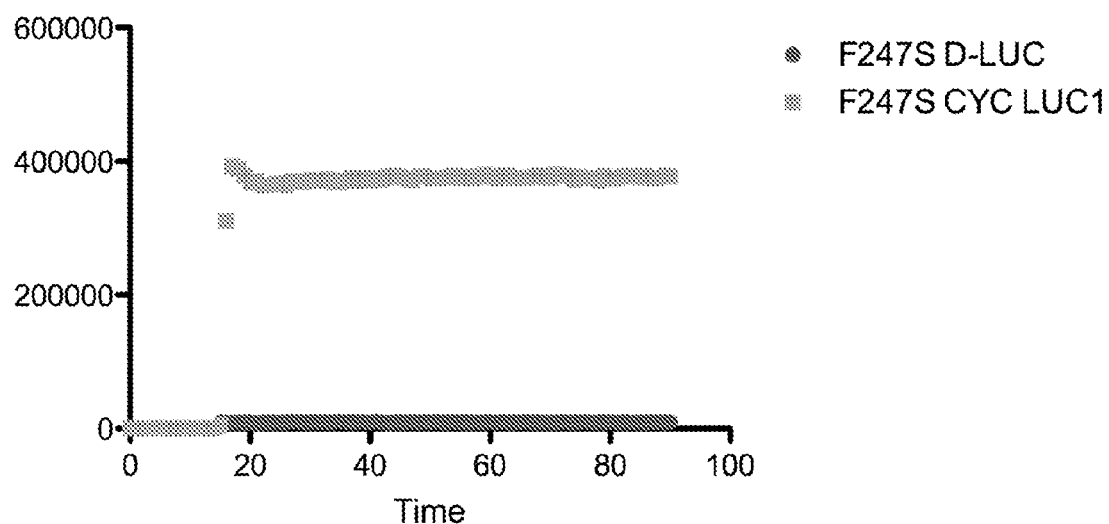
Figure 7G:
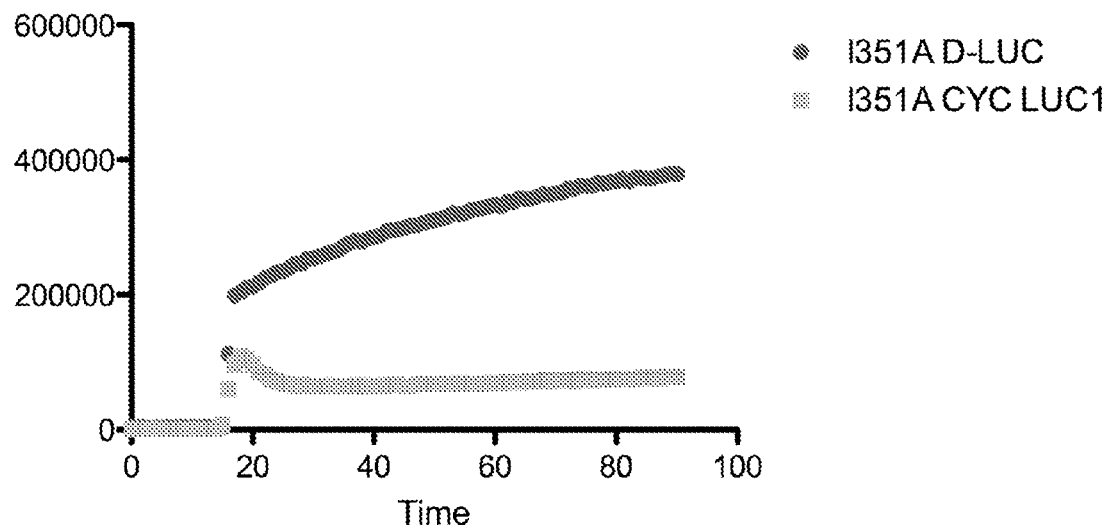
Figure 7H:
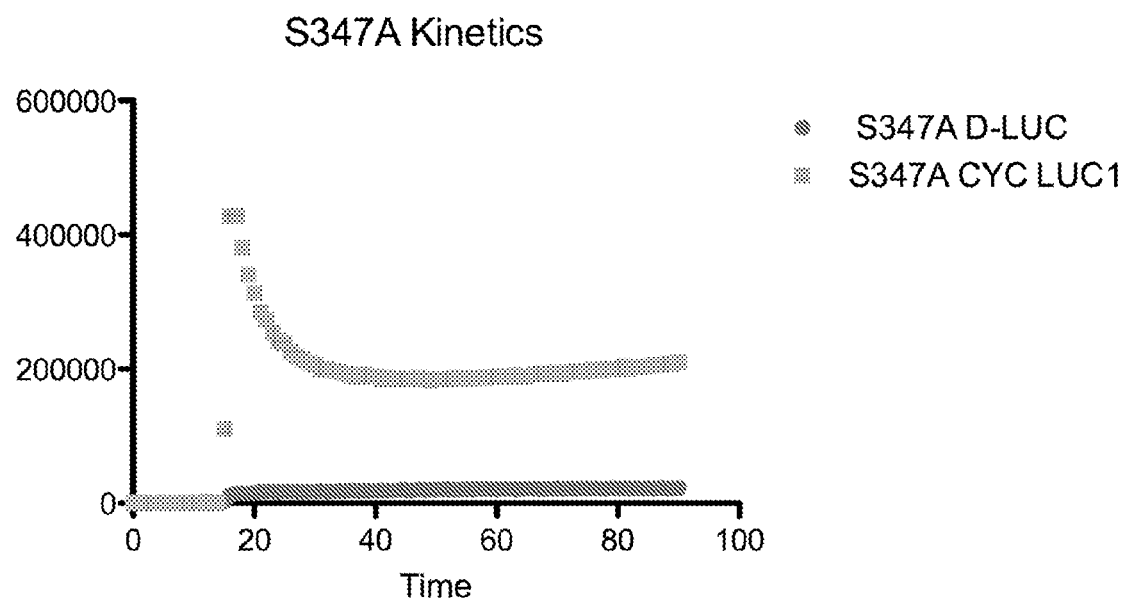
Figure 7I:
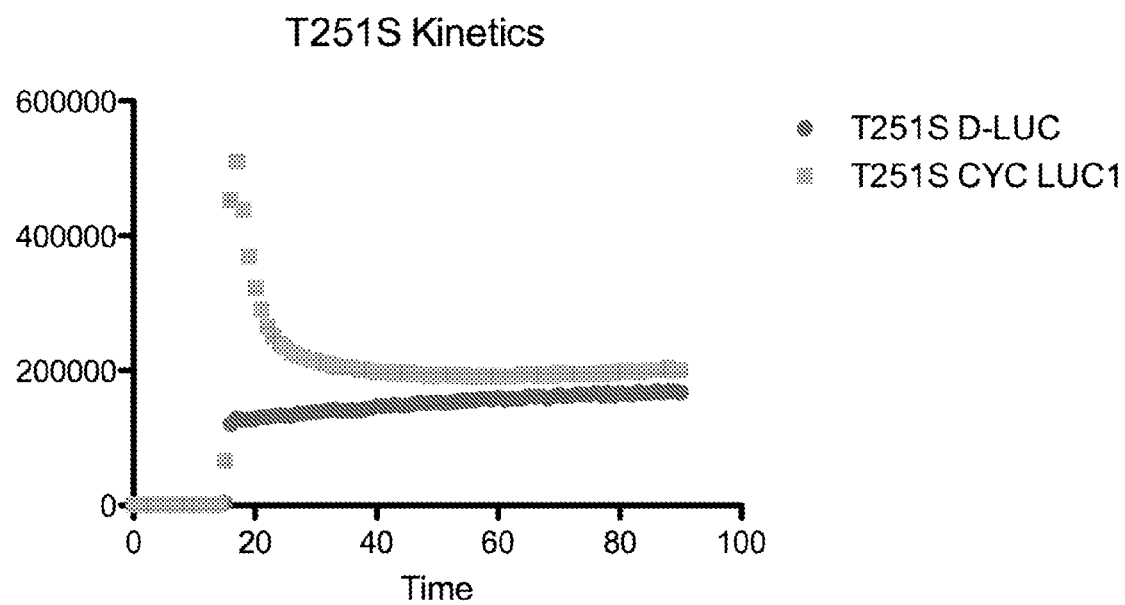
Figure 8A:
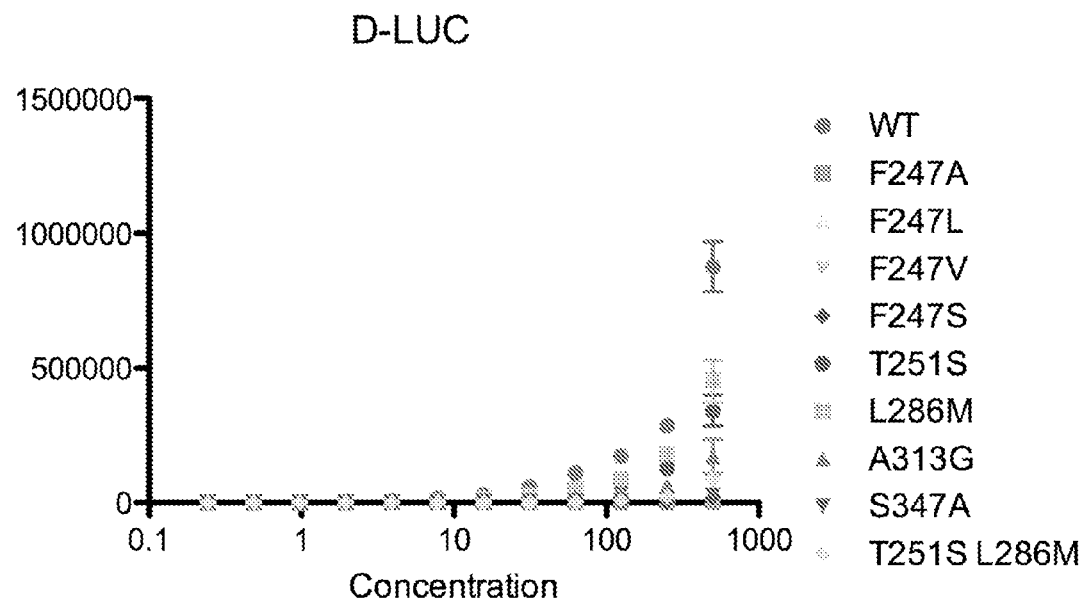
FIGS. 8A-F are line graphs showing the results of experiments done in CHO cells. 8A-B, experiments in intact CHO cells. 8C-D, showing only the three mutants with the highest light output in live CHO cells with CYCLUC1. 8E-F, experiments in lysed CHO cells. X-axis, µM substrate; Y-axis, Counts per second (cps). Photons were counted using a Turner Veritas luminometer. Curves were produced by curve fitting of the data with the Michaelis-Menten equation using GraphPad Prism 5.0.
Figure 8B:
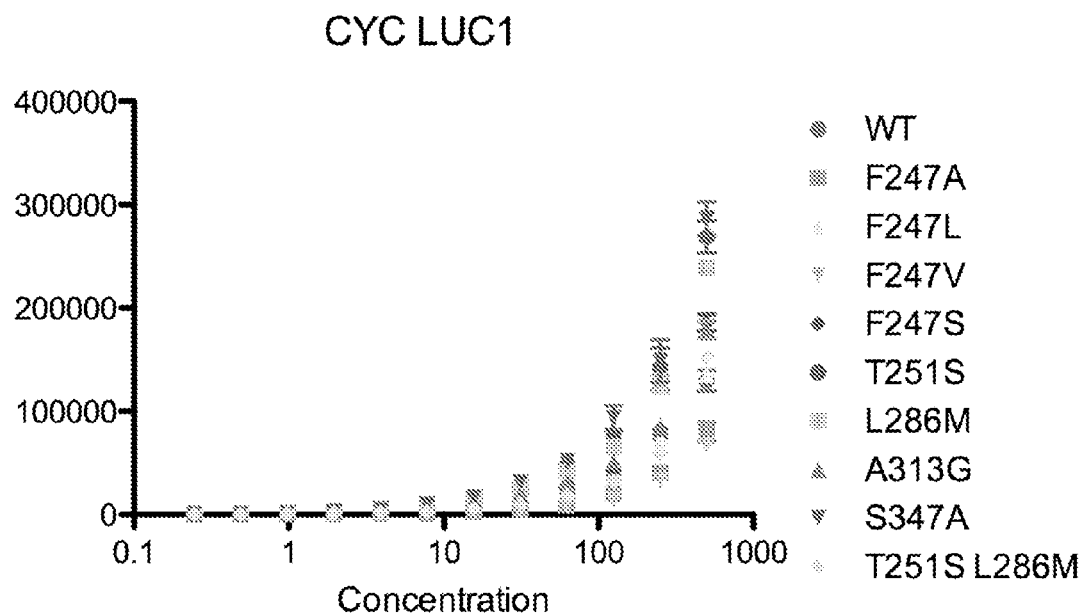
Figure 8C:
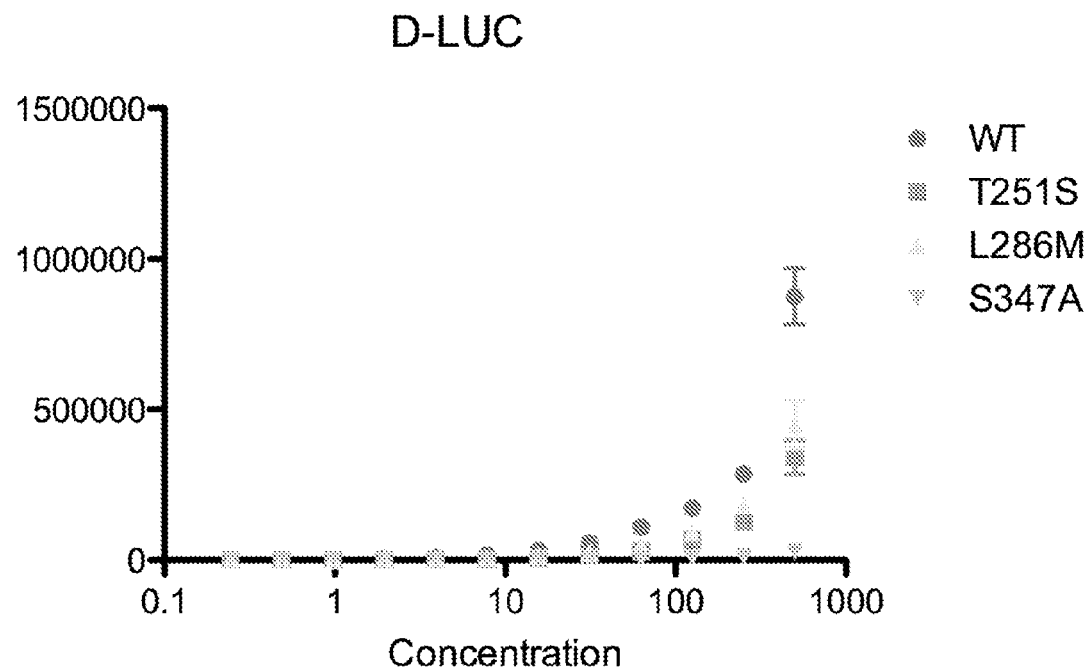
Figure 8D:
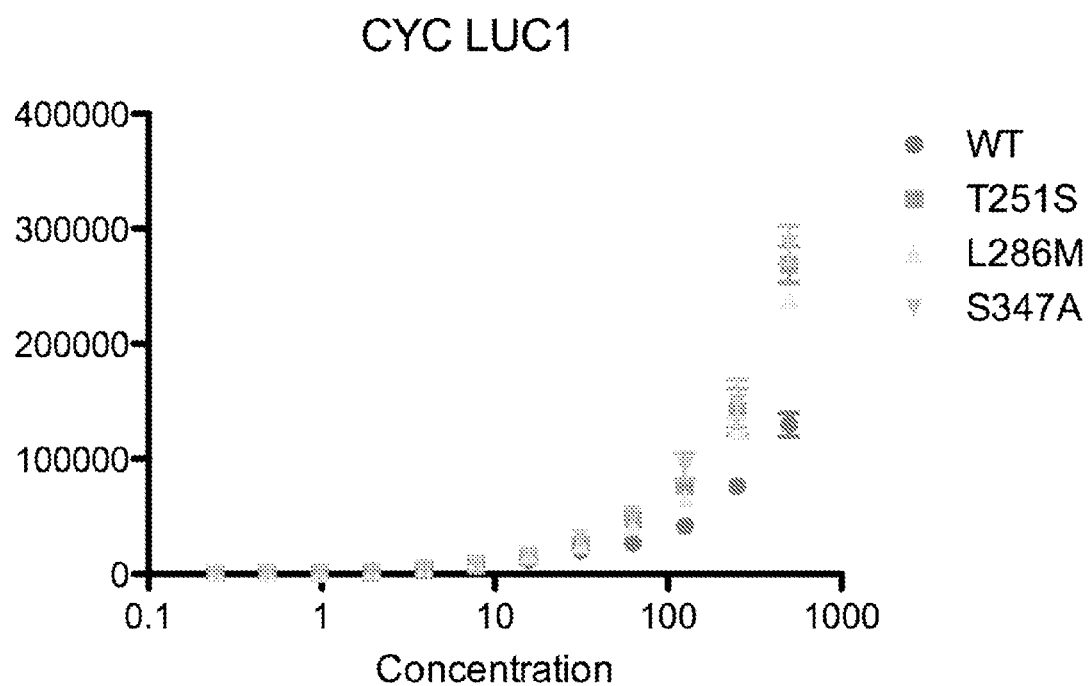
Figure 8E:
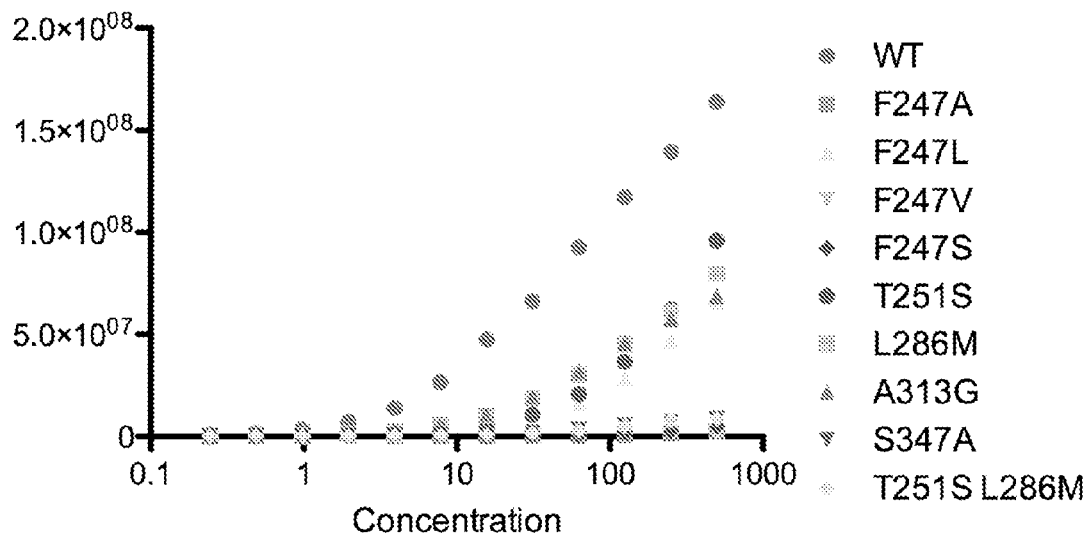
Figure 8F:
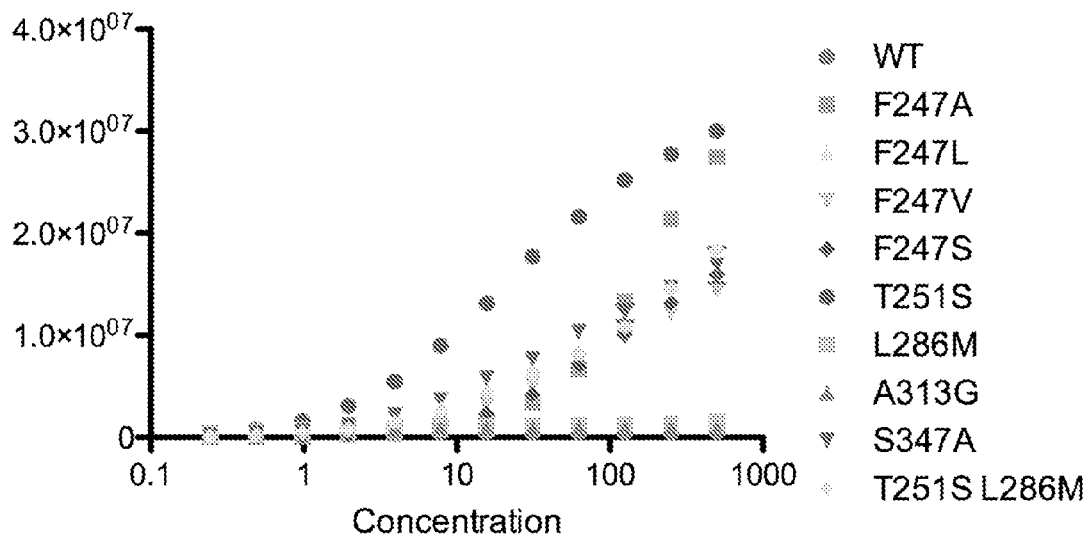

Surprisingly, the F247L mutation improves maximal sustained light emission from 6'-aminoluciferin by 4.9-fold but has only a small positive effect on light emission from CycLuc1 (FIG. 2A, 4B). Instead, the F247A mutation, which has a marked negative effect on light output from both D-luciferin and 6'-aminoluciferin, gave dramatically improved sustained light output from CycLuc1 (FIG. 4B). The improved light output of this mutant comes at the cost of a substantially increased $K_m$ value. While this is not a concern under conditions where saturating concentrations of substrate can be applied (e.g., in vitro), a high $K_m$ is expected to limit light output in live cells where only low intracellular concentrations of luciferin substrates are achieved (de Wet et al., Mol Cell Biol 7, 725-737, 1987; Craig et al., Biochem. J 276 (Pt 3), 637-641, 1991; Shinde et al., Biochemistry 45, 11103-12, 2006). Therefore alternate sites for mutation were sought that could potentially increase light output yet retain a low $K_m$.

The following experiments were performed to determine whether mutation of residues surrounding the luciferin and ATP binding site could modulate both the substrate preference and the kinetics of light emission. Based on the crystal structure of *Luciola cruciata* luciferase (Nakatsu et al., Nature 440, 372-376, 2006), a number of amino acids were identified that are believed to interact with D-luciferin, ATP, or play a role in creating the overall local structure of the binding pocket. Residues within 6 Å of the 6'-hydroxyl of D-luciferin based on the crystal structure of Japanese firefly luciferase (but using North American firefly luciferase numbering, which differs by two amino acids) include: F247, T251, I286, A313, S314, G315, R337, Q338, G339, Y340, A348, I351. Within 8 Å: add R218, S347, T352. The following residues were therefore chosen for mutagenesis: Phe247, Leu286, Ser347, Ala313, Thr251, Ile351, Arg218, Arg337, Asn231, Glu313, Gln338, Ala348.

Sites Phe247, Leu286, Gln338, Ala313, Ile351, Arg218, and Thr251 were mutated with degenerate primers to all 20 amino acids. These mutant luciferases were expressed from the pGEX6P-1 vector in JM101 cells and screened for luciferase light emission from different aminoluciferin substrates. The following point mutants were also made: S347A, R337A, L286A, A313G, F247L, F247A, I351A, A348G.

Within 10 Å of the 6'-hydroxyl or 4'-carbon of D-luciferin include residues in the following peptide sequences: Arg218-Asn231; Ser239-Tyr255; Ser284-Val288; Glu311-Gly316; Arg337-Thr352; Val362-Val366; Met396 (denoted by boxes on FIG. 9). These residues are all therefore candidates for mutation to improve the properties of aminoluciferin and other D-luciferin analog substrates.

Plasmid construction, mutant creation and screening, protein expression and purification were carried out as follows.

Plasmid Constructs.

The full firefly (*Photinus pyralis*) luciferase gene was PCR amplified from pGL3 (Promega). The PCR product was cloned into the BamH1 and NotI sites of pGEX6P-1 for bacterial expression. Mutant proteins were created using the Quickchange site-directed mutagenesis kit (Stratagene). Saturating mutagenesis was performed using the used the degenerate codon NNK at sites predicted to impact or alter substrate biding including F247, T251, L286, S347, R337, R218, Q338, Y340, A313, and I351 using the degenerate codon NNK. The point mutants S347A, L286A, A348G, E311A, I351A, A313G, R337A, H245A and L342A were made independently.

Mutant Screening.

Following saturating mutagenesis, 500 μL of the *E. coli* strain JM109 was transformed and plated on 5 LB plates that contained 50 mg/mL carbenicillin. Colonies were picked and used to inoculate two 96-well plates where each well contained 150 μL of LB with 50 mg/mL carbenicillin. Inoculated plates were incubated at 37° C. overnight. Cells were induced with 0.1 mM IPTG and incubated at RT overnight. Five μL of the bacterial protein extraction reagent SoluLyse (Genlantis) was then added to 50 μL of induced cells followed by a 10-minute incubation at RT. Two μL of each lysate was then added to 60 μL of a solution containing 25 μM substrate in 20 mM Tris pH 7.6, 0.1 mM EDTA, 8 mM MgSO$_4$, 4 mM ATP, and 1 mM TCEP in each well of an untreated non-binding white 96-well plate (Costar). The bioluminescence emission was measured in a Turner Veritas luminometer after a delay of 2-5 minutes. Readings were taken every 30 seconds for a total of 10 runs. Mutants that displayed desired emission profiles with the different substrates tested were sequenced to determine the specific mutation introduced and expressed and purified for further characterization. Desired emission profiles included mutants that displayed the highest light output with the synthetic substrates tested, mutants that showed higher sustained light output over time, and/or mutants that exhibited selectivity for the synthetic substrates tested versus D-Luciferin.

For those lysates that gave improved and/or selective light output with CycLuc1, the plasmid encoding the mutant luciferase was sequenced.

Mutation at some sites failed to produce any obvious improvement in luciferase performance. For example, mutation of tyrosine 340 in the nucleotide binding pocket primarily yielded inactive luciferases.

A secondary assay was also performed on the bacterial extracts to measure light output as a function of substrate, e.g., CycLuc1, concentration. Mutants that demonstrated improved light output, low Km, and/or selectivity for CycLuc1 in this assay were expressed as recombinant proteins and purified for further characterization, as described in Example 2.

Example 2

Titration Assays with Purified Protein and Intact and Lysed Cells

Protein Expression.

The mutants determined to be of interest following the mutant screens, were expressed as GST-fusion proteins from the vector pGEX6P-1 in the *E. coli* strain JM109 as previously described (Bhunia and Miller, Chembiochem 8:1642-1645 (2007)). Cells were grown at 37° C. until the $OD_{600}$ reached 0.5-1, induced with 0.1 mM IPTG, and incubated at 20° C. overnight. Cells were pelleted at 5000 rpm in a Sorvall 2C3C Plus centrifuge (H600A rotor) at 4° C. for 10 minutes, then flash-frozen in liquid nitrogen and purified immediately or stored at −80° C.

Luciferase Purification.

*E. coli* cell pellets from one liter of culture were thawed on ice, resuspended in 25 ml Lysis Buffer (50 mM HEPES pH 7.4, 500 mM NaCl, and 0.5% Tween-20) containing 1 mM PMSF, and disrupted by sonification (Branson Sonifier). Dithiothreitol (DTT) was added at 10 mM and the resulting cell lysate was clarified by centrifugation at 35K rpm in a Beckman 50.2Ti rotor for 30-45 minutes. The supernatant was batch-bound to immobilized glutathione for 1 h at 4° C., and the beads were washed with Lysis Buffer containing 10 mM DTT, followed by Wash Buffer (50 mM Tris pH 8.1, 250 mM NaCl and 10 mM DTT), and finally with Storage Buffer (50 mM Tris pH 7.4, 150 mM NaCl, 1 mM TCEP). Twenty units of PreScission Protease (GE Healthcare) were added and incubation continued overnight at 4° C. to cleave the GST-fusion and elute the untagged luciferase protein.

Titration Assays with Purified Protein.

Luminescence assays in 96-well plates were initiated by adding 30 μL 2× substrate in 20 mM Tris pH 7.6, 0.1 mM EDTA, 8 mM $MgSO_4$, 4 mM ATP, and 1 mM TCEP to 30 μL of 20 nM purified luciferase in 20 mM Tris pH 7.6, 0.1 mM EDTA, 1 mM TCEP and 0.4 mg/mL BSA. Titration assays were performed 3 minutes post-substrate addition in a Turner Veritas luminometer with final substrate concentrations ranging from 0.122-250 μM or 0.244-500 μM.

Transfections.

The mutants were cloned into the BamHI-Not I site of pcDNA 3.1 and transfected into CHO cells for live and lysed cell experiments. CHO-cell transfections were performed using Lipofectamine 2000 in 96-well white tissue culture treated plates (Costar) for intact cell assays, or 6-well plates for lysed cell assays. For intact cells, 0.075 μg DNA/well was transfected. For lysed cells, 2.25 μg DNA/well was transfected and one full 6-well plate was transfected for each mutant. Assays were performed in triplicate 24 hours post-transfection.

Intact Cell Assays.

Transfected CHO cells were washed with HBSS and overlaid with 60 μL substrate in HBSS. Titration assays were performed 3 minutes post-substrate addition in a Turner Veritas luminometer with final substrate concentrations ranging from 0.122-250 μM or 0.244-500 μM.

Lysed Cell Assays.

Transfected CHO cells were washed with HBSS and lysed for 10 minutes at RT with 1 mL 1× Passive Lysis Buffer (Promega) per well. Luminescence assays were initiated by adding 30 μL 2× substrate in 20 mM Tris pH 7.6, 0.1 mM EDTA, 8 mM $MgSO_4$, 4 mM ATP, 6 mg/mL BSA, 25 μM CoenzymeA and 33 mM DTT to 30 μL of lysate in a non-binding untreated white 96-well plate (Costar). Titration assays were performed 3 minutes post-substrate addition in a Turner Veritas luminometer with final substrate concentrations ranging from 0.122-250 μM or 0.244-500 μM.

Results.

For most of the luciferase mutants, the rank of light output was D-Luc>CycLuc1>6'-NH2LH2>6'-MeNHLH2>CycLuc2>6'-Me2NLH2. In most cases, the aminoluciferins exhibited much lower Km values than D-luciferin. The R218K mutant was the most generally beneficial mutation, yielding the greatest light output for most aminoluciferin substrates, including a 20-fold improvement in the maximal sustained emission from CycLuc2 while retaining a very low Km of 0.3 μM (FIGS. 2C, 3B, 3C, 4A-4E). Similarly, the maximal sustained light emission from CycLuc1 was increased 14-fold to 12.5% of that of D-luciferin with WT luciferase, yet at a Km of 1.8 μM that is still substantially lower than that of D-luciferin. The R218K mutation has been previously described in the context of D-luciferin, and is known to raise the Km but cause minimal disruption of catalytic activity (Branchini et al., Biochemistry 40, 2410-2418, 2001).

Table 1 lists candidates identified by screening and assayed as purified proteins in titration experiments. Those in bold were identified as having particularly beneficial effects with modified luciferin analogs.

TABLE 1

| IDENTIFIED IN SATURATING MUTAGENESIS SCREEN | POINT MUTATIONS | DOUBLE MUTANTS | TRIPLE MUTANTS | QUADRUPLE MUTANT |
|---|---|---|---|---|
| F247A | L286A | S347A + L286M | T251S + L286M + S347A | R218K + L286M + S347A + L342A |
| F247L | S347A | S347A + T251S | F247L + S347A + T251S | |
| F247V | A348G | S347A + F247V | F247L + S347A + L286M | |
| F247S | E311A | S347A + F247S | F247L + T251S + L286M | |
| F247R | I351A | S347A + F247L | R218K + T251S + S347H | |
| T251N | R337A | F247L + L286M | R218K + L286M + S347A | |
| T251Q | H245A | F247S + T251S | | |
| T251V | L342A | T251S + L286M | | |
| T251I | | F247L + T251S | | |
| T251S | | A313G + F247L | | |
| L286T | | R218K + T251S | | |
| L286Y | | R218K + S347A | | |
| L286S | | R218K + T251M | | |
| L286M | | R218K + L286M | | |
| S347C | | R218K + T251E | | |
| S347T | | R218K + T251Q | | |
| Q338W | | R218K + F247L | | |

TABLE 1-continued

| IDENTIFIED IN SATURATING MUTAGENESIS SCREEN | POINT MUTATIONS | DOUBLE MUTANTS | TRIPLE MUTANTS | QUADRUPLE MUTANT |
|---|---|---|---|---|
| R218K | | H245A + L342A | | |
| R218V | | R218K + F247Q | | |
| R218Y | | R218K + F247T | | |
| R218S | | L286M + T251S | | |
| R218T | | L286M + S347A | | |
| A313F | | R218K + L342A | | |
| A313N | | L286M + L342A | | |
| A313L | | | | |
| A313G | | | | |

Improved single point mutants identified by screening include Q338W; R218K; L342A; R218V; R218Y; R218S; R218T; S347A; T251S; F247S; F247V; L286M; A313N; A313F; A313L; and A313G, with R218K and L342A providing the best results. The R218K mutation (FIG. 2C) shows increased light emission from all luciferin analogs tested and has served as a benchmark for continued improvement of the modified substrates. Other point mutations (FIGS. 2A-B and 2D-H) can have varying effects on selectivity of luciferin analogs over D-luciferin. S347A and Q338W prefer CycLuc1 over D-luciferin, A313N improves aminoluciferin, especially at low concentrations, and L342A behaves much like R218K and generally improves all luciferin analogs tested. Mutations at 247 relieve product inhibition in vitro, but generally give lower light output in live cells. This behavior is likely due to higher Km values for both luciferin and ATP. Interestingly, F247L and A313G both give better performance with 6'-aminoluciferin than the wild-type enzyme. The L286M, S347A, and T251S mutant luciferases improved light output with synthetic alkylaminoluciferins, especially in live cells.

Luciferin performance was evaluated based on several factors: 1) Km; 2) product inhibition; 3) quantum yield of light emission; 4) Vmax—kinetic components; and 5) cell permeability. At low concentrations, the low Km and efficient light output of CycLuc1 outperformed both D-luciferin and NH2-luciferin even with wild-type luciferase. At higher concentrations, product inhibition was more severe, and the relative performance dropped. Mutation of luciferase (e.g., F247L, L286M, T251 S) can significantly improve the performance of CycLuc1 and NH2-luciferin relative to the wild-type enzyme.

For the F247 mutants, the phenylalanine residue makes π-stacking interactions with the luciferin. Mutation to A, S, V, or L removed this interaction. Interestingly, F247L was still an efficient light emitter with D-luciferin, and exhibited improved properties with 6'-aminoluciferin. However, alkylaminoluciferins still resulted in some product inhibition.

On the other hand, mutation to A, S, or V leads to a luciferase that operated efficiently with synthetic alkylaminoluciferins, and exhibited poor light emission with D-luciferin and aminoluciferin. Branchini et al. (Biochemistry. 2001 Feb. 27; 40(8):2410-8, and Biochemistry. 2003 Sep. 9; 42(35):10429-36) previously characterized F247L, F247A, R218K, S347A, and I351A with D-luciferin, and found that the leucine mutation had little effect on Km or Vmax. On the other hand, F247A had substantially lower affinity for both D-luciferin and ATP, as well as an impaired catalytic rate. F247A binds alkylaminoluciferins with much higher affinity than D-luciferin, and is therefore still capable of emitting light with these substrates.

Figure 11B:
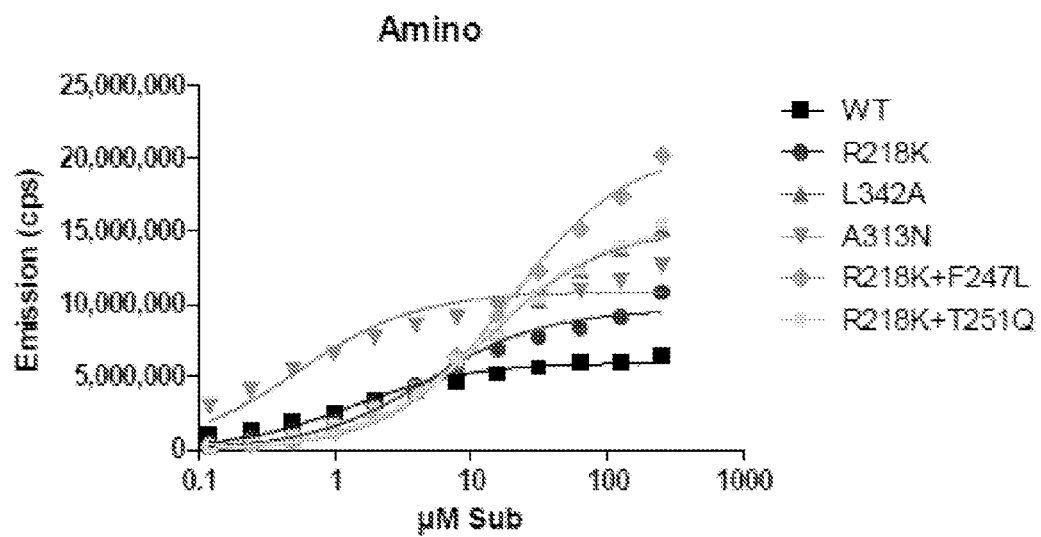

Some mutations, such as A313N (FIGS. 11A-B), improved light emission with aminoluciferin. This improvement has direct application for use in bioluminescent protease assays, where aminoluciferin is released upon activity of the protease of interest.

| Apparent Km Values (µM) | | | | | | |
|---|---|---|---|---|---|---|
| | D-Luciferin | 6'-NH$_2$LH$_2$ | 6'-MeNHLH$_2$ | 6'-Me$_2$NLH$_2$ | CycLuc1 | CycLuc2 |
| WT | 6.76 ± 0.3 | 0.78 ± 0.03 | 0.06 ± 0.004 | 0.025 ± 0.003 | 0.10 ± 0.01 | NA |
| T251S | 114 ± 3.4 | 17.3 ± 0.3 | 0.27 ± 0.02 | 0.30 ± 0.02 | 1.83 ± 0.09 | 0.13 ± 0.02 |
| L286M | 19.1 ± 1.3 | 4.35 ± 0.2 | 0.08 ± 0.005 | 0.08 ± 0.005 | 0.46 ± 0.03 | 0.10 ± 0.01 |
| S347A | 76.6 ± 3.1 | 31.0 ± 0.4 | 0.47 ± 0.03 | 0.24 ± 0.014 | 2.68 ± 0.07 | 0.11 ± 0.005 |
| R218K | 106 ± 2.6 | 15.2 ± 1.1 | 0.45 ± 0.04 | 0.35 ± 0.04 | 1.79 ± 0.12 | 0.27 ± 0.02 |

| Apparent Vmax Values (×10$^{-5}$ cps) | | | | | | |
|---|---|---|---|---|---|---|
| | D-Luciferin | 6'-NH$_2$LH$_2$ | 6'-MeNHLH$_2$ | 6'-Me$_2$NLH$_2$ | CycLuc1 | CycLuc2 |
| WT | 1079 ± 13 | 35 ± 0.25 | 3 ± 0.02 | 0.5 ± 0.003 | 9.7 ± 0.1 | 1.3 ± 0.02 |
| T251S | 1054 ± 19 | 51 ± 0.3 | 8 ± 0.1 | 1.6 ± 0.02 | 90 ± 0.9 | 4.8 ± 0.1 |
| L286M | 1060 ± 26 | 62 ± 0.7 | 7 ± 0.05 | 1.3 ± 0.01 | 60 ± 0.7 | 2.3 ± 0.02 |
| S347A | 142.8 ± 3 | 91 ± 0.4 | 16 ± 0.2 | 2.1 ± 0.02 | 135 ± 0.8 | 7.6 ± 0.05 |
| R218K | 1541 ± 21 | 157 ± 3.7 | 38 ± 0.5 | 5 ± 0.1 | 134 ± 1.9 | 26 ± 0.3 |

Mutation of phenylalanine 247 to serine or valine also relieves product inhibition like F247A, but has less deleterious effects on the overall catalytic function. The higher Km for luciferin (and presumably ATP) gives lower light output in live cells, but allows high light output when high luciferin and ATP concentrations can be used (in vitro).

The luciferin substrate and ATP bind in adjacent pockets, and the binding of one is quite likely to affect the binding of the other (allostery). Indeed, alkylaminoluciferin substrates change the Km of luciferase for ATP. Furthermore, it is apparent from the crystal structure of luciferase that the adenosine pocket covers the luciferin binding pocket, suggesting a sequential order of addition: luciferin first, then ATP; once catalysis is over, AMP must dissociate prior to oxyluciferin release.

Combination of these mutants may be additive, synergistic, or incompatible. Combinations of F247L, F247S, S347A, T251S, L286M, F247V can be made and tested. It is anticipated that one or more combinations of these mutants will have further improved light emission properties with the synthetic luciferin substrates. For example, the double mutant S347A/L286M yields a luciferase that can give sustained light emission with CycLuc1 (20-fold higher Vmax than wt, but higher Km). On the other hand, S347A/F247S and S347A/T251S are only slightly better than wt (somewhat improved Vmax, but worse Km), and S347A/F247V is worse (in both Vmax and Km). All of these mutants display selectivity for CycLuc1 over D-luciferin and aminoluciferin. Some of the double mutants yield superior properties and selectivity: F247L/L286M gives high Vmax for aminoluciferin; F247L/S347A gives highest Vmax for MeNHLH2; L286M/S347A gives high Vmax for CycLuc1 and CycLuc3.

Improved light emission for 6'-aminoluciferin was seen with F247L and A313G, both in vitro and in live cells.

In general, dialkylated substrates gave substantially lower light output than monoalkylated substrates. Improved light emission for dialkylated substrates CycLuc2 and CycLuc4 was seen with R218K, A313F, L342A, and R218K/L342A. R128K and L342A also had efficient light emission with CycLuc1-8', MeNH-LH2, iBuNHLH2, and NH2-LH2.

Further mutation of luciferase divides the resulting enzymes into two classes: those that can still utilize D-luciferin to some extent (FIGS. 2I-2O) and those that cannot (FIG. 2P-2X). Less discriminating mutations, like R218K+L286M, tend to allow for more robust light emission from luciferin analogs, such as CycLuc1. These and others should allow for increased red shifted light emission, with applications for in vivo imaging (see below, last paragraph). More discriminating mutations (e.g., like those shown in FIGS. 2P-2X), allow for the development of orthogonal enzymes that preferentially utilize only certain luciferin analogs, allowing multiplexed bioluminescent imaging. R218K+L286M+S347A, for example, exhibits increased and preferential light emission with CycLuc7, while emitting almost no light at all with D-luciferin (FIGS. 3A-3C, 4A-4E).

In live cells, the best mutants for CycLuc1 included S347A, L286M, and T251S. In lysed cells, the rank of Vmax is T251S>S347A>L286M. These results are consistent with an increased role for low Km vs high Vmax in the context of live cells. Among these three mutants, S347A shows selectivity for CycLuc1 over D-luciferin; with L286M and T251S, the Vmax for D-luciferin is similar to wt. For the R218K and T251S mutant luciferases, CycLuc1 light output was superior to D-luciferin at substrate concentrations below ~30 uM. In the case of the S347A mutant, CycLuc1 exceeded the light output of D-luciferin over the entire concentration range. Remarkably, live-cell light emission from CycLuc2 exceeded that of both CycLuc1 and D-luciferin with T251S, S347A, and particularly R218K luciferase over a broad concentration range, despite the relatively poor light output from CycLuc2 in cell lysates (FIGS. 13A-J).

Example 3

Bioluminescence Emission Scans and Kinetic Assays

Purified mutant luciferases were used in bioluminescence emission and burst kinetics scans. Each purified protein in 20 mM Tris pH 7.6, 0.1 mM EDTA, 1 mM TCEP and 0.4 mg/mL BSA was added to 2× substrate in 20 mM Tris pH 7.6, 0.1 mM EDTA, 8 mM MgSO$_4$, 4 mM ATP, and 1 mM TCEP in a cuvette. Final protein concentrations were 10 nM and substrate concentrations were 1011M.

Bioluminescence Emission Scans.

Luciferase was rapidly injected into a cuvette containing substrate, and the emission from 400-800 nm was recorded in a SPEX FluoroMax-3 fluorimeter with closed excitation slits.

Burst Kinetic Assays.

Measurements were taken in a FluoroMax-3 fluorimeter every second with a 0.1 second integration time at the maximal emission wavelength for each luciferase/substrate pair. Ten seconds after commencing the assay, protein was rapidly injected into the cuvette containing substrate to observe both the burst and the steady-state light emission over the first minute.

Small Molecule Luciferase Inhibition Assays

Luminescence assays in 96-well plates were initiated by adding 30 μL 2× luciferin substrate in 20 mM Tris pH 7.4, 0.1 mM EDTA, 8 mM MgSO$_4$, 4 mM ATP, and 1 mM TCEP to 30 μL of 20 nM purified luciferase in 20 mM Tris pH 7.4, 0.1 mM EDTA, 1 mM TCEP and 0.4 mg/mL BSA. Substrate titration assays were performed 3 minutes post-substrate addition in a Turner Veritas luminometer with final substrate concentrations ranging from 0.122-250 μM in the presence of 0 μM, 1 μM, or 10 μM of the luciferase inhibitor 2-(4-methoxyphenyl)benzothiazole. Enzyme titration assays were performed under the same conditions, using 0 μM, 2 or 20 μM of the luciferase inhibitor 2-(4-methoxyphenyl)benzothiazole, a constant final luciferin substrate concentration of 20 μM, and serial 2-fold dilutions of luciferase concentration from 20 nM down to 0.01 nM.

Results.

The results are shown in FIGS. 7A-I (burst kinetics) and Tables 2-3 (red-shift). As was observed for the wild-type protein, most alkylaminoluciferin substrates gave a rapid initial burst of light, followed by a substantial decrease in the rate of light output (Reddy et al., 2010). Most of the mutant luciferases identified here shared this general behavior, although the decrease in the rate of light output was less severe than that of the wild-type protein, resulting in a higher level of sustained light emission. The most striking finding was that the initial rate of light output for the dialkylaminoluciferin CycLuc2 with the mutant R218K is considerably increased relative to the wild-type protein. In contrast, the burst kinetic profile for the corresponding acyclic dialkylaminoluciferin 6'-Me2N-LH2 was largely unchanged.

The combination of luciferin analogs and mutation of luciferase can further red-shift light emission (Tables 2-3), with the potential for deeper tissue penetration and higher sensitivity for in vivo bioluminescent imaging assays. For example, the R218K mutation results in a red-shift in the emission wavelength for all luciferin analogs, either alone or in combination with other mutations; for the single mutant, D-luciferin yields maximal emission at 567 nm, CycLuc1 at 609 nm, and CycLuc2 at 621 nm. In contrast, the L286M mutant results in a 5-13 nm blue-shift in the emission of all aminoluciferins, but a diametrically-opposed 13 nm red-shift in D-luciferin light emission. Interestingly, the S347A mutant gives discrete emission peaks for all of the aminoluciferins, but anomalous bimodal emission for D-luciferin (Branchini et al., 2003).

TABLE 2

| Substrate | Luciferase | Wavelength at Max. Emission Data for Those Tested: |
|---|---|---|
| D-LUCIFERIN | WT | 554 nm |
| | S347T | 561 |
| | S347A | 573 |
| | T251S L286M | 563 |
| | F247L L286M | 570 |
| | I351A | 570 |
| | T251S | 553 |
| | T251N | 555 |
| | T251Q | 626 |
| | F247S | 588 |
| | F247A | 591 |
| | F247R | 605 |
| | F247V | 600 |
| | L286Y | 606 |
| | L286M | 564 |
| AMINOLUCIFERIN | WT | 595 nm |
| | S347T | 583 |
| | S347A | 591 |
| | T251S L286M | 602 |
| | F247L L286M | 592 |
| CYCLUC1 | WT | 601 nm |
| | S347T | 601 |
| | S347A | 597 |
| | T251S L286M | 601 |
| | F247L L286M | 603 |
| | I351A | 604 |
| | T251S | 602 |
| | T251N | 604 |
| | T251Q | 612 |
| | F247S | 607 |
| | F247A | 605 |
| | F247R | 609 |
| | F247V | 603 |
| | L286Y | 604 |
| | L286M | 591 |
| CYCLUC3 | WT | 594 nm |
| | F247V | 599 |
| | L286M | 592 |

TABLE 3

Maximum Emission Wavelength of Selected Substrate

| | WT | R218K | L286M + S347A | L342A | R218K + L342A |
|---|---|---|---|---|---|
| D-Luc | 551 | 565 | 561 | 551 | 561 |
| Aminoluc | 594 | 599 | 589 | 591 | 594 |
| Monomethyl | 608 | 610 | 599 | 611 | 612 |
| Dimethyl | 619 | 624 | 608 | 619 | 628 |
| Isobutyl | 606 | 615 | 598 | 606 | 618 |
| Propanol | 608 | 609 | 593 | 607 | 609 |
| Cyc1 | 601 | 605 | 595 | 597 | 604 |
| Cyc2 | 609 | 619 | 608 | 611 | 617 |
| Cyc3 | 599 | 605 | 590 | 599 | 606 |
| Cyc4 | 607 | 617 | 602 | 608 | 616 |
| Cyc5 | 637 | 635 | 631 | 631 | 633 |
| Cyc6 | 636 | 637 | 628 | 639 | 635 |
| Cyc7 | 607 | 620 | 604 | 611 | 616 |
| Cyc8 | 610 | 632 | 605 | 614 | 628 |
| Cyc9 | 624 | 636 | 615 | 608 | 617 |
| Cyc10 | 642 | 645 | 635 | 639 | 641 |

Figure 12A:
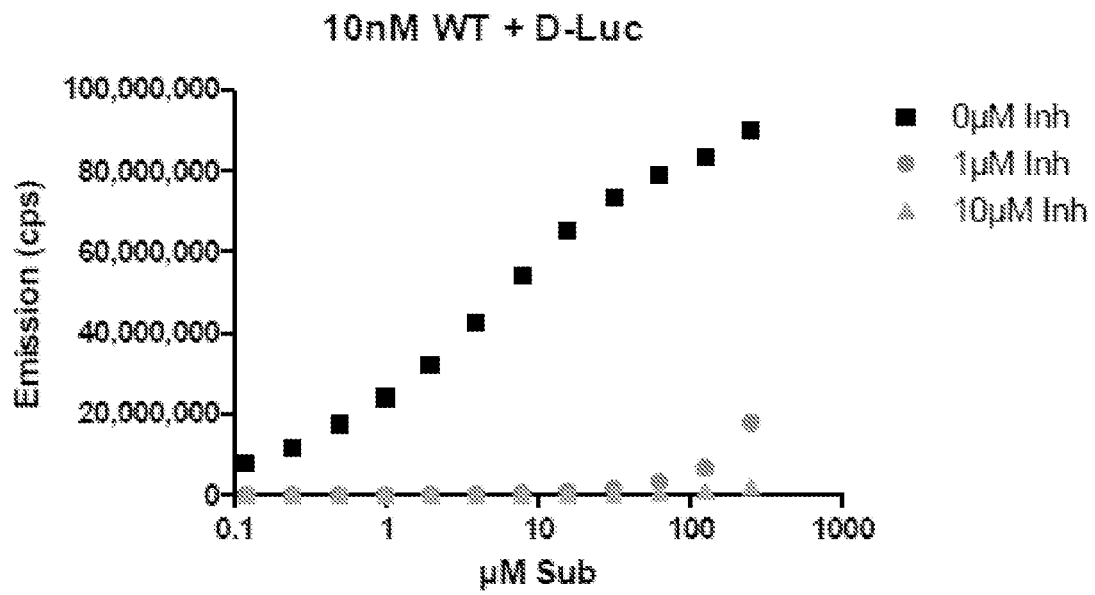
FIGS. 12A-H are line graphs showing that the mutants have improved bioluminescence resistant to inhibition by small molecules.
Figure 12B:
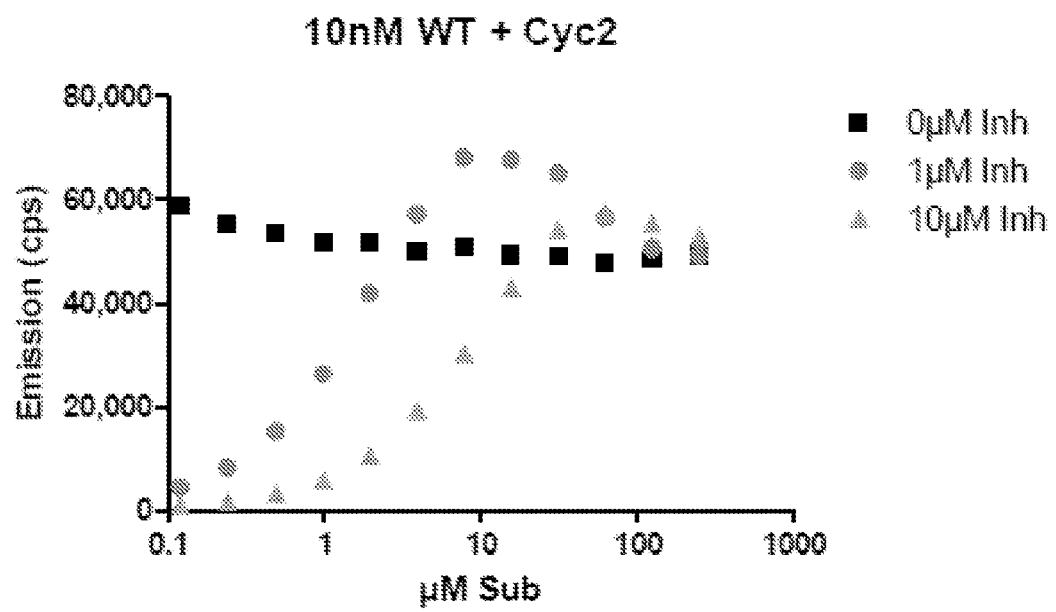
Figure 12C:
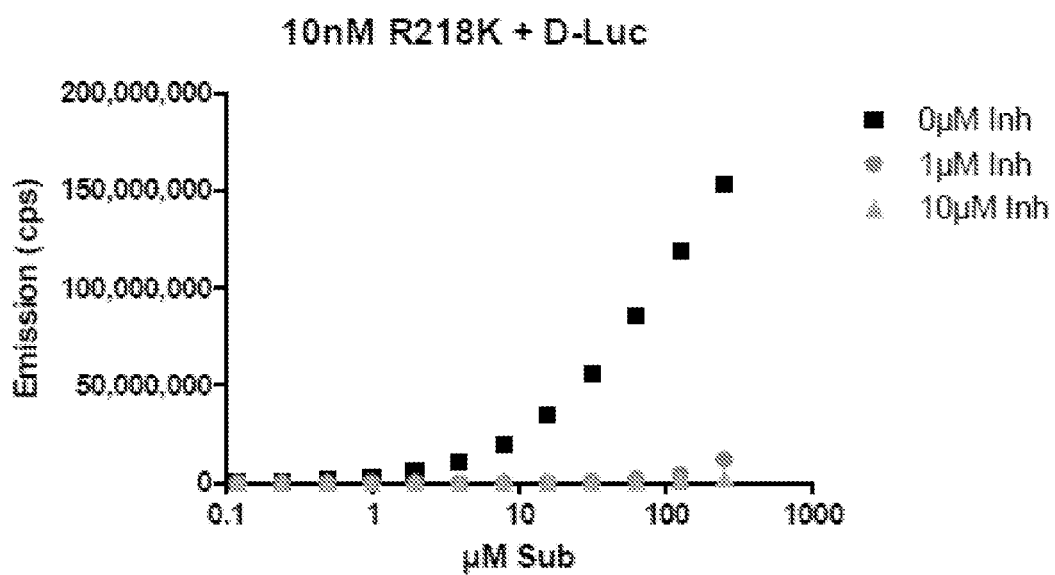
Figure 12D:
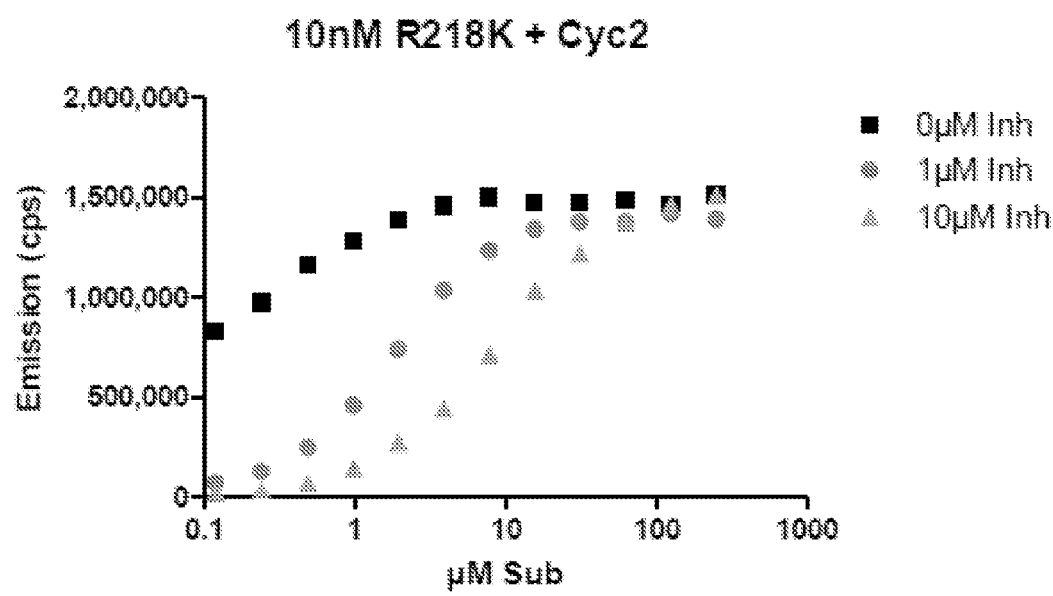
Figure 12E:
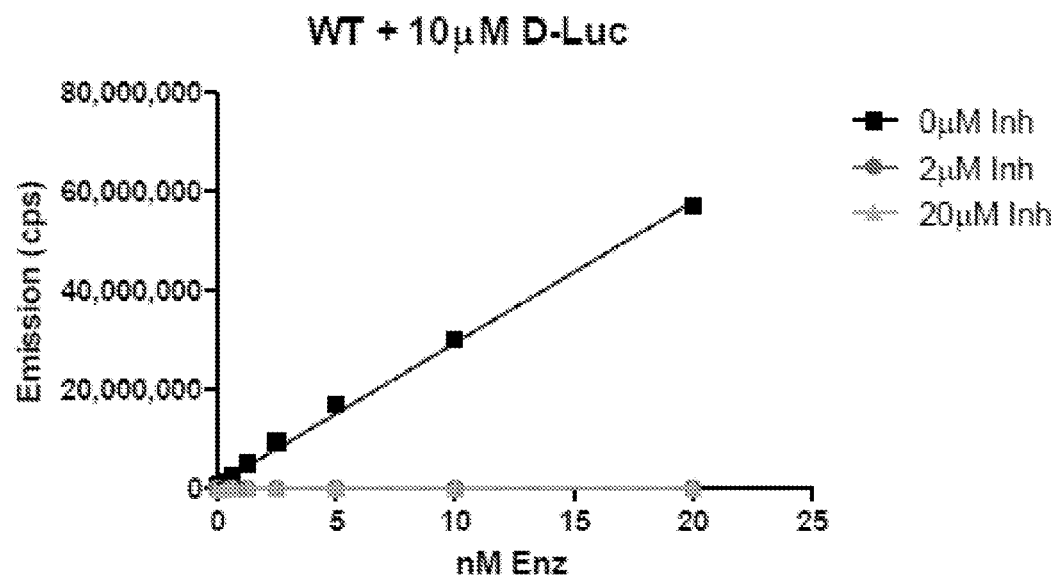
Figure 12F:
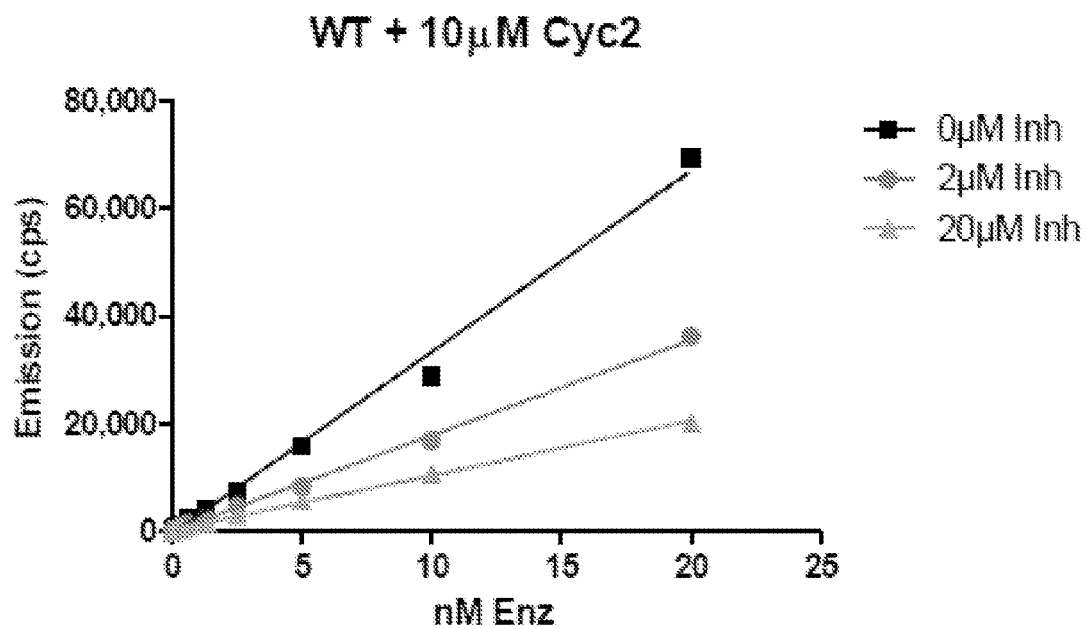
Figure 12G:
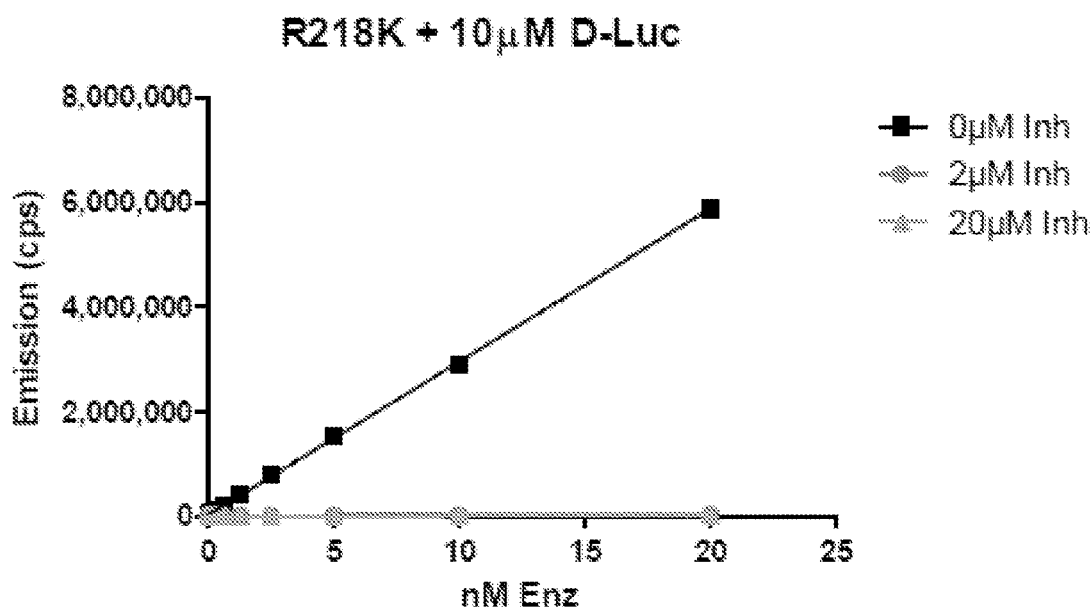
Figure 12H:
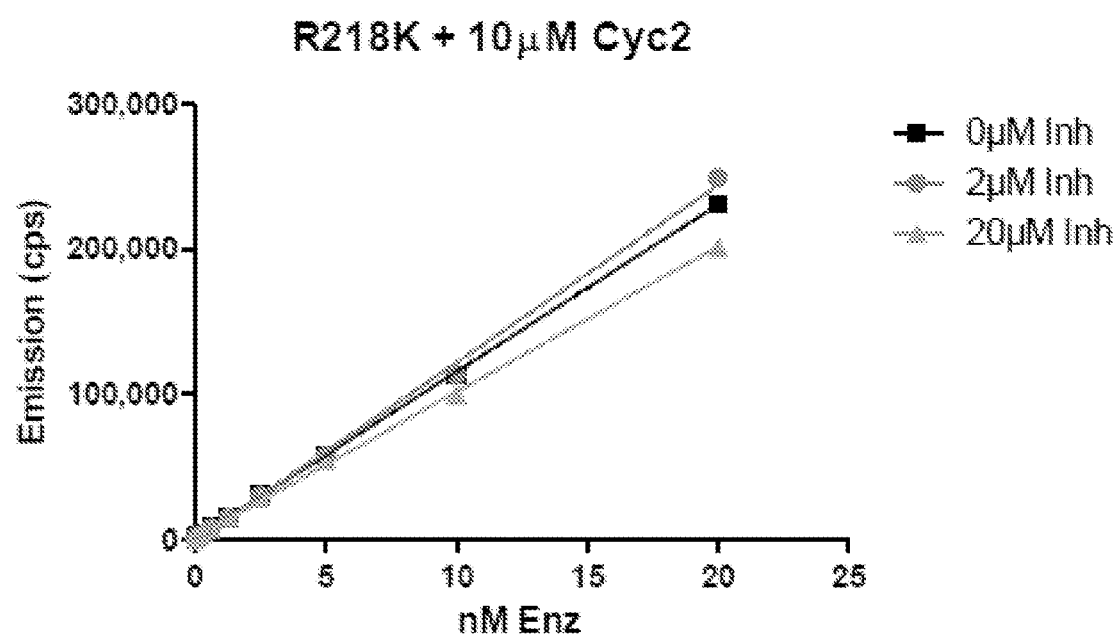
Figure 13A:
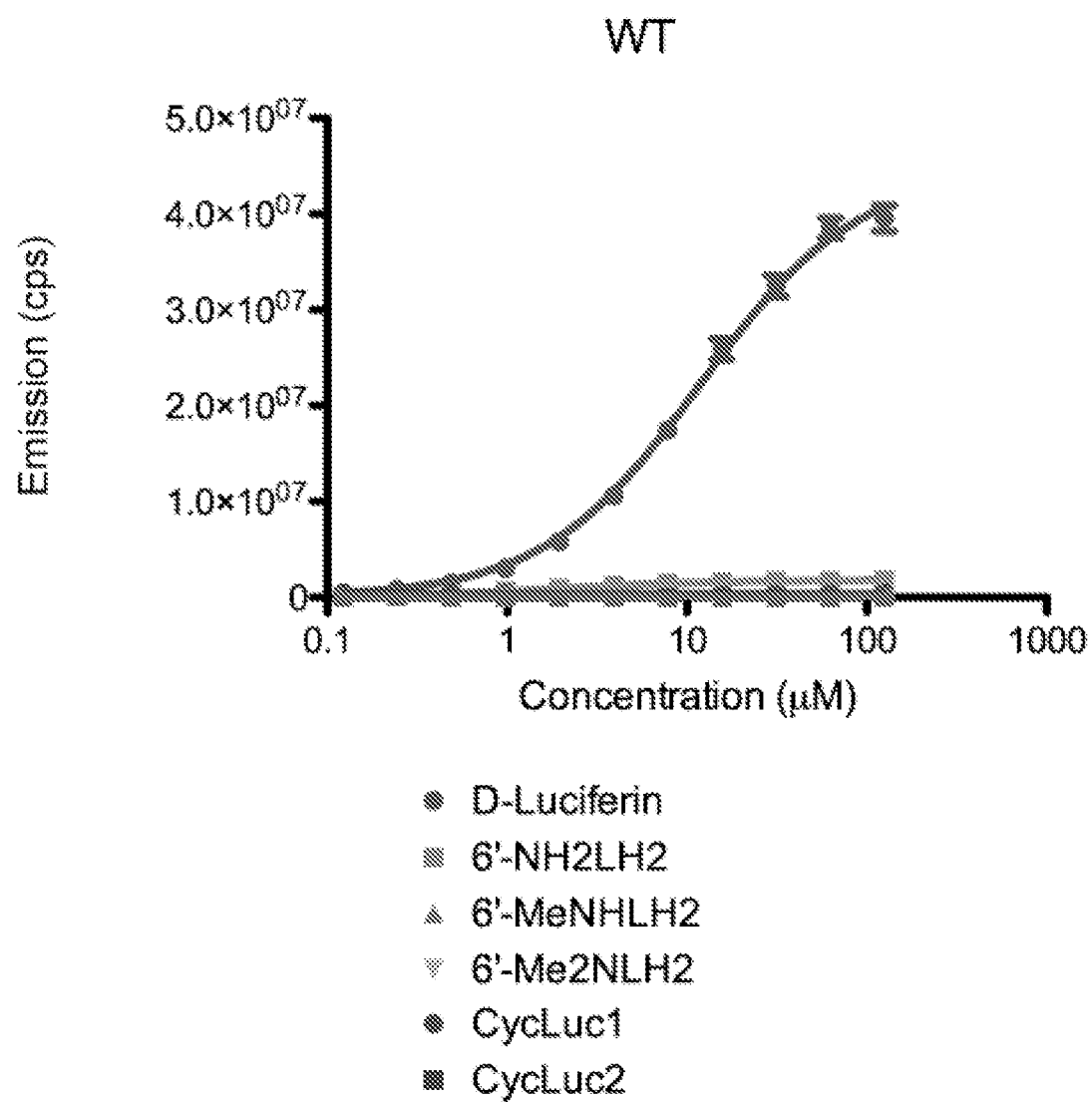
FIGS. 13A-J are bar graphs showing the results when CHO-K1 cells were transiently transfected with pcDNA3.1 vectors expressing WT, T251 S, L286M, S347A, or R218K firefly luciferase. Dose-response curves are shown for each luciferase with D-luciferin, 60-NH2LH2, 60-MeNHLH2, 60-Me2NLH2, CycLuc1, and CycLuc2 were generated at concentrations of 0.122-125 µM using lysates from the transfected cells (13A-E) or using the intact live cells (13F-J). The assays were performed in triplicate and are represented as the mean±SEM. Note that the WT emission scale is larger than that of the mutants by two-fold and three-fold for cell lysates and live cells, respectively.
Figure 13B:
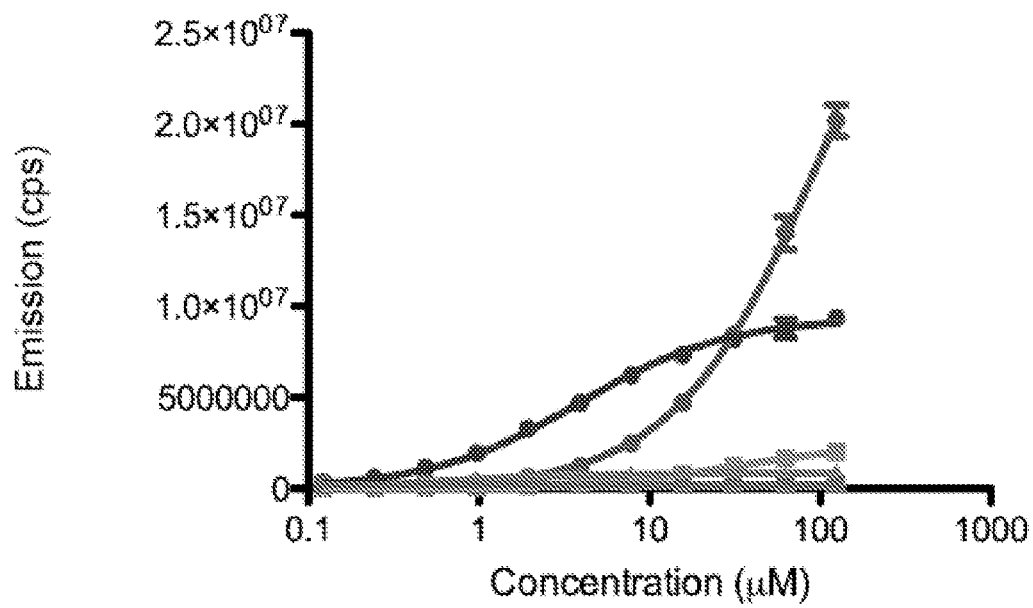
Figure 13C:
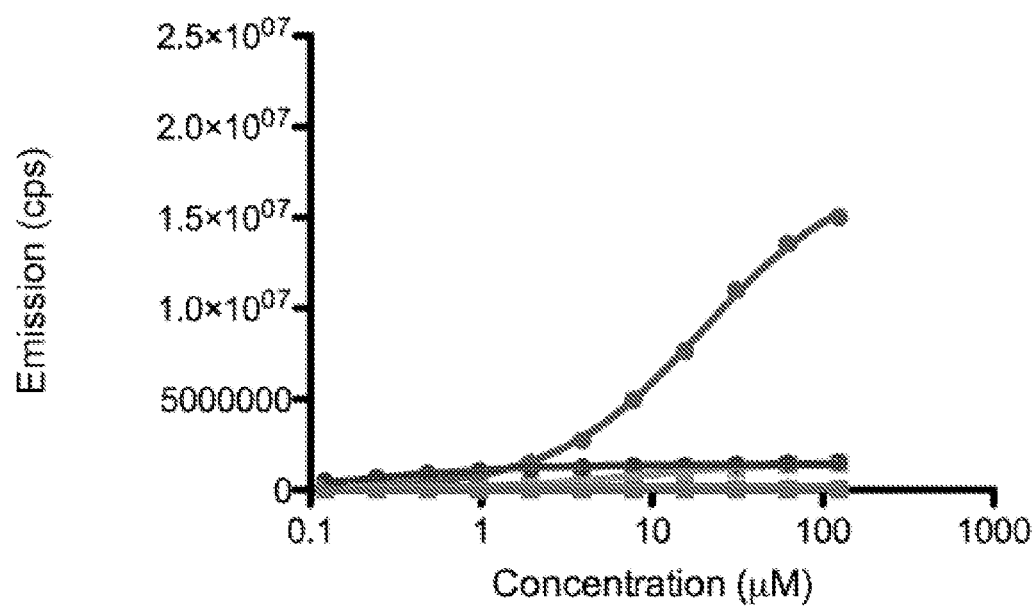
Figure 13D:
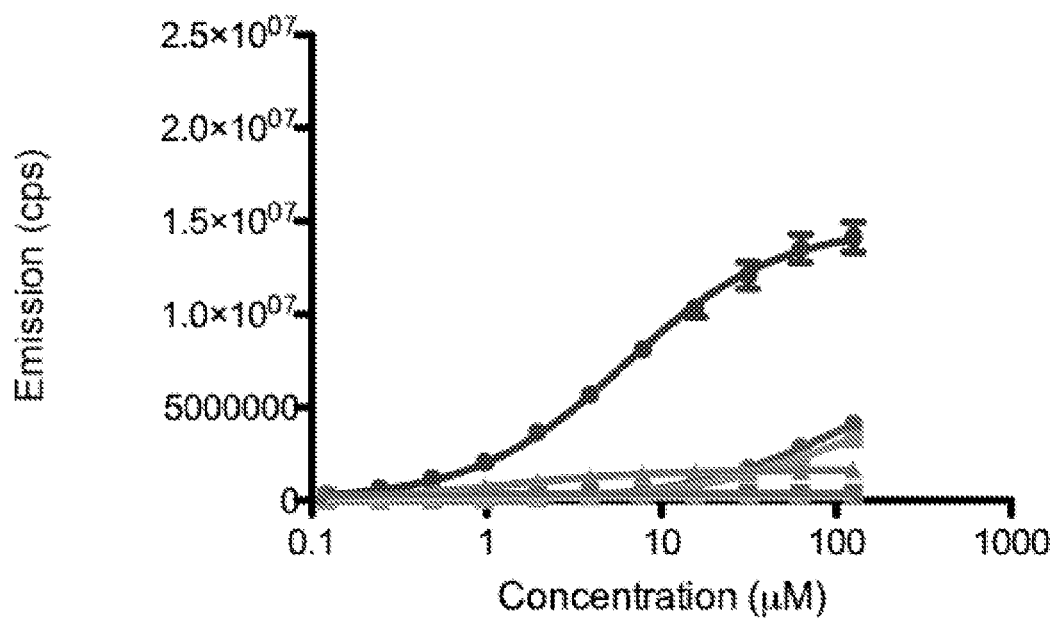
Figure 13E:
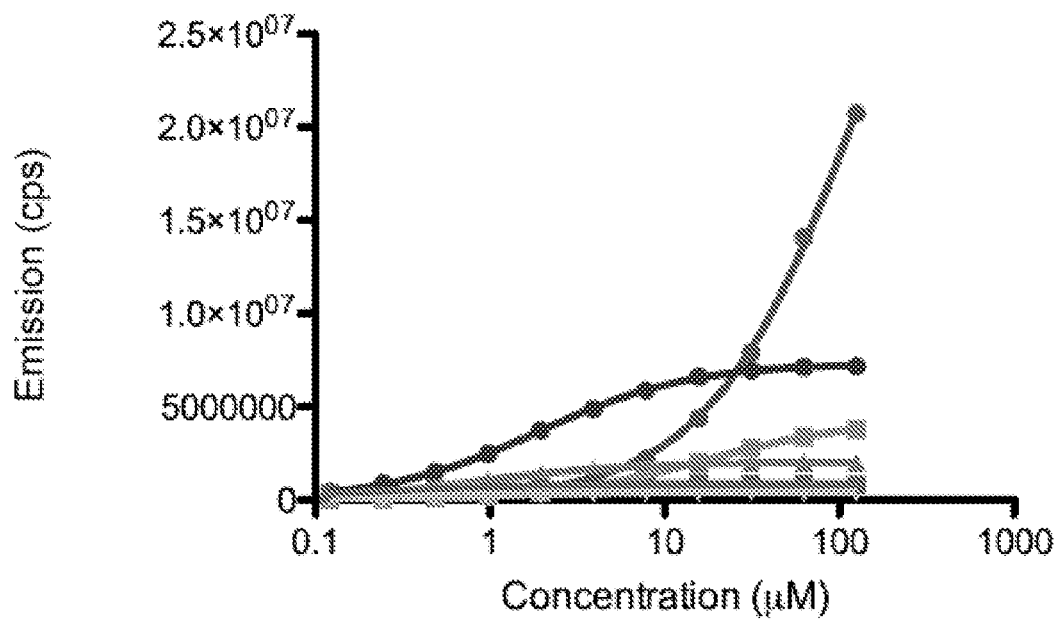
Figure 13F:
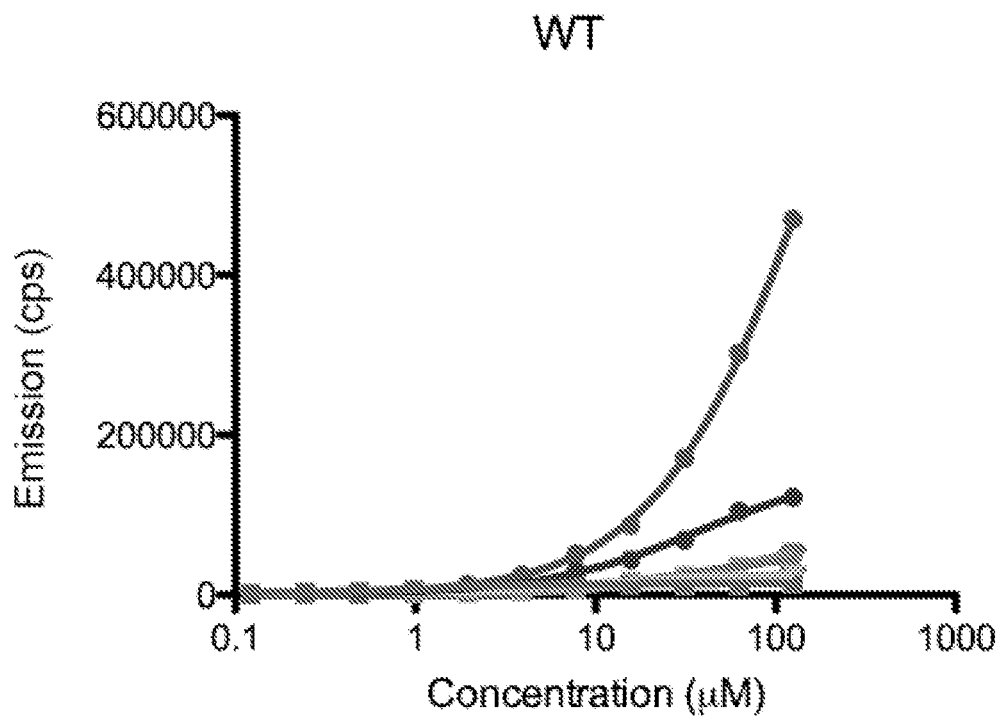
Figure 13G:
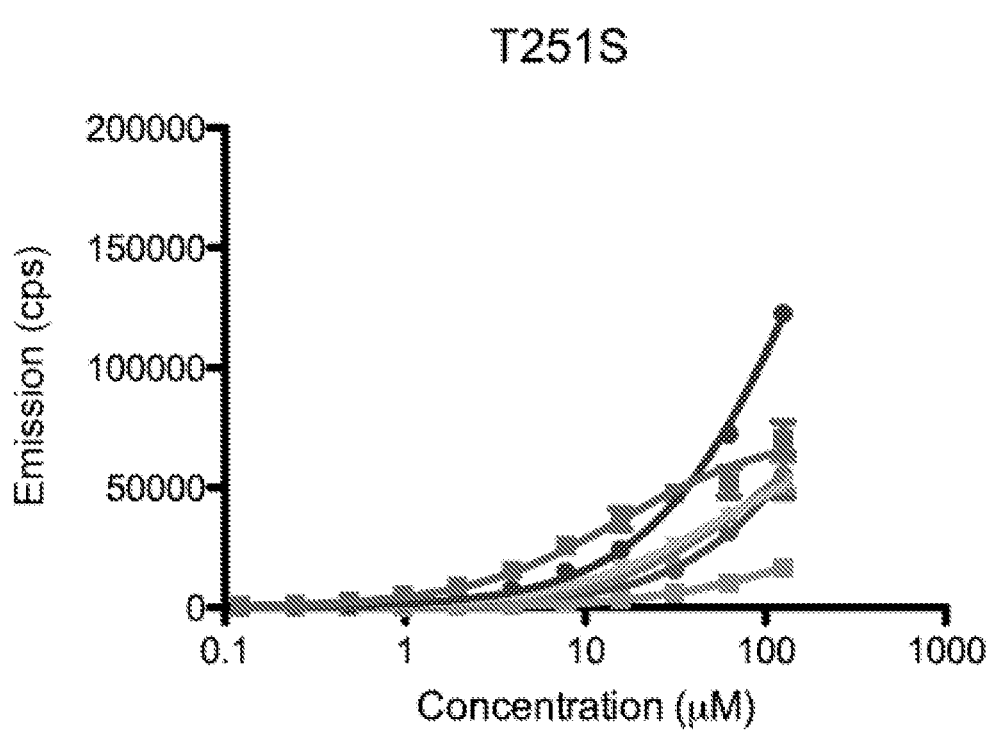
Figure 13H:
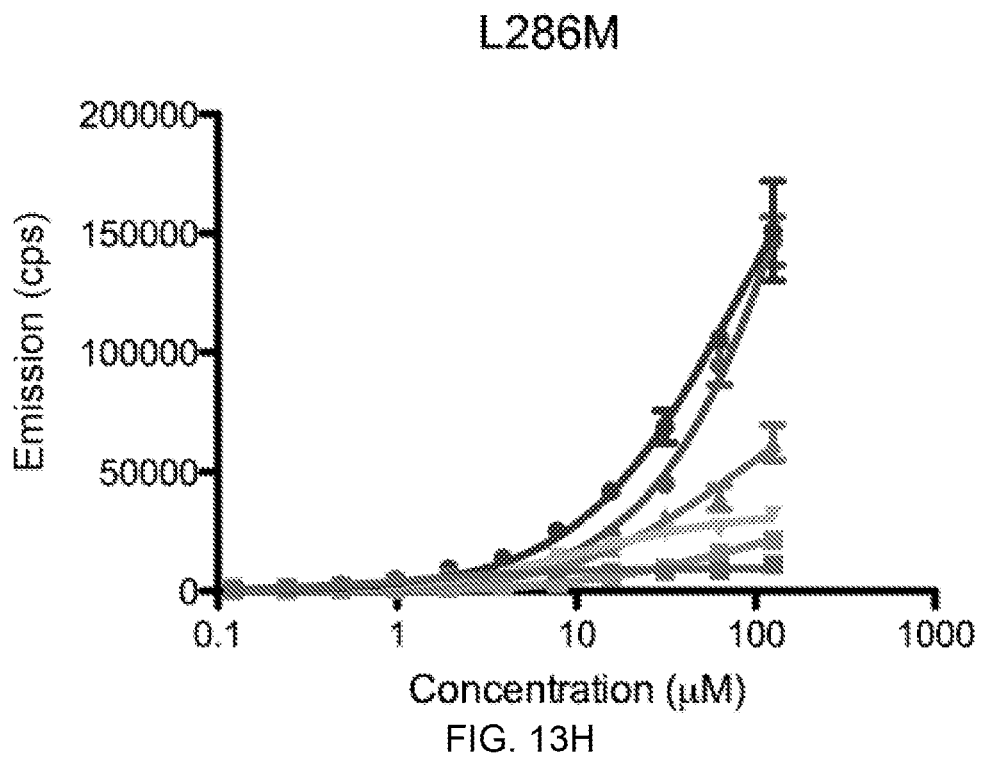
Figure 13I:
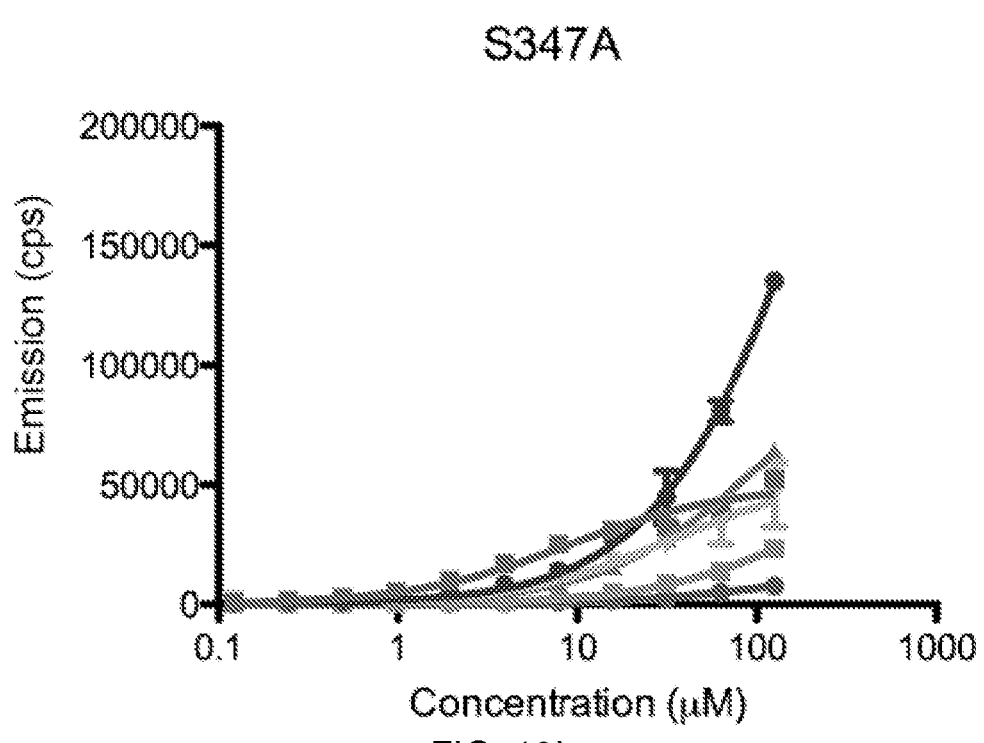
Figure 13J:
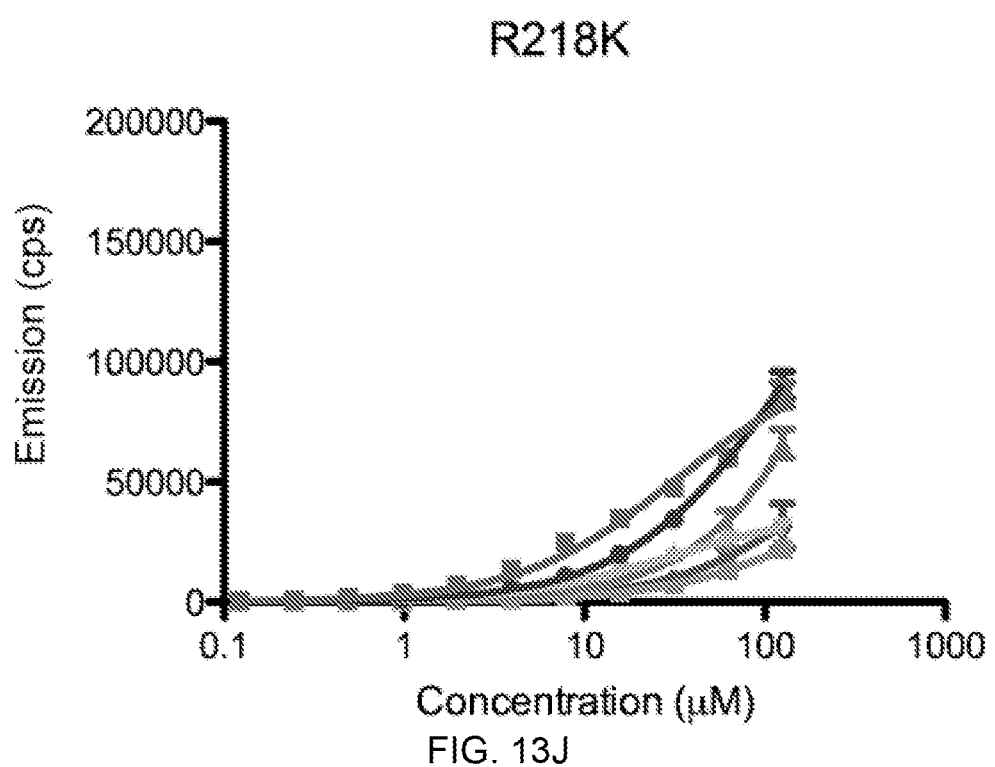

Wild-type luciferase treated with D-luciferin produces robust light emission, but is prone to inhibition from small molecules (FIGS. 12A-H). This limits the use of luciferase as a reporter in high-throughput small molecule drug screens. The use of high-affinity synthetic luciferin analogs with mutant luciferases can resist inhibition from small molecules, as shown with the R218K luciferase in conjunction with CycLuc2 (FIGS. 12A-H). Consistent light is emitted from this combination, even in the presence of a luciferase inhibitor (2-(4-methoxyphenyl)-benzothiazole) that dramatically reduces the light produced from the wild-type enzyme and D-luciferin. As shown in FIG. 12H, when CycLuc2 is used as substrate, the light output from the R218K mutant luciferase is linearly dependent on the luciferase concentration and largely unaffected by the presence or absence of the luciferase inhibitor. In contrast, as shown in FIGS. 12E and 12G, the light output from WT or R218K luciferase when treated with D-luciferin is strongly inhibited by the luciferase inhibitor, such that the measured light output is no longer a reliable measure of luciferase concentration.

Example 4

Exemplary Synthetic Schemes for CvcLuc3 and CycLuc4

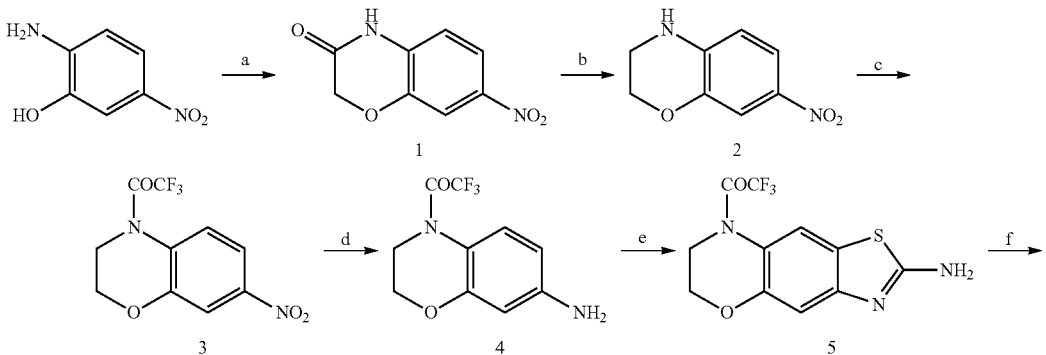

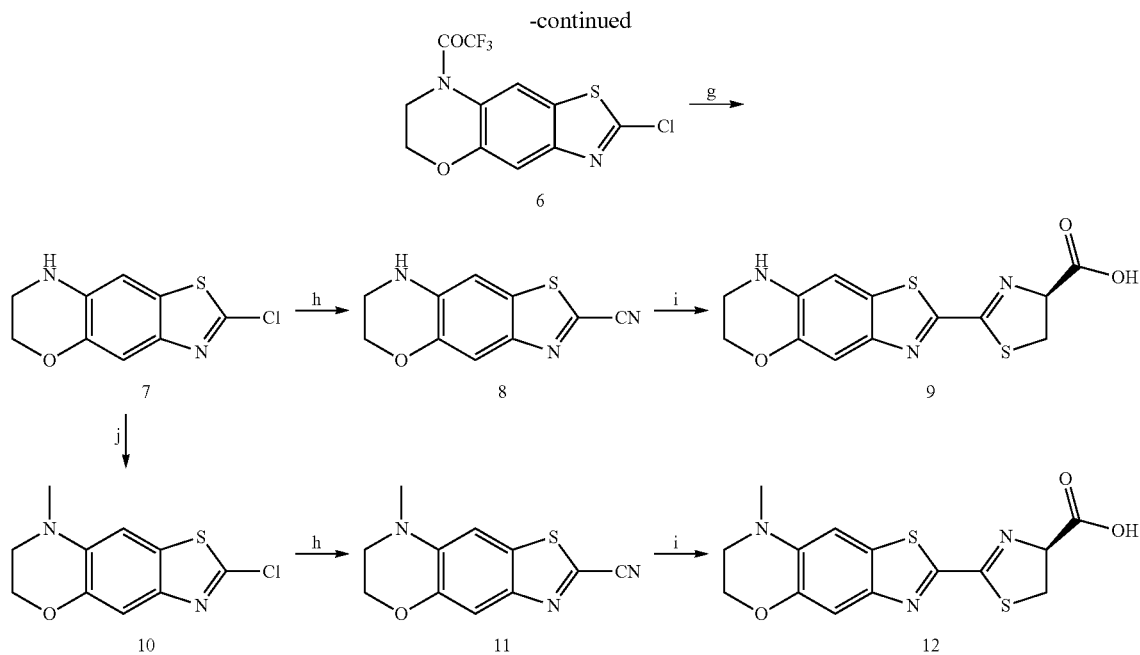

Reagents and conditions: (a) Methyl bromoacetate, K₂CO₃, DMF, 90° C., 24 h; (b) BH₃—THF (1M in THF), THF, reflux, 30 min; (c) TFAA, TEA, CH₂Cl₂, rt, 45 min; (d) SnCl₂—2H₂O, EtOH, reflux, 4h; (e) KSCN, Br₂, AcOH, rt, 21 h; (f) t-Butyl nitrite, CuCl, CH₃CN, rt, 2 h, 65° C., 1 h; (g) NaBH₄, CH₃OH, rt, 15 min; (h) KCN, DMSO, 130° C., 3 h; (i) D-cysteine, 50 mM aqueous sodium phosphate buffer, pH 8, CH₃OH; (j) HCHO, NaBH(OAc)₃, DCE, rt, 1h.

7-Nitro-4H-benzo[1,4]oxazin-3-one (1)

Methyl bromoacetate (3.58 g, 39 mmol), 2-amino-5-nitrophenol (5 g, 32.5 mmol) and K₂CO₃ (11.5 g, 81.0 mmol) in DMF (15 mL) were heated at 90° C. for 24 h. The reaction mixture was allowed to cool, and then diluted with water. The resulting precipitate was collected by filtration and dried under vacuum to give 1 as a brown solid (4.5 g, 71%). $^1$H-NMR (400 MHz, d6-DMSO): δ 11.30 (s, 1H), 7.89 (dd, 1H, J=2.5, 8.7 Hz), 7.75 (d, 1H, J=2.5 Hz), 7.04 (d, 1H, J=8.7 Hz), 4.71 (s, 2H). HRMS (ESI⁺) Calcd for C₈H₇N₂O₄Na: 217.0225. Found: 217.0243.

7-Nitro-3,4-dihydro-2H-benzo[1,4]oxazine (2)

A solution of 1 (2 g, 10.3 mmol) in THF (10 mL) was treated with 1M BH₃/THF (35 mL). The solution was refluxed for 30 min then cooled to 0° C., and quenched with 1N HCl (20 mL). The solution was stirred for 30 min then concentrated and extracted with ethyl acetate (2×100 mL). Evaporation of the ethyl acetate yielded 2 (1.5 g, 80%). $^1$H-NMR (400 MHz, d6-DMSO): δ 7.66 (dd, 1H, J=9.2, 2.4 Hz), 7.53 (s, 1H), 7.45 (d, 1H, J=2.4 Hz), 6.60 (d, 1H, J=8.8 Hz) 4.12 (t, 2H, J=6.8 Hz), 3.41-3.31 (m, 2H). HRMS (ESI⁺) Calcd for C₈H₉N₂O₃: 181.0613. Found: 181.0619.

2,2,2-Trifluoro-1-(7-nitro-2,3-dihydro-benzo[1,4]oxazin-4-yl)-ethanone (3)

7-Nitro-4H-benzo[1,4]oxazin-3-one (1.5 g, 8.3 mmol) and triethylamine (0.924 g, 10.0 mmol) were stirred in dichloromethane (20 mL) as trifluoroacetic anhydride (4.5 g, 12.5 mmol) was added dropwise. This mixture was stirred for 45 min; then water (50 mL) was added. After stirring for 10 min, the mixture was acidified with 5M HCl. The organic layer was washed with brine, dried and evaporated to give a yellow solid (2.1 g, 91%). $^1$H-NMR (400 MHz, CDCl₃): δ 8.17 (s, 1H), 7.82-7.79 (m, 2H), 4.47 (t, 2H, J=4.8 Hz), 4.05 (t, 2H, J=4.8 Hz). $^{13}$C-NMR (100 MHz, CDCl₃): δ 155.1 (q, $^2J_{CF}$=37 Hz), 147.3, 146.0, 129.5, 124.4, 116.2 (q, $^1J_{CF}$=287 Hz), 115.9, 113.4, 65.9, 43.4. $^{19}$F-NMR (376 MHz, CDCl₃): δ −68.9. HRMS (ESI⁺) Calcd for C₁₀H₈F₃N₂O₄: 277.0436. Found: 277.0438.

1-(7-Amino-2,3-dihydro-benzo[1,4]oxazin-4-yl)-2,2,2-trifluoro-ethanone (4)

SnCl₂.2H₂O (4.89 g, 21.73 mmol) was added to a solution of 3 (2 g, 7.24 mmol) in ethanol (20 mL) and the reaction mixture was heated to reflux for 4 h. After cooling to room temperature the solvent was evaporated under vacuum. The resulting residue was dissolved in saturated NaHCO₃ (50 mL) and extracted with ethyl acetate (2×100 mL). After washing with brine and evaporation of the organic layer under vacuum, the residue was purified by flash chromatography (25% ethyl acetate: hexane) to give 4 (1.2 g, 67%). $^1$H-NMR (400 MHz, CDCl₃): δ 7.78 (d, 1H, J=9.2), 6.28 (dd, 1H, J=9.2, 2.4 Hz), 6.22 (d, 1H, J=2.4 Hz), 4.33 (t, 2H, J=4.8 Hz), 3.92 (t, 2H, J=4.8 Hz), 3.56 (s, 2H). $^{13}$C-NMR (100 MHz, CDCl₃): δ 153.9 (q, $^2J_{CF}$=36 Hz), 148.0, 146.0, 124.9, 116.7 (q, $^1J_{CF}$=286 Hz), 115.5, 112.4, 108.2, 102.8, 65.9, 43.9. $^{19}$F-NMR (376 MHz, CDCl₃): δ −68.8. HRMS (ESI⁺) Calcd for C₁₀H₁₀F₃N₂O₂: 247.0694. Found: 247.0707.

1-(2-Amino-6,7-dihydro-5-oxa-1-thia-3,8-diaza-cyclopenta[b]naphthalen-8-yl)-2,2,2-trifluoro-ethanone (5)

A solution of 4 (1 g, 4.06 mmol) and potassium thiocyanate (1.57 g, 16.2 mmol) in AcOH (20 mL) was stirred at 20° C. for 10 min. Bromine (0.64 g, 4.06 mmol) was added dropwise over 20 min. The reaction mixture was stirred at room temperature for an additional 21 h. The reaction mixture was then poured onto crushed ice and the pH was adjusted to 8 using NH$_4$OH. The resulting precipitate was vacuum-filtered and dried to give 5, which was used for next step without further purification (1.2 g, 97%). HRMS (ESI$^+$) Calcd for C$_{11}$H$_9$F$_3$N$_3$O$_2$S: 304.0367. Found: 304.0349.

1-(2-Chloro-6,7-dihydro-5-oxa-1-thia-3,8-diaza-cyclopenta[b]naphthalen-8-yl)-2,2,2-trifluoro-ethanone (6)

To a mixture of t-butyl nitrite (0.56 g, 5.44 mmol), cupric chloride (0.43 mg, 4.3 mmol) and acetonitrile (10 mL) was added 5 (1.1 g, 3.63 mmol) in portions over 1 h. The reaction mixture was stirred at room temperature for 2 h, then heated to 65° C. for 1 h. The mixture was cooled, filtered and the filtrate was poured into 6N HCl and extracted with ethyl acetate. After concentration the crude product was used for next step without further purification (1 g, 85%). $^1$H-NMR (400 MHz, CDCl$_3$): δ 8.46 (s, 1H), 7.50 (s, 1H), 4.44 (t, 2H, J=4.8 Hz), 4.05 (t, 2H, J=4.8 Hz). $^{13}$C-NMR (100 MHz, CDCl$_3$): δ 155.5, 154.9 (q, $^1J_{CF}$=35 Hz), 149.9, 146.9, 128.5, 123.5, 116.4 (q, $^2J_{CF}$=287 Hz), 116.0, 110.8, 65.8, 43.7. $^{19}$F-NMR (376 MHz, CDCl$_3$): δ −68.9. HRMS (ESI$^+$) Calcd for C$_{11}$H$_7$ClF$_3$N$_2$O$_2$S: 322.9869. Found: 322.9859.

2-Chloro-7,8-dihydro-6H-5-oxa-1-thia-3,8-diaza-cyclopenta[b]naphthalene (7)

Compound 6 (1 g, 3.11 mmol) was stirred in methanol (20 mL) as NaBH$_4$ (461 mg, 12.4 mmol) was added in portions over five minutes. The mixture was stirred for 15 min, diluted with water and extracted with ethyl acetate. The organic layer was washed with brine and evaporated. The crude product was purified by flash chromatography (25% ethyl acetate: hexane) to give 7 (0.35 g, 49%). $^1$H-NMR (400 MHz, CDCl$_3$): δ 7.32 (s, 1H), 6.83 (s, 1H), 4.27 (t, 2H, J=4.8 Hz), 4.04 (s, 1H), 3.46 (t, 2H, J=4.0 Hz). $^{13}$C-NMR (100 MHz, CDCl$_3$): δ 148.8, 144.5, 144.3, 134.1, 129.7, 110.2, 104.9, 65.2, 40.8. HRMS (ESI$^+$) Calcd for C$_9$H$_3$ClN$_2$OS: 227.0046. Found: 227.0020.

7,8-Dihydro-6H-5-oxa-1-thia-3,8-diaza-cyclopenta[b]naphthalene-2-carbonitrile (8)

Potassium cyanide (28.7 mg, 0.44 mmol) was added to a solution of 7 (50 mg, 0.22 mmol) in DMSO (5 mL) and stirred for 3 h at 130° C. The reaction was cooled to room temperature, poured into water, and extracted with ethyl acetate (2×20 mL). The organic phase was evaporated to dryness and purified by flash chromatography using 10% ethyl acetate: hexane as eluent (13 mg, 27%). $^1$H-NMR (400 MHz, CDCl$_3$): δ 7.54 (s, 1H), 6.95 (s, 1H), 4.41 (s, 1H), 4.31 (t, 2H, J=4.8 Hz), 3.55-3.52 (m, 2H). $^{13}$C-NMR (100 MHz, CDCl$_3$): δ 145.8, 145.6, 137.3, 130.5, 118.6, 114.0, 111.4, 103.2, 64.9, 40.5. HRMS (ESI$^+$) Calcd for C$_{10}$H$_8$N$_3$OS: 218.0388. Found: 218.0416.

CycLuc3 [2-(7,8-Dihydro-6H-5-oxa-1-thia-3,8-diaza-cyclopenta[b]naphthalen-2-yl)-4,5-dihydro-thiazole-4-carboxylic acid] (9)

D-cysteine (2.9 mg, 0.016 mmol) was dissolved in 1 mL of 50 mM aqueous sodium phosphate buffer, pH 8 and degassed under argon. This solution was added to 8 (3 mg, 0.013 mmol) in 1 mL of degassed methanol. The reaction was stirred for 1 h, and then diluted with sodium phosphate buffer and washed with ethyl acetate. The aqueous phase was acidified to pH 4 with 1M HCl and extracted with ethyl acetate (2×5 mL). The solvent was removed by rotary evaporation to yield 9 as an orange red solid (2 mg, 47%). $^1$H-NMR (400 MHz, CDCl$_3$+2 drops CD$_3$OD): δ 7.43 (s, 1H), 6.91 (s; 1H), 5.27 (t, 1H, J=4.8 Hz), 4.23 (t, 2H, J=4.4 Hz), 3.73-3.61 (m, 2H), 3.43 (t, 2H, J=4.4 Hz). $^{13}$C-NMR (100 MHz, CDCl$_3$+2 drops CD$_3$OD): δ 172.3, 166.9, 156.0, 146.3, 144.8, 136.1, 130.7, 110.8, 104.2, 78.2, 64.9, 40.4, 35.2. HRMS (ESI$^+$) Calcd for C$_{13}$H$_{12}$N$_3$O$_3$S$_2$: 322.0320. Found: 322.0354.

2-Chloro-8-methyl-7,8-dihydro-6H-5-oxa-1-thia-3,8-diaza-cyclopenta[b]naphthalene (10)

Compound 7 (50 mg, 0.22 mmol) and formaldehyde (26.4 mg, 0.88 mmol) were dissolved in dichloroethane (10 mL). Sodium triacetoxyborohydride (70.3 mg, 0.33 mmol) was added and the reaction mixture was stirred for 1 h at ambient temperature. The reaction was quenched with 1N NaOH (10 mL). The product was extracted with ethyl acetate (2×20 mL), washed with brine and dried (MgSO$_4$). The solvent was removed by rotary evaporation and the resulting solid was purified by flash chromatography using 8% ethyl acetate: hexane as eluent (20 mg, 37%). $^1$H-NMR (400 MHz, CDCl$_3$): δ 7.31 (s, 1H), 6.86 (s, 1H), 4.33-4.31 (m, 2H), 3.35-3.33 (m, 2H), 2.94 (s, 3H). $^{13}$C-NMR (100 MHz, CDCl$_3$): δ 148.6, 144.6, 143.5, 136.7, 130.1, 109.2, 101.9, 64.9, 48.9, 39.2. HRMS (ESI$^1$) Calcd for C$_{10}$H$_{10}$ClN$_2$OS: 241.0202. Found: 241.0206.

8-Methyl-7,8-dihydro-6H-5-oxa-1-thia-3,8-diaza-cyclopenta[b]naphthalene-2-carbonitrile (11)

Potassium cyanide (11.5 mg, 0.17 mmol) was added to a solution of 10 (20 mg, 0.083 mmol) in DMSO (3 mL) and stirred for 3 h at 130° C. The reaction was cooled to room temperature, poured into water, and extracted with ethyl acetate (2×20 mL). The organic phase was evaporated to dryness and purified by flash chromatography using 10% ethyl acetate: hexane as eluent (7 mg, 36%). $^1$H-NMR (400 MHz, CDCl$_3$): δ 7.50 (s, 1H), 6.94 (s, 1H), 4.33 (t, 2H, J=4.8 Hz), 3.45 (t, 2H, J=4.8 Hz), 3.03 (s, 3H). $^{13}$C-NMR (100 MHz, CDCl$_3$): δ 145.9, 145.2, 139.4, 131.2, 114.1, 110.3, 107.9, 100.1, 64.5, 48.7, 38.9. HRMS (ESI$^+$) Calcd for C$_{11}$H$_{10}$N$_3$OS: 232.0545. Found: 232.0552.

CycLuc4 [2-(8-Methyl-7,8-dihydro-6H-5-oxa-1-thia-3,8-diaza-cyclopenta[b]naphthalen-2-yl)-4,5-dihydro-thiazole-4-carboxylic acid] (12)

D-cysteine (3.6 mg, 0.0020 mmol) was dissolved in 1 mL of 50 mM aqueous sodium phosphate buffer, pH 8 and degassed under argon. This solution was added to 11 (4 mg, 0.017 mmol) in 1 mL of degassed methanol. The reaction was stirred for 1 h, and then diluted with sodium phosphate buffer and washed with ethyl acetate. The aqueous phase was acidified to pH 4 with 1M HCl and extracted with ethyl acetate (2×5 mL). The solvent was removed by rotary evaporation to yield 12 as an orange red solid (4 mg, 70%). $^1$H-NMR (400 MHz, CDCl$_3$+2 drops CD$_3$OD): δ 7.41 (s, 1H), 6.92 (s, 1H), 5.26 (t, 1H, J=5.2 Hz), 4.26 (t, 2H, J=4.8 Hz), 3.72-3.61 (m, 2H), 3.35 (t, 2H, J=4.8 Hz), 2.95 (s, 3H). $^{13}$C-NMR (100 MHz, CDCl$_3$+2 drops CD$_3$OD): δ 172.2, 166.8, 155.8, 145.9, 145.1, 138.2, 131.3, 109.9, 101.2, 78.2, 64.6, 50.0, 38.9, 35.2. HRMS (ESI+) Calcd for C$_{14}$H$_{14}$N$_3$O$_3$S2: 336.0477. Found: 336.0467.

Example 5

Exemplary Synthetic Schemes for CycLuc5 and CycLuc6

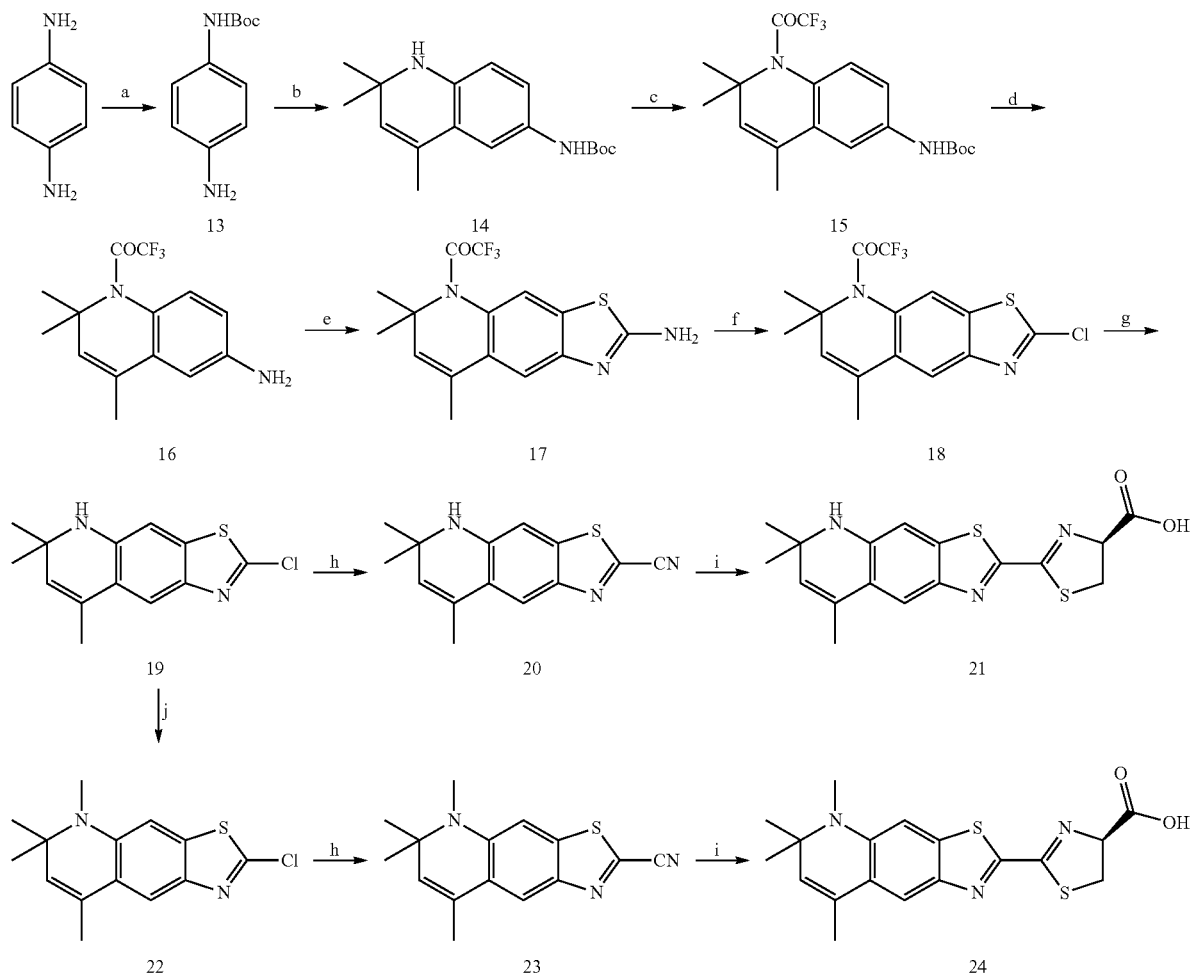

Reagents and conditions: (a) Boc$_2$O, 1,4-dioxane, 0° C.-rt, overnight; (b) Acetone, t-butyl catechol, MgSO$_4$, iodine, 63° C., 2 days; (c) TFAA, TEA, CH$_2$Cl$_2$, rt, 45 min; (d) 15% TFA in DCM, rt, 5 h; (e) KSCN, Br$_2$, AcOH, rt, 21 h; (f) t-Butyl nitrite, CuCl, CH$_3$CN, rt, 2 h then 65° C., 1 h; (g) NaBH$_4$, CH$_3$OH, rt, 15 min; (h) KCN, DMSO, 130° C., 3 h; (i) D-cysteine, 0.1M aqueous sodium phosphate buffer, pH 8, CH$_3$OH; (j) CH$_3$I, K$_2$CO$_3$, DMF, 65° C., overnight.

(4-Amino-phenyl)-carbamic acid tert-butyl ester (13)

To a solution of 1,4-phenylenediamine (5 g, 46 mmol) in dioxane (90 mL) on ice, a solution of Boc$_2$O (2 g, 9.2 mmol) in dioxane (10 mL) was slowly added. The mixture was stirred overnight at room temperature. The solvent was evaporated and the remaining solid was dissolved in DCM/MeOH (9/1) and washed with saturated NaHCO$_3$ (100 mL), H$_2$O (100 mL) and brine. The organic phase was dried over Na$_2$SO$_4$, filtered and concentrated. Purification by column chromatography (20-50% EtOAc in hexane) gave the desired product (1.8 g, 95%). $^1$HNMR (400 MHz, CDCl$_3$): δ 7.13-7.11 (m, 2H), 6.64-6.61 (m, 2H), 6.24 (br s, 1H), 3.51 (br s, 2H), 1.50 (s, 9H). HRMS (ESI+) Calcd for C$_{11}$H$_{17}$N$_2$O$_2$: 209.1290. Found: 209.1287.

(2,2,4-Trimethyl-1,2-dihydro-quinolin-6-yl)-carbamic acid tert-butyl ester (14)

To a solution of 13 (1.5 g, 7.21 mmol) in 17 mL acetone was added MgSO$_4$ (4.3 g, 36 mmol) and tert-butyl catechol (35 mg, 0.21 mmol, 3.0 mol %). Iodine (91 mg, 0.036 mmol, 5.0 mol %) was then added to the reaction mixture and the reaction was heated to reflux (63° C.) for 2 days. The reaction was then cooled to it, diluted with ethyl acetate (50 mL), filtered and concentrated. The resulting residue was dissolved in DCM (50 mL) and washed with 3M NaOH (4×20 mL) and water (3×20 mL) to remove tert-butyl catechol. The organic layer was dried over Na$_2$SO$_4$ and concentrated under vacuum. The crude product was purified by column chromatography using 8% ethyl acetate: hexane to obtain 14 as brown-yellow oil which solidifies over time (950 mg, 45%). $^1$H NMR (400 MHz, CDCl$_3$): δ 7.05 (s, 1H), 6.94 (d, 1H, J=7.2 Hz), 6.44 (br s, 1H), 6.35 (d, 1H, J=8.0 Hz), 5.31 (s, 1H), 3.61 (br s, 1H), 1.94 (d, 3H, J=4.0 Hz), 1.50 (s, 9H), 1.23 (s, 6H). $^{13}$C-NMR (100 MHz, CDCl$_3$): δ

153.8, 140.0, 129.4, 128.7, 128.6, 122.2, 120.8, 116.2, 113.3, 79.9, 51.9, 30.8, 28.7, 18.7. HRMS (ESI+) Calcd for $C_{17}H_{25}N_2O_2$: 289.1916. Found: 289.1941.

[2,2,4-Trimethyl-1-(2,2,2-trifluoro-acetyl)-1,2-dihydro-quinolin-6-yl]-carbamic acid tert-butyl ester (15)

Trifluoroacetic anhydride (1.03 g, 4.9 mmol) was added dropwise to a solution of 14 (950 mg, 3.2 mmol) in dichloromethane (10 mL) and pyridine (1.06 mL) at 0° C. The reaction was stirred at ambient temperature for 45 min, and then quenched by the slow addition of water (10 ml). The organic phase was separated, washed with 10% hydrochloric acid (3×15 mL) and water (15 mL), and dried over $Na_2SO_4$. The solvent was removed under vacuum and the resulting residue was purified by flash chromatography using 5% ethyl acetate: hexane to provide 15 (900 mg, 73%). $^1$H NMR (400 MHz, $CDCl_3$): δ 7.39 (d, 1H, J=4.0 Hz), 7.12 (dd, 1H, J=8.4, 4.0 Hz), 6.81 (d, 1H, J=8.0 Hz), 6.51 (br s, 1H), 5.57 (d, 1H, J=1.2 Hz), 2.05 (d, 3H, J=4.0 Hz), 1.52 (s, 9H). $^{13}$C-NMR (100 MHz, $CDCl_3$): δ 158.5 (q, $^2J_{CF}$=36 Hz), 152.8, 137.3, 135.2, 129.8, 128.8, 128.6, 123.3 (q, $^4J_{CF}$=3 Hz), 117.2, 116.4 (q, $^1J_{CF}$=289 Hz), 113.9, 81.1, 59.9, 28.5, 25.7, 18.0. $^{19}$F-NMR (376 MHz, $CDCl_3$): δ −67.35. HRMS (ESI+) Calcd for $C_{19}H_{23}F_3N_2O_3Na$: 407.1559. Found: 407.1537.

1-(6-Amino-2,2,4-trimethyl-2H-quinolin-1-yl)-2,2,2-trifluoro-ethanone (16)

15% TFA in DCM (13 mL) was added to a solution of 15 (900 mg, 2.34 mmol) in DCM (10 mL) The reaction was stirred for 5 h at room temperature followed by addition of toluene. The mixture was concentrated, dissolved in DCM (25 mL) and washed with saturated aqueous $NaHCO_3$ (2×10 mL). The organic layer was dried over $Na_2SO_4$ and concentrated under vacuum to yield the crude product which was used in the next step without further purification (600 mg, 90%). HRMS (ESI+) Calcd for $C_{14}H_{16}F_3N_2O$: 285.1215. Found: 285.1197.

1-(2-Amino-6,6,8-trimethyl-6H-thiazolo[4,5-g]quinolin-5-yl)-2,2,2-trifluoro-ethanone (17)

A solution of 16 (600 mg, 2.11 mmol) and potassium thiocyanate (819 mg, 8.45 mmol) in AcOH (20 mL) was stirred at 20° C. for 10 min. Bromine (335 mg, 2.11 mmol) was added over 20 min and the reaction mixture was stirred further at room temperature for 21 h. The reaction mixture was poured onto crushed ice and the pH was adjusted to 8 using $NH_4OH$. The resulting precipitate was vacuum-filtered and dried to give the title compound, which was used for the next step without further purification (650 mg, 91%). HRMS (ESI+) Calcd for $C_{15}H_{15}F_3N_2OS$: 342.0888. Found: 342.0851.

1-(2-Chloro-6,6,8-trimethyl-6H-thiazolo[4,5-g]quinolin-5-yl)-2,2,2-trifluoro-ethanone (18)

To a mixture of t-butyl nitrite (294 mg, 2.85 mmol), cupric chloride (225 mg, 2.28 mmol) and acetonitrile (20 mL) was added 17 (650 mg, 1.90 mmol) in portions over 1 h. The reaction mixture was stirred at room temperature for 2 h heated to 65° C. for 1 h. The mixture was filtered and the filtrate was poured into 6N HCl and extracted with ethyl acetate (2×50 mL). After concentration the crude product was purified by flash chromatography (500 mg, 73%). $^1$H-NMR (400 MHz, $CDCl_3$): δ 7.81 (s, 1H), 7.24 (s, 1H), 5.67 (d, 1H, J=1.2 Hz), 2.12 (d, 3H, J=1.6 Hz), 1.54 (s, 6H). $^{13}$C-NMR (100 MHz, $CDCl_3$): δ 158.3 (q, $^2J_{CF}$=36 Hz), 153.7, 150.0, 135.6, 135.0, 132.4, 128.8, 128.3, 117.6, 116.3 (q, $^1J_{CF}$=289 Hz), 114.6 (q, $^4J_{CF}$=3 Hz), 60.4, 25.4, 18.2. $^{19}$F-NMR (376 MHz, $CDCl_3$): δ −67.08. HRMS (ESI+) Calcd for $C_{15}H_{13}ClF_3N_2OS$: 361.0389. Found: 361.0367.

2-Chloro-6,6,8-trimethyl-5,6-dihydro-thiazolo[4,5-g]quinoline (19)

The trifluoroacetamide 18 (500 mg, 1.4 mmol) was stirred in methanol (5 mL) as $NaBH_4$ (217 mg, 5.8 mmol) was added. The mixture was stirred for 15 min, diluted with water (50 mL) and extracted with ethyl acetate (2×50 mL). The organic layer was washed with brine and evaporated to give 19 (250 mg, 67%). $^1$H-NMR (400 MHz, $CDCl_3$): δ 7.57 (s, 1H), 6.68 (s, 1H), 5.44 (d, 1H, J=4.0 Hz), 3.89 (br s, 1H), 2.03 (d, 3H, J=1.2 Hz), 1.30 (s, 6H). $^{13}$C-NMR (100 MHz, $CDCl_3$): δ 147.4, 143.8, 142.6, 136.9, 130.4, 128.2, 122.5, 117.6, 102.8, 52.5, 31.3, 18.9. HRMS (ESI+) Calcd for $C_{13}H_{14}ClN_2S$: 265.0566. Found: 265.0557.

6,6,8-Trimethyl-5,6-dihydro-thiazolo[4,5-g]quinoline-2-carbonitrile (20)

Potassium cyanide (49 mg, 0.75 mmol) was added to a solution of 19 (100 mg, 0.37 mmol) in DMSO (5 mL) and stirred for 3 h at 130° C. The reaction was cooled to room temperature, poured into water, and extracted with ethyl acetate (2×20 mL). The organic phase was evaporated to dryness and the crude material purified by flash chromatography using 10% ethyl acetate: hexane as eluent (55 mg, 58%). $^1$H-NMR (400 MHz, $CDCl_3$): δ 7.77 (s, 1H), 6.76 (s, 1H), 5.51 (d, 1H, J=1.2 Hz), 4.24 (brs, 1H), 2.07 (d, 3H, J=1.2 Hz), 1.35 (s, 6H). $^{13}$C-NMR (100 MHz, $CDCl_3$): 145.5, 145.2, 137.5, 131.3, 129.5, 127.7, 123.9, 119.6, 114.2, 101.3, 53.1, 31.9, 18.9. HRMS (ESI+) Calcd for $C_{14}H_{14}N_3S$: 256.0909. Found: 256.0907.

CycLuc5 [2-(6,6,8-Trimethyl-5,6-dihydro-thiazolo[4,5-g]quinolin-2-yl)-4,5-dihydro-thiazole-4-carboxylic acid] (21)

D-cysteine (5 mg, 0.028 mmol) was dissolved in 1 mL of 0.1M aqueous sodium phosphate buffer, pH 8 and degassed under argon. This solution was added to 20 (6 mg, 0.023 mmol) in 1 mL of degassed methanol. The reaction was stirred for 1 h, and then diluted with sodium phosphate buffer (2 mL) and washed with ethyl acetate (2×5 mL). The aqueous phase was acidified to pH 4 with 1M HCl and extracted with ethyl acetate (2×5 mL). The solvent was removed by rotary evaporation to yield 21 (3.2 mg, 38%). $^1$H-NMR (400 MHz, $CDCl_3$): δ 7.80 (s, 1H), 6.83 (s, 1H), 5.48 (d, 1H, J=1.2 Hz), 5.40 (t, 1H, J=12.0 Hz), 3.76 (d, 2H, J=12.0 Hz), 2.06 (d, 1H, J=4.0 Hz), 1.34 (d, 1H, J=1.2 Hz). $^{13}$C-NMR (100 MHz, $CDCl_3$): 172.0, 167.6, 154.2, 146.9, 137.7, 130.4, 127.9, 123.2, 119.7, 102.5, 77.9, 53.1, 34.9, 31.6, 19.0. HRMS (ESI+) Calcd for $C_{17}H_{18}N_3O_2S_2$: 360.0840. Found: 360.0812.

2-Chloro-5,6,6,8-tetramethyl-5,6-dihydro-thiazolo[4,5-g]quinoline (22)

$CH_3I$ (80 mg, 0.56 mmol) was added to a mixture of 19 (100 mg, 0.37 mmol) and $K_2CO_3$ (153 mg, 1.11 mmol) in DMF (5 mL). The reaction mixture was heated to 65° C. and stirred overnight. The reaction was then cooled to room temperature, poured into water and extracted with ethyl acetate (2×50 mL). The organic phase was evaporated under vacuum to yield 22 (60 mg, 58%). ¹H-NMR (400 MHz, CDCl₃): δ 7.56 (s, 1H), 6.75 (s, 1H), 5.43 (d, 1H, J=1.2 Hz), 2.83 (s, 1H), 2.03 (d, 3H, J=1.2 Hz), 1.33 (s, 1H). ¹³C-NMR (100 MHz, CDCl₃): 147.4, 144.5, 142.9, 137.5, 132.0, 127.9, 124.1, 117.0, 100.8, 56.9, 31.5, 27.6, 18.9.

5,6,6,8-Tetramethyl-5,6-dihydro-thiazolo[4,5-g]quinoline-2-carbonitrile (23)

Potassium cyanide (29 mg, 0.45 mmol) was added to a solution of 22 (60 mg, 0.22 mmol) in DMSO (5 mL) and stirred for 3 h at 130° C. The reaction was cooled to room temperature, poured into water, and extracted with ethyl acetate (2×20 mL). The organic phase was evaporated to dryness and the crude material purified by flash chromatography using 10% ethyl acetate: hexane as eluent (30 mg, 50%). ¹H-NMR (400 MHz, CDCl₃): δ 7.72 (s, 1H), 6.79 (s, 1H), 5.49 (s, 1H), 2.89 (s, 3H), 2.06 (d, 3H, J=1.2 Hz), 1.39 (s, 6H). ¹³C-NMR (100 MHz, CDCl₃): δ 146.7, 144.5, 138.4, 132.7, 129.3, 127.3, 125.5, 118.7, 114.4, 99.2, 57.7, 31.8, 28.5, 19.0. HRMS (ESI⁺) Calcd for $C_{15}H_{16}N_3S$: 270.1065. Found: 270.1068.

CycLuc6 [2-(5,6,6,8-Tetramethyl-5,6-dihydro-thiazolo[4,5-g]quinolin-2-yl)-4,5-dihydro-thiazole-4-carboxylic acid] (24)

D-cysteine (3.1 mg, 0.017 mmol) was dissolved in 1 mL of 0.1M aqueous sodium phosphate buffer, pH 8 and degassed under argon. This solution was added to 23 (4 mg, 0.014 mmol) in 1 mL of degassed methanol. The reaction was stirred for 1 h, and then diluted with sodium phosphate buffer (2 mL) and washed with ethyl acetate (2×5 mL). The aqueous phase was acidified to pH 4 with 1M HCl and extracted with ethyl acetate (2×5 mL). The solvent was removed by rotary evaporation to afford 24 (2.5 mg, 47%). ¹H-NMR (400 MHz, CDCl₃): δ 7.75 (s, 1H), 6.83 (s, 1H), 5.45 (s, 1H), 5.40 (t, 1H, J=12.0 Hz), 3.78-3.74 (m, 2H), 2.90 (s, 3H), 2.05 (s, 3H), 1.38 (s, 6H). ¹³C-NMR (100 MHz, CDCl₃): δ 172.8, 167.9, 153.7, 145.9, 145.5, 138.7, 132.0, 127.7, 124.6, 118.7, 100.2, 78.28, 57.4, 35.0, 31.7, 28.34, 28.3, 19.1. HRMS (ESI⁺) Calcd for $C_{18}H_{20}N_3O_2S_2$: 374.0997. Found: 374.1011.

Example 6

Exemplary Synthetic Schemes for CycLuc7, CycLuc8, CycLuc7', and CycLuc8'

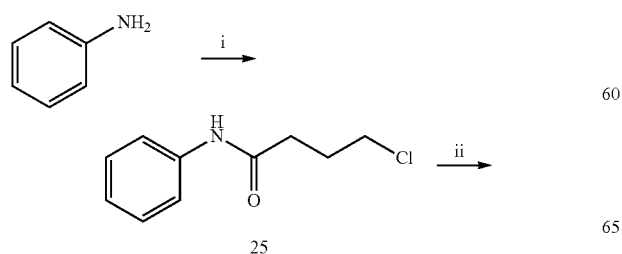

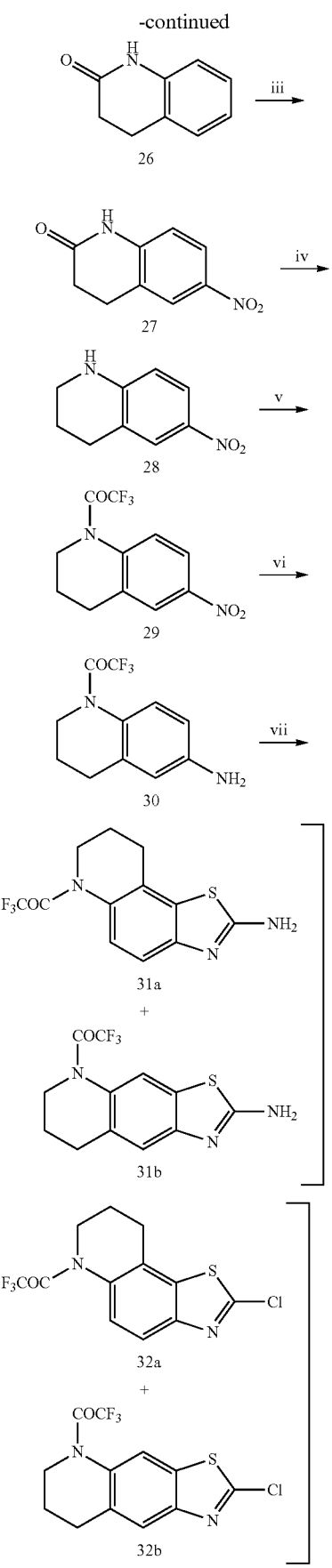

-continued

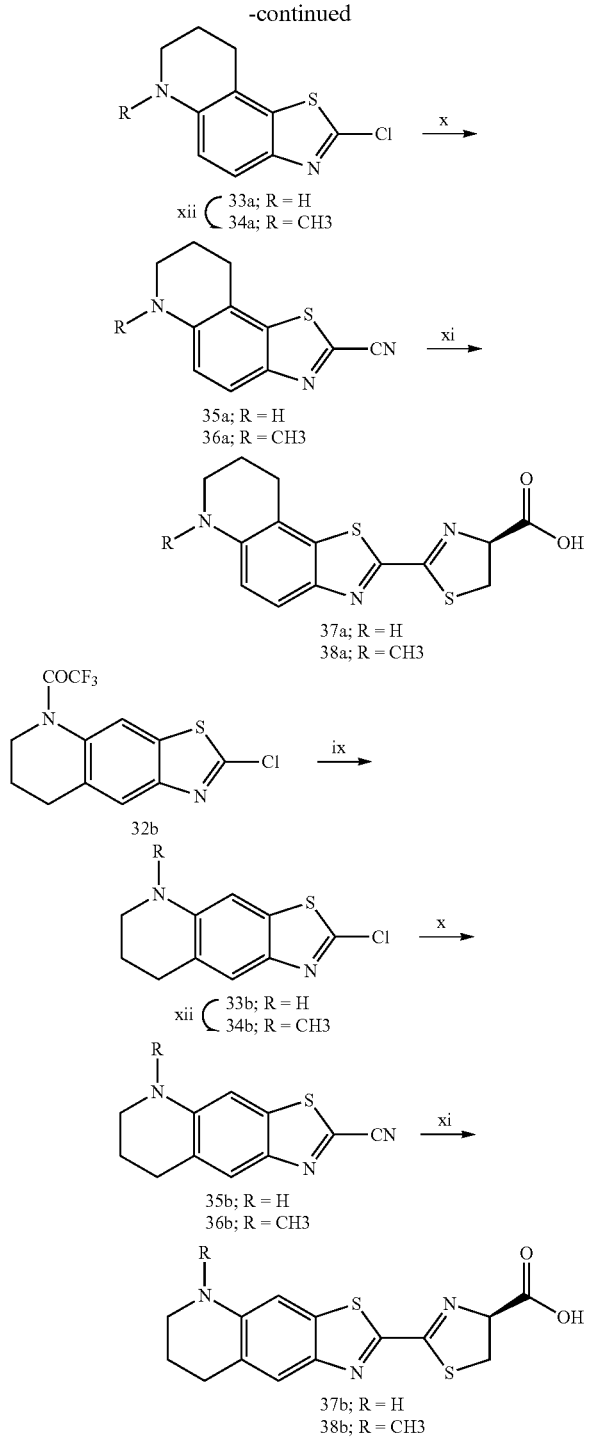

i) 3-Chloropropionyl Chloride, pyridine, acetone, 2h, 55° C.; ii) AlCl₃ 120° C.; iii) HNO₃, H₂SO₄; iv) BH₃.THF (1M in THF), THF; v) TFAA, TEA, CH₂Cl₂; vi) SnCl₂-2H₂O, DMF; vii) KSCN, Br₂, AcOH; viii) t-Butyl nitrite, CuCl, CH₃CN, rt for 2h and 65° C. for 1h; ix) NaBH₄, CH₃OH; x) KCN, DMSO, 130° C.; xi) D-cysteine, aq. CH₃OH, pH 8; xii) NaBH(OAc)₃, HCHO, DCE 4-Chloro-N-phenyl-butyramide (25)

3-chloropropionyl chloride (16.24 g, 129 mmol) was added to a mixture of aniline (10 g, 107.4 mmol) and pyridine (21.20 g, 268.4 mmol) in acetone and the reaction mixture was heated for 2 h at 55° C. After cooling to room temperature, the mixture was poured into water and extracted with ethyl acetate. The organic layer was washed with 1N HCl, water and brine and the solvent was removed by rotary evaporation to give 25 (20 g, 94.5%). ¹H-NMR (400 MHz, CDCl₃): δ 7.84 (s, 1H), 7.51 (d, 2H, J=7.2 Hz), 7.31 (t, 2H, J=7.2 Hz), 7.12 (t, 1H, J=7.2 Hz), 3.85 (t, 2H, J=6.4 Hz), 2.80 (t, 2H, J=6.4 Hz). ¹³C-NMR (100 MHz, CDCl₃): δ 168.4, 137.7, 129.3, 124.9, 120.5, 40.5, 40.2. HRMS (ESI⁺) Calcd for C₉H₁₁ClNO: 184.0529. Found: 184.0518.

3,4-Dihydro-1H-quinolin-2-one (26)

4-Chloro-N-phenyl-butyramide 25 (10 g, 54.6 mmol) and AlCl₃ (29 g, 218.4 mmol) was heated at 120° C. for 2 h, followed by cooling to room temperature. Crushed ice was added to the reaction mixture and the solid was vacuum filtered. The compound was purified by flash chromatography using 30% ethyl acetate: hexane as eluent (5.8 g, 72.2%). ¹H-NMR (400 MHz, CDCl₃): δ 9.03 (s, 1H), 7.19-7.15 (m, 2H), 6.98 (t, 1H, J=8.0 Hz), 6.83 (d, 1H, J=8.0 Hz), 2.976 (t, 2H, J=7.6 Hz), 2.646 (t, 2H, J=7.6 Hz). ¹³C-NMR (100 MHz, CDCl₃): δ 172.2, 137.4, 128.2, 127.8, 123.9, 123.3, 115.7, 30.9, 25.6. HRMS (ESI⁺) Calcd for C₉H₁₀NO: 148.0762. Found: 148.0739.

6-Nitro-3,4-dihydro-1H-quinolin-2-one (27)

HNO₃ (1.5 mL, 34.01 mmol) was added dropwise to a solution of sulfuric acid (10 mL) and 26 (5 g, 34.01 mmol) at 0° C. The reaction mixture then stirred for 1 h at 0° C. The solution poured over crushed ice and the resulting precipitate was vacuum filtered and purified by flash chromatography using 5% methanol: dichloromethane to give a yellow solid 27 (2 g, 30.6%). ¹H-NMR (400 MHz, CDCl₃): δ 9.40 (s, 1H), 8.12-8.09 (m, 2H), 6.93 (d, 1H, J=9.2 Hz), 3.10 (t, 2H, J=7.2 Hz), 2.73 (t, 2H, J=7.6 Hz). ¹³C-NMR (100 MHz, CDCl₃): δ 172.1, 143.4, 143.1, 124.3, 124.2, 124.1, 115.7, 30.2, 25.3. HRMS (ESI⁺) Calcd for C₉H₈N₂O₃Na: 215.0433. Found: 215.0417.

6-Nitro-1,2,3,4-tetrahydro-quinoline (28)

A solution of 27 (1.5 g, 7.8 mmol) in THF (10 mL) was treated with 1M BH₃/THF (46.8 mL). The solution was refluxed for 30 min then cooled to 0° C. and quenched with 1N HCl (20 mL). The solution was stirred for 30 min then concentrated and extracted with ethyl acetate (2×100 mL). The organic layer was evaporated and purified by flash chromatography using 20% ethyl acetate: hexane as eluent to yield 28 (0.8 g, 57.6%). ¹H-NMR (400 MHz, CDCl₃): δ 7.90-7.87 (m, 2H), 6.36 (d, 1H, J=9.2 Hz), 4.69 (s, 1H), 3.43-3.40 (m, 2H), 2.80 (t, 2H, J=6.8 Hz), 1.98-1.92 (m, 2H). ¹³C-NMR (100 MHz, CDCl₃): δ 150.6, 126.1, 124.5, 120.0, 112.4, 41.9, 27.1, 21.0. HRMS (ESI⁺) Calcd for C₉H₁₁N₂O₂: 179.0820. Found: 179.0824.

2,2,2-Trifluoro-1-(6-nitro-3,4-dihydro-2H-quinolin-1-yl)-ethanone (29)

6-Nitro-1,2,3,4-tetrahydro-quinoline 5 (0.5 g, 2.3 mmol) and triethylamine (0.3 mL, 2.6 mmol) were stirred in dichloromethane (10 mL) as trifluoroacetic anhydride (550 mg, 2.6 mmol) was added dropwise. This mixture was stirred for 45 min, then water (50 mL) was added. After stirring for 10 min, the mixture was acidified with 5M HCl. The organic layer was washed with brine, dried and evaporated to give 29 as a yellow solid (0.63 g, 98.5%). $^1$H-NMR (400 MHz, CDCl$_3$): δ 8.09-8.06 (m, 2H), 7.91-7.88 (m, 1H), 3.89 (t, 2H, J=6.8 Hz), 3.00 (t, 2H, J=6.4 Hz), 2.18-2.11 (m, 2H). $^{13}$C-NMR (100 MHz, CDCl$_3$): δ 156.4 (q, $^2J_{CF}$=37 Hz), 145.3, 142.5, 132.5, 125.4, 124.8, 121.7, 116.5 (q, $^1J_{CF}$=286 Hz), 45.4 (q, $^4J_{CF}$=4 Hz), 26.6, 23.1. $^{19}$F-NMR (376 MHz, CDCl$_3$): δ −68.9. HRMS (ESI$^+$) Calcd for C$_{11}$H$_9$F$_3$N$_2$O$_3$Na: 297.0463. Found: 297.0475.

1-(6-Amino-3,4-dihydro-2H-quinan-1-yl)-2,2,2-trifluoro-ethanone (30)

SnCl$_2$.2H$_2$O (1.47 g, 6.56 mmol) was added to a solution 29 (0.6 g, 2.18 mmol) in ethanol (15 mL) and the reaction mixture was heated to reflux for 4 h. After cooling to room temperature the solvent was evaporated under vacuum. The resulting residue was dissolved in NaHCO$_3$ (20 mL) and extracted with ethyl acetate (2×50 mL). The organic layer was evaporated under vacuum to give desired product and used for next step without further purification (450 mg, 84.5%). HRMS (ESI$^+$) Calcd for C$_{11}$H$_{12}$F$_3$N$_2$O: 245.0902. Found: 245.0870.

1-(2-Amino-8,9-dihydro-7H-thiazolo[5,4-f]quinolin-6-yl)-2,2,2-trifluoro-ethanone (31a/b)

A solution of 30 (400 mg, 1.62 mmol) and potassium thiocyanate (636 mg, 6.55 mmol) in AcOH (10 mL) was stirred at 20° C. for 10 min. Then bromine (256 mg, 1.62 mmol) was added over 20 min dropwise. The reaction mixture was stirred further at room temperature for 21 h. On completion of the reaction following a TLC examination, the reaction mixture was poured over crushed ice the pH was adjusted to 8 using NH$_4$OH. The resulting precipitate was vacuum-filtered and dried to give title compound and used for next step without further purification (440 mg, 90.2%). FIRMS (ESI$^+$) Calcd for C$_{12}$H$_{11}$F$_3$N$_3$OS: 302.0575. Found: 302.0555.

1-(2-Chloro-8,9-dihydro-7H-thiazolo[5,4-f]quinolin-6-yl)-2,2,2-trifluoro-ethanone (32a/b)

To a mixture of t-butyl nitrite (205 mg, 1.99 mmol), cupric chloride (157.6 mg, 1.59 mmol) and acetonitrile (10 mL) was added 31a/b (400 mg, 1.328 mmol) in portions over 1 h. The reaction mixture was stirred at room temperature for 2 h heated to 65° C. for 1 h. The mixture was filtered and the filtrate was poured into 6N HCl and extracted with ethyl acetate (2×20 mL). After concentration the crude product (310 mg, 73%) was purified by flash chromatography (6% ethyl acetate: hexane) to yield two isomers (220 mg of 32a and 25 mg of 32b). 32a: $^1$H-NMR (400 MHz, CDCl$_3$): δ 7.85-7.78 (m, 2H), 3.91 (t, 2H, J=5.6 Hz), 2.94 (t, 2H, J=6.8 Hz), 2.26-2.20 (m, 2H). $^{13}$C-NMR (100 MHz, CDCl$_3$): δ 156.1 (q, $^2J_{CF}$=35 Hz), 153.1, 148.9, 136.6, 134.9, 123.9, 120.5, 116.8 (q, $^1J_{CF}$=286 Hz), 45.6 (q, $^4J_{CF}$=3 Hz), 26.1, 23.4. $^{19}$F-NMR (376 MHz, CDCl$_3$) δ −69.2. HRMS (ESI$^+$) Calcd for C$_{12}$H$_9$F$_3$N$_2$OS: 321.0076. Found: 321.0084. 32b: $^1$H-NMR (400 MHz, CDCl$_3$): δ 8.24 (s, 1H), 7.74 (s, 1H), 3.90-3.87 (m, 2H), 3.01 (s, 2H), 2.16-2.11 (m, 2H). $^{13}$C-NMR (100 MHz, CDCl$_3$): δ 154.5, 149.4, 135.1, 134.1, 130.7, 122.6, 117.3, 116.8 (q, $^1J_{CF}$=286 Hz), 112.5, 45.4, 26.6, 23.5. $^{19}$F-NMR (376 MHz, CDCl$_3$): δ −69.1. HRMS (ESI$^+$) Calcd for C$_{12}$H$_9$F$_3$N$_2$OS: 321.0076. Found: 321.0085.

2-Chloro-6,7,8,9-tetrahydro-thiazolo[5,4-f]quinoline (33a)

The trifluoroacetamide 32a (150 mg, 0.468 mmol) was stirred in methanol (5 mL) as NaBH$_4$ (69.3 mg, 1.875 mmol) was added in portions over five minutes. The mixture was stirred for 15 min, diluted with water (10 ml) and extracted with ethyl acetate (2×20 mL). The organic layer was washed with brine and evaporated to give 33a (90 mg, 87.3%). $^1$H-NMR (400 MHz, CDCl$_3$): δ 7.47 (d, 1H, J=8.8 Hz), 6.57 (d, 1H, J=8.4 Hz), 4.06 (s, 1H), 3.29 (t, 2H, J=5.6 Hz), 2.67 (t, 2H, J=6.0 Hz), 2.01-1.95 (m, 2H). $^{13}$C-NMR (100 MHz, CDCl$_3$): δ 147.0, 143.0, 142.7, 137.9, 121.0, 115.1, 112.6, 41.8, 26.4, 21.8. HRMS (ESI$^+$) Calcd for C$_{10}$H$_{10}$ClN$_2$S: 225.0253. Found: 225.0259.

6,7,8,9-Tetrahydro-thiazolo[5,4-f]quinoline-2-carbonitrile (35a)

Potassium cyanide (46.42 mg, 0.714 mmol) was added to a solution of 33a (80 mg, 0.357 mmol) in DMSO (5 mL) stirred for 3 h at 130° C. The reaction cooled to room temperature and poured into water and extracted with ethyl acetate (2×20 mL) the organic phase was evaporated to dryness and purified by flash chromatography using 10% ethyl acetate: hexane as eluent (30 mg, 39.1%). $^1$H-NMR (400 MHz, CDCl$_3$): δ 7.77 (d, 1H, J=8.4 Hz), 6.76 (d, 1H, J=8.4 Hz), 4.36 (s, 1H), 3.43-3.40 (m, 2H), 2.80 (t, 2H, J=6.8 Hz), 2.11-2.05 (m, 2H). $^{13}$C-NMR (100 MHz, CDCl$_3$): δ 145.1, 144.4, 138.5, 129.4, 123.7, 117.3, 114.3, 111.2, 41.7, 26.5, 21.3. HRMS (ESI$^+$) Calcd for C$_{11}$H$_{10}$N$_3$S: 215.0595. Found: 215.0585.

CycLuc7' [2-(6,7,8,9-Tetrahydro-thiazolo[5,4-f]quinolin-2-yl)-4,5-dihydro-thiazole-4-carboxylic acid] (37a)

D-cysteine (4.8 mg, 0.027 mmol) was dissolved in 1 mL of 0.1M aqueous sodium phosphate buffer, pH 8 and degassed under argon. This solution was added to 35a (5 mg, 0.023 mmol) in 1 mL of degassed methanol. The reaction was stirred for 1 h, and then diluted with sodium phosphate buffer (2 mL) and washed with ethyl acetate (2×10 mL). The aqueous phase was acidified to pH 4 with 1M HCl and extracted with ethyl acetate (2×5 mL). The solvent was removed by rotary evaporation to get yield 37a (4 mg, 54%). $^1$H-NMR (400 MHz, CDCl$_3$+1 drop CD$_3$OD): δ 7.68 (d, 1H, J=8.8 Hz), 6.67 (d, 1H, J=8.8 Hz), 5.30 (t, 1H, J=10 Hz), 3.75-3.64 (m, 2H), 3.33 (t, 2H, J=5.6 Hz), 2.76 (t, 2H, J=6.4 Hz), 2.06-1.99 (m, 2H). $^{13}$C-NMR (100 MHz, CDCl$_3$+1 drop CD$_3$OD): δ 172.4, 166.8, 154.7, 145.4, 143.9, 138.5, 123.0, 116.3, 112.2, 78.2, 41.6, 35.3, 26.2, 21.5. HRMS (ESI$^+$) Calcd for C$_{14}$H$_{14}$N$_3$O$_2$S$_2$: 320.0527. Found: 320.0491.

2-Chloro-6-methyl-6,7,8,9-tetrahydro-thiazolo[5,4-f]quinoline (34a)

To 33a (50 mg, 0.22 mmol) and 37% formaldehyde (26.7 mg, 0.89 mmol) in 1,2-dichloroethane (5 mL) was added sodium triacetoxyborohydride (70 mg, 0.33 mmol) and the reaction mixture was stirred for 1 h at ambient temperature. The reaction was quenched with 1N NaOH (5 mL). The product was extracted with ethyl acetate (2×20 mL), washed with brine and dried over sodium sulfate. The solvent was removed by rotary evaporation and the resulting solid was purified by flash chromatography using 5% ethyl acetate:

hexane as eluent (40 mg, 76%). ¹H-NMR (400 MHz, CDCl₃): δ 7.62 (d, 1H, J=9.2 Hz), 6.80 (d, 1H, J=8.4 Hz), 3.27 (t, 2H, J=5.6 Hz), 2.96 (s, 3H), 2.75 (t, 2H, J=6.4 Hz), 2.13-2.07 (m, 2H). ¹³C-NMR (100 MHz, CDCl₃): δ 147.4, 144.9, 142.4, 137.7, 121.1, 113.9, 111.9, 51.4, 40.0, 27.4, 22.1. HRMS (ESI⁺) Calcd for $C_{11}H_{12}ClN_2S$: 239.0410. Found: 239.0380.

6-Methyl-6,7,8,9-tetrahydro-thiazolo[5,4-f]quinoline-2-carbonitrile (36a)

Potassium cyanide (16 mg, 0.25 mmol) was added to a solution of 34a (30 mg, 0.12 mmol) in DMSO (5 mL), then stirred for 3 h at 130° C. The reaction was cooled to room temperature, then poured into water and extracted with ethyl acetate (2×20 mL). The organic phase was evaporated to dryness and purified by flash chromatography using 10% ethyl acetate: hexane as eluent (10 mg, 36%). ¹H-NMR (400 MHz, CDCl₃): δ 7.86 (d, 1H, J=8.8 Hz), 6.96 (d, 1H, J=9.2 Hz), 3.37 (t, 2H, J=6 Hz), 3.04 (s, 3H), 2.80 (t, 2H, J=6.4 Hz), 2.15-2.09 (m, 2H). ¹³C-NMR (100 MHz, CDCl₃): δ 146.7, 143.8, 138.0, 129.6, 123.8, 114.4, 113.9, 112.5, 51.2, 39.8, 27.4, 21.6. HRMS (ESI⁺) Calcd for $C_{12}H_{12}N_3S$: 230.0752. Found: 230.0742.

CycLuc8' [2-(6-Methyl-6,7,8,9-tetrahydro-thiazolo[5,4-f]quinolin-2-yl)-4,5-dihydro-thiazole-4-carboxylic acid] (38a)

D-cysteine (2.8 mg, 0.015 mmol) was dissolved in 1 mL of 0.1M aqueous sodium phosphate buffer, pH 8 and degassed under argon. This solution was added to 36a (3 mg, 0.013 mmol) in 1 mL of degassed methanol. The reaction was stirred for 1 h, and then diluted with sodium phosphate buffer and washed with ethyl acetate (2×5 mL). The aqueous phase was acidified to pH 4 with 1M HCl and extracted with ethyl acetate (2×5 mL). The solvent was removed by rotary evaporation to yield 38a as an orange red solid (2 mg, 46%). ¹H-NMR (400 MHz, CDCl₃): δ 7.79 (d, 1H, J=8.8 Hz), 6.89 (d, 1H, J=9.6), 5.30 (t, 1H, J=9.6 Hz), 3.76-3.63 (m, 2H), 3.31-3.28 (m, 2H), 2.98 (s, 3H), 2.78 (t, 2H, J=6.8 Hz), 2.11-2.05 (m, 2H). ¹³C-NMR (100 MHz, CDCl₃+1 drop CD₃OD): δ 172.4, 166.9, 154.9, 153.7, 145.6, 145.0, 138.1, 123.1, 113.3, 78.2, 51.3, 40.1, 35.3, 27.1, 21.6. HRMS (ESI⁺) Calcd for $C_{15}H_{16}N_3O_2S_2$: 334.0684. Found: 348.0855.

2-Chloro-5,6,7,8-tetrahydro-thiazolo[4,5-g]quinoline (33 b)

Compound 32b (25 mg, 0.07 mmol) was stirred in methanol (5 mL) as NaBH₄ (11 mg, 0.31 mmol) was added in portions over five minutes. The mixture was stirred for 15 min, diluted with water (10 mL) and extracted with ethyl acetate (2×20 mL). The organic layer was washed with brine and evaporated to give 33b (15 mg, 85%). ¹H-NMR (400 MHz, CDCl₃): δ 7.47 (s, 1H), 6.73 (s, 1H), 4.13 (br s, 1H), 3.36 (t, 2H, J=5.6 Hz), 2.89 (t, 2H, J=6.0 Hz), 1.99-1.93 (m, 2H). ¹³C-NMR (100 MHz, CDCl₃): δ 147.3, 143.9, 143.2, 135.6, 123.0, 122.3, 103.5, 42.2, 27.7, 21.9. HRMS (ESI⁺) Calcd for $C_{10}H_{10}ClN_2S$: 225.0253. Found: 225.0243.

5,6,7,8-Tetrahydro-thiazolo[4,5-g]quinoline-2-carbonitrile (35b)

Potassium cyanide (8.7 mg, 0.13 mmol) was added to a solution of 33b (15 mg, 0.06 mmol) in DMSO (2 mL), then stirred for 3 h at 130° C. The reaction was cooled to room temperature, then poured into water and extracted with ethyl acetate (2×20 mL). The organic phase was evaporated to dryness and purified by flash chromatography using 10% ethyl acetate: hexane as eluent (8 mg, 56%). ¹H-NMR (400 MHz, CDCl₃): δ 7.70 (s, 1H), 6.79 (s, 1H), 4.48 (s, 1H), 3.42 (t, 2H, J=6 Hz), 2.93 (t, 2H, J=6 Hz), 2.01-1.95 (m, 2H). ¹³C-NMR (100 MHz, CDCl₃): δ 146.6, 144.8, 129.2, 125.0, 124.5, 119.9, 114.3, 101.9, 42.1, 27.9, 21.4. HRMS (ESI⁺) Calcd for $C_{11}H_{10}N_3S$: 216.0595. Found: 216.0594.

CycLuc7 [2-(5,6,7,8-Tetrahydro-thiazolo[4,5-g]quinolin-2-yl)-4,5-dihydro-thiazole-4-carboxylic acid] (37b)

D-cysteine (4.8 mg, 0.027 mmol) was dissolved in 1 mL of 0.1M aqueous sodium phosphate buffer, pH 8 and degassed under argon. This solution was added to 35b (5 mg, 0.023 mmol) in 1 mL of degassed methanol. The reaction was stirred for 1 h, and then diluted with sodium phosphate buffer and washed with ethyl acetate (2×10 mL). The aqueous phase was acidified to pH 4 with 1M HCl and extracted with ethyl acetate (2×10 mL). The solvent was removed by rotary evaporation to yield 37b as an orange red solid (3.5 mg, 47%). ¹H-NMR (400 MHz, CDCl₃+1 drop CD₃OD): δ 7.64 (s, 1H), 6.84 (s, 1H), 5.28 (t, 1H, J=8.4 Hz), 3.74-3.63 (m, 2H), 3.34 (t, 2H, J=6.0 Hz), 2.88 (t, 2H, J=6.0 Hz), 1.97-1.91 (m, 2H). ¹³C-NMR (100 MHz, CDCl3+1 drop CD₃OD): δ 172.3, 166.9, 154.6, 145.9, 144.8, 136.3, 124.5, 123.6, 103.6, 78.1, 42.0, 35.2, 27.7, 21.5. HRMS (ESI⁺) Calcd for $C_{14}H_{14}N_3O_2S_2$: 320.0527. Found: 320.0537.

2-Chloro-5-methyl-5,6,7,8-tetrahydro-thiazolo[4,5-g]quinoline (34b)

2-Chloro-5,6,7,8-tetrahydro-thiazolo[4,5-g]quinoline 33b (30 mg, 0.13 mmol) and 37% formaldehyde (16 mg, 0.53 mmol) were dissolved in 1,2-dichloroethane (3 mL). Sodium triacetoxyborohydride (41.3 mg, 0.19 mmol) was added and the reaction mixture was stirred for 1 h at ambient temperature. The reaction was quenched with 1N NaOH (5 mL). The product was extracted with ethyl acetate (2×20 mL), washed with brine and dried over sodium sulfate. The solvent was removed by rotary evaporation and the resulting solid was purified by flash chromatography using 5% ethyl acetate: hexane as eluent (15 mg, 48%). ¹H-NMR (400 MHz, CDCl₃): δ 7.46 (s, 1H), 6.78 (s, 1H), 3.30 (t, 2H, J=5.6 Hz), 2.93 (s, 3H), 2.86 (t, 2H, J=6.4 Hz), 2.02-1.96 (m, 2H). ¹³C-NMR (100 MHz, CDCl₃): δ 146.9, 145.7, 142.4, 136.2, 124.1, 122.0, 100.4, 51.3, 39.5, 28.5, 22.5. HRMS (ESI⁺) Calcd for $C_{11}H_{12}ClN_2S$: 239.0410. Found: 239.0390.

5-Methyl-5,6,7,8-tetrahydro-thiazolo[4,5-g]quinoline-2-carbonitrile (36b)

Potassium cyanide (7.8 mg, 0.12 mmol) was added to a solution of 34b (15 mg, 0.06 mmol) in DMSO (3 mL), then stirred for 3 h at 130° C. The reaction was cooled to room temperature, then poured into water and extracted with ethyl acetate (2×20 mL). The organic phase was evaporated to dryness and purified by flash chromatography using 10% ethyl acetate: hexane as eluent (6 mg, 43%). ¹H-NMR (400 MHz, CDCl₃): δ 7.67 (s, 1H), 6.83 (s, 1H), 3.40 (t, 2H, J=6.0 Hz), 3.00 (s, 3H), 2.91 (t, 2H, J=6.4 Hz), 2.03-1.99 (m, 2H). ¹³C-NMR (100 MHz, CDCl₃): δ 147.8, 144.0, 137.1, 128.7, 126.2, 123.7, 114.5, 98.9, 51.4, 39.4, 28.7, 22.0. HRMS (ESI$^+$) Calcd for $C_{12}H_{12}N_3S$: 230.0752. Found: 230.0762.

CycLuc8 [2-(5-Methyl-5,6,7,8-tetrahydro-thiazolo[4,5-g]quinolin-2-yl)-4,5-dihydro-thiazole-4-carboxylic acid] (38b)

D-cysteine (1.2 mg, 0.007 mmol) was dissolved in 1 mL of 0.1M aqueous sodium phosphate buffer, pH 8 and degassed under argon. This solution was added to 36b (1.5 mg, 0.006 mmol) in 1 mL of degassed methanol. The reaction was stirred for 1 h, and then diluted with sodium phosphate buffer and washed with ethyl acetate (2×5 mL). The aqueous phase was acidified to pH 4 with 1M HCl and extracted with ethyl acetate (2×5 mL). The solvent was removed by rotary evaporation to yield 38b as an orange red solid (1 mg, 50%). $^1$H-NMR (400 MHz, CDCl$_3$): δ 7.67 (s, 1H), 6.88 (s, 1H), 5.39 (t, 1H, J=9.6 Hz), 3.78-3.76 (m, 2H), 3.39 (t, 2H, J=5.6 Hz), 3.00 (s, 3H), 2.90 (t, 2H, J=6.8 Hz), 2.05-1.97 (m, 2H). $^{13}$C-NMR (100 MHz, CDCl$_3$): δ 171.7, 168.4, 152.8, 147.1, 145.1, 137.4, 125.2, 123.7, 99.8, 77.9, 51.4, 39.4, 34.8, 28.7, 22.2. HRMS (ESI$^+$) Calcd for $C_{15}H_{16}N_3O_2S_2$: 334.0684, Found: 334.0679.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A polypeptide comprising a mutant luciferase, wherein said mutant luciferase is at least 95% identical to the full length of SEQ ID NO: 5 and comprises a lysine at position 218 and an alanine at position 342, and wherein, compared to the luciferase of SEQ ID NO: 5, said mutant luciferase has improved bioluminescence using CycLuc2 as the substrate.

2. A kit comprising the polypeptide of claim 1 and a cognate substrate.

3. A method of producing bioluminescence in a sample, the method comprising:
   providing a sample comprising the polypeptide of claim 1; and
   contacting the sample with a cognate substrate.

4. The method of claim 3, further comprising detecting bioluminescence in the sample.

5. The method of claim 3, wherein the sample comprises a living cell, a living animal, a tissue or organ, or a cell or tissue extract.

6. A method of producing bioluminescence in a sample, the method comprising:
   providing a sample comprising the polypeptide of claim 1, and
   contacting the sample with a substrate, wherein
   the substrate is CycLuc1-8, MeNH-LH2, iBuNH-LH2, (3-hydroxypropyl)NH-LH2, or Me2N-LH2.

7. The method of claim 6, further comprising detecting bioluminescence in the sample.

8. The method of claim 6, further comprising obtaining an image of the bioluminescence in the sample.

9. The method of claim 6, wherein the substrate is CycLuc1, CycLuc4, CycLuc2, or CycLuc7.

10. A kit for use in a method of producing bioluminescence in a sample, the kit comprising the polypeptide of claim 1, and a substrate, wherein
    the substrate is CycLuc1-8, MeNH-LH2, iBuNH-LH2, (3-hydroxypropyl)NH-LH2, or Me2N-LH2.

11. The kit of claim 10, wherein the substrate is CycLuc1, CycLuc4, CycLuc2, or CycLuc7.

12. The mutant luciferase of claim 1, wherein the cognate substrate is CycLuc2.

13. The kit of claim 2, wherein the cognate substrate is CycLuc2.

14. The method of claim 3, wherein the cognate substrate is CycLuc2.

15. The method of claim 6, wherein the substrate is CycLuc2.

16. The kit of claim 10, wherein the substrate is CycLuc2.

* * * * *

SEQUENCE LISTING

```
<160> NUMBER OF SEQ ID NOS: 5

<210> SEQ ID NO 1
<211> LENGTH: 548
<212> TYPE: PRT
<213> ORGANISM: Luciola cruciate

<400> SEQUENCE: 1

Met Glu Asn Met Glu Asn Asp Glu Asn Ile Val Val Gly Pro Lys Pro
1               5                   10                  15

Phe Tyr Pro Ile Glu Glu Gly Ser Ala Gly Thr Gln Leu Arg Lys Tyr
            20                  25                  30

Met Glu Arg Tyr Ala Lys Leu Gly Ala Ile Ala Phe Thr Asn Ala Val
        35                  40                  45

Thr Gly Val Asp Tyr Ser Tyr Ala Glu Tyr Leu Glu Lys Ser Cys Cys
    50                  55                  60

Leu Gly Lys Ala Leu Gln Asn Tyr Gly Leu Val Val Asp Gly Arg Ile
65                  70                  75                  80

Ala Leu Cys Ser Glu Asn Cys Glu Glu Phe Phe Ile Pro Val Ile Ala
                85                  90                  95

Gly Leu Phe Ile Gly Val Gly Val Ala Pro Thr Asn Glu Ile Tyr Thr
            100                 105                 110

Leu Arg Glu Leu Val His Ser Leu Gly Ile Ser Lys Pro Thr Ile Val
        115                 120                 125

Phe Ser Ser Lys Lys Gly Leu Asp Lys Val Ile Thr Val Gln Lys Thr
    130                 135                 140

Val Thr Ile Lys Thr Ile Val Ile Leu Asp Ser Lys Val Asp Tyr
145                 150                 155                 160

Arg Gly Tyr Gln Cys Leu Asp Thr Phe Ile Lys Arg Asn Thr Pro Pro
                165                 170                 175

Gly Phe Gln Ala Ser Ser Phe Lys Thr Val Glu Val Asp Arg Lys Glu
            180                 185                 190

Gln Val Ala Leu Ile Met Asn Ser Ser Gly Ser Thr Gly Leu Pro Lys
        195                 200                 205

Gly Val Gln Leu Thr His Glu Asn Thr Val Thr Arg Phe Ser His Ala
    210                 215                 220

Arg Asp Pro Ile Tyr Gly Asn Gln Val Ser Pro Gly Thr Ala Val Leu
225                 230                 235                 240

Thr Val Val Pro Phe His His Gly Phe Gly Met Phe Thr Thr Leu Gly
                245                 250                 255
```

```
Tyr Leu Ile Cys Gly Phe Arg Val Val Met Leu Thr Lys Phe Asp Glu
            260                 265                 270

Glu Thr Phe Leu Lys Thr Leu Gln Asp Tyr Lys Cys Thr Ser Val Ile
        275                 280                 285

Leu Val Pro Thr Leu Phe Ala Ile Leu Asn Lys Ser Glu Leu Leu Asn
    290                 295                 300

Lys Tyr Asp Leu Ser Asn Leu Val Glu Ile Ala Ser Gly Gly Ala Pro
305                 310                 315                 320

Leu Ser Lys Glu Val Gly Glu Ala Val Ala Arg Arg Phe Asn Leu Pro
            325                 330                 335

Gly Val Arg Gln Gly Tyr Gly Leu Thr Glu Thr Thr Ser Ala Ile Ile
        340                 345                 350

Ile Thr Pro Glu Gly Asp Asp Lys Pro Gly Ala Ser Gly Lys Val Val
    355                 360                 365

Pro Leu Phe Lys Ala Lys Val Ile Asp Leu Asp Thr Lys Lys Ser Leu
370                 375                 380

Gly Pro Asn Arg Arg Gly Glu Val Cys Val Lys Gly Pro Met Leu Met
385                 390                 395                 400

Lys Gly Tyr Val Asn Asn Pro Glu Ala Thr Lys Glu Leu Ile Asp Glu
            405                 410                 415

Glu Gly Trp Leu His Thr Gly Asp Ile Gly Tyr Tyr Asp Glu Glu Lys
        420                 425                 430

His Phe Phe Ile Val Asp Arg Leu Lys Ser Leu Ile Lys Tyr Lys Gly
    435                 440                 445

Tyr Gln Val Pro Pro Ala Glu Leu Glu Ser Val Leu Leu Gln His Pro
    450                 455                 460

Ser Ile Phe Asp Ala Gly Val Ala Gly Val Pro Asp Pro Val Ala Gly
465                 470                 475                 480

Glu Leu Pro Gly Ala Val Val Val Leu Glu Ser Gly Lys Asn Met Thr
            485                 490                 495

Glu Lys Glu Val Met Asp Tyr Val Ala Ser Gln Val Ser Asn Ala Lys
        500                 505                 510

Arg Leu Arg Gly Gly Val Arg Phe Val Asp Glu Val Pro Lys Gly Leu
    515                 520                 525

Thr Gly Lys Ile Asp Gly Arg Ala Ile Arg Glu Ile Leu Lys Lys Pro
    530                 535                 540

Val Ala Lys Met
545

<210> SEQ ID NO 2
<211> LENGTH: 548
<212> TYPE: PRT
<213> ORGANISM: Luciola lateralis

<400> SEQUENCE: 2

Met Glu Asn Met Glu Asn Asp Glu Asn Ile Val Tyr Gly Pro Glu Pro
  1               5                  10                  15

Phe Tyr Pro Ile Glu Glu Gly Ser Ala Gly Ala Gln Leu Arg Lys Tyr
            20                  25                  30

Met Asp Arg Tyr Ala Lys Leu Gly Ala Ile Ala Phe Thr Asn Ala Leu
        35                  40                  45

Thr Gly Val Asp Tyr Thr Tyr Ala Glu Tyr Leu Glu Lys Ser Cys Cys
    50                  55                  60

Leu Gly Glu Ala Leu Lys Asn Tyr Gly Leu Val Val Asp Gly Arg Ile
```

-continued

```
                65                  70                  75                  80
        Ala Leu Cys Ser Glu Asn Cys Glu Glu Phe Phe Ile Pro Val Leu Ala
                        85                  90                  95

Gly Leu Phe Ile Gly Val Gly Val Ala Pro Thr Asn Glu Ile Tyr Thr
                       100                 105                 110

Leu Arg Glu Leu Val His Ser Leu Gly Ile Ser Lys Pro Thr Ile Val
                       115                 120                 125

Phe Ser Ser Lys Lys Gly Leu Asp Lys Val Ile Thr Val Gln Lys Thr
                       130                 135                 140

Val Thr Ala Ile Lys Thr Ile Val Ile Leu Asp Ser Lys Val Asp Tyr
        145                 150                 155                 160

Arg Gly Tyr Gln Ser Met Asp Asn Phe Ile Lys Lys Asn Thr Pro Gln
                       165                 170                 175

Gly Phe Lys Gly Ser Ser Phe Lys Thr Val Glu Val Asn Arg Lys Glu
                       180                 185                 190

Gln Val Ala Leu Ile Met Asn Ser Ser Gly Ser Thr Gly Leu Pro Lys
                       195                 200                 205

Gly Val Gln Leu Thr His Glu Asn Ala Val Thr Arg Phe Ser His Ala
                       210                 215                 220

Arg Asp Pro Ile Tyr Gly Asn Gln Val Ser Pro Gly Thr Ala Ile Leu
        225                 230                 235                 240

Thr Val Val Pro Phe His His Gly Phe Gly Met Phe Thr Thr Leu Gly
                       245                 250                 255

Tyr Leu Thr Cys Gly Phe Arg Ile Val Met Leu Thr Lys Phe Asp Glu
                       260                 265                 270

Glu Thr Phe Leu Lys Thr Leu Gln Asp Tyr Lys Cys Ser Ser Val Ile
                       275                 280                 285

Leu Val Pro Thr Leu Phe Ala Ile Leu Asn Arg Ser Glu Leu Leu Asp
                       290                 295                 300

Lys Tyr Asp Leu Ser Asn Leu Val Glu Ile Ala Ser Gly Gly Ala Pro
        305                 310                 315                 320

Leu Ser Lys Glu Ile Gly Glu Ala Val Ala Arg Arg Phe Asn Leu Pro
                       325                 330                 335

Gly Val Arg Gln Gly Tyr Gly Leu Thr Glu Thr Thr Ser Ala Ile Ile
                       340                 345                 350

Ile Thr Pro Glu Gly Asp Asp Lys Pro Gly Ala Ser Gly Lys Val Val
                       355                 360                 365

Pro Leu Phe Lys Ala Lys Val Ile Asp Leu Asp Thr Lys Lys Thr Leu
                       370                 375                 380

Gly Pro Asn Arg Arg Gly Glu Val Cys Val Lys Gly Pro Met Leu Met
        385                 390                 395                 400

Lys Gly Tyr Val Asp Asn Pro Glu Ala Thr Arg Glu Ile Ile Asp Glu
                       405                 410                 415

Glu Gly Trp Leu His Thr Gly Asp Ile Gly Tyr Tyr Asp Glu Glu Lys
                       420                 425                 430

His Phe Phe Ile Val Asp Arg Leu Lys Ser Leu Ile Lys Tyr Lys Gly
                       435                 440                 445

Tyr Gln Val Pro Pro Ala Glu Leu Glu Ser Val Leu Leu Gln His Pro
                       450                 455                 460

Asn Ile Phe Asp Ala Gly Val Ala Gly Val Pro Asp Pro Ile Ala Gly
        465                 470                 475                 480

Glu Leu Pro Gly Ala Val Val Val Leu Glu Lys Gly Lys Ser Met Thr
                       485                 490                 495
```

Glu Lys Glu Val Met Asp Tyr Val Ala Ser Gln Val Ser Asn Ala Lys
            500                 505                 510

Arg Leu Arg Gly Gly Val Arg Phe Val Asp Glu Val Pro Lys Gly Leu
        515                 520                 525

Thr Gly Lys Ile Asp Gly Lys Ala Ile Arg Glu Ile Leu Lys Lys Pro
    530                 535                 540

Val Ala Lys Met
545

<210> SEQ ID NO 3
<211> LENGTH: 548
<212> TYPE: PRT
<213> ORGANISM: Luciola mingrelica

<400> SEQUENCE: 3

Met Glu Met Glu Lys Glu Asn Val Val Tyr Gly Pro Leu Pro Phe
1               5                   10                  15

Tyr Pro Ile Glu Glu Gly Ser Ala Gly Ile Gln Leu His Lys Tyr Met
            20                  25                  30

His Gln Tyr Ala Lys Leu Gly Ala Ile Ala Phe Ser Asn Ala Leu Thr
        35                  40                  45

Gly Val Asp Ile Ser Tyr Gln Glu Tyr Phe Asp Ile Thr Cys Arg Leu
    50                  55                  60

Ala Glu Ala Met Lys Asn Phe Gly Met Lys Pro Glu Glu His Ile Ala
65                  70                  75                  80

Leu Cys Ser Glu Asn Cys Glu Glu Phe Phe Ile Pro Val Leu Ala Gly
                85                  90                  95

Leu Tyr Ile Gly Val Ala Val Ala Pro Thr Asn Glu Ile Tyr Thr Leu
            100                 105                 110

Arg Glu Leu Asn His Ser Leu Gly Ile Ala Gln Pro Thr Ile Val Phe
        115                 120                 125

Ser Ser Arg Lys Gly Leu Pro Lys Val Leu Glu Val Gln Lys Thr Val
    130                 135                 140

Thr Cys Ile Lys Lys Ile Val Ile Leu Asp Ser Lys Val Asn Phe Gly
145                 150                 155                 160

Gly His Asp Cys Met Glu Thr Phe Ile Lys Lys His Val Glu Leu Gly
                165                 170                 175

Phe Gln Pro Ser Ser Phe Val Pro Ile Asp Val Lys Asn Arg Lys Gln
            180                 185                 190

His Val Ala Leu Leu Met Asn Ser Ser Gly Ser Thr Gly Leu Pro Lys
        195                 200                 205

Gly Val Arg Ile Thr His Glu Gly Ala Val Thr Arg Phe Ser His Ala
    210                 215                 220

Lys Asp Pro Ile Tyr Gly Asn Gln Val Ser Pro Gly Thr Ala Ile Leu
225                 230                 235                 240

Thr Val Val Pro Phe His His Gly Phe Gly Met Phe Thr Thr Leu Gly
                245                 250                 255

Tyr Phe Ala Cys Gly Tyr Arg Val Val Met Leu Thr Lys Phe Asp Glu
            260                 265                 270

Glu Leu Phe Leu Arg Thr Leu Gln Asp Tyr Lys Cys Thr Ser Val Ile
        275                 280                 285

Leu Val Pro Thr Leu Phe Ala Ile Leu Asn Lys Ser Glu Leu Ile Asp
    290                 295                 300

Lys Phe Asp Leu Ser Asn Leu Thr Glu Ile Ala Ser Gly Gly Ala Pro

```
            305                 310                 315                 320
Leu Ala Lys Glu Val Gly Glu Ala Val Ala Arg Arg Phe Asn Leu Pro
                325                 330                 335
Gly Val Arg Gln Gly Tyr Gly Leu Thr Glu Thr Thr Ser Ala Phe Ile
                340                 345                 350
Ile Thr Pro Glu Gly Asp Asp Lys Pro Gly Ala Ser Gly Lys Val Val
                355                 360                 365
Pro Leu Phe Lys Val Lys Val Ile Asp Leu Asp Thr Lys Lys Thr Leu
        370                 375                 380
Gly Val Asn Arg Arg Gly Glu Ile Cys Val Lys Gly Pro Ser Leu Met
385                 390                 395                 400
Leu Gly Tyr Ser Asn Asn Pro Glu Ala Thr Arg Glu Thr Ile Asp Glu
                405                 410                 415
Glu Gly Trp Leu His Thr Gly Asp Ile Gly Tyr Tyr Asp Glu Asp Glu
            420                 425                 430
His Phe Phe Ile Val Asp Arg Leu Lys Ser Leu Ile Lys Tyr Lys Gly
            435                 440                 445
Tyr Gln Val Pro Pro Ala Glu Leu Glu Ser Val Leu Leu Gln His Pro
        450                 455                 460
Asn Ile Phe Asp Ala Gly Val Ala Gly Val Pro Asp Pro Asp Ala Gly
465                 470                 475                 480
Glu Leu Pro Gly Ala Val Val Val Met Glu Lys Gly Lys Thr Met Thr
                485                 490                 495
Glu Lys Glu Ile Val Asp Tyr Val Asn Ser Gln Val Val Asn His Lys
                500                 505                 510
Arg Leu Arg Gly Gly Val Arg Phe Val Asp Glu Val Pro Lys Gly Leu
            515                 520                 525
Thr Gly Lys Ile Asp Ala Lys Val Ile Arg Glu Ile Leu Lys Lys Pro
        530                 535                 540
Gln Ala Lys Met
545

<210> SEQ ID NO 4
<211> LENGTH: 545
<212> TYPE: PRT
<213> ORGANISM: Photuris pennsylvanica

<400> SEQUENCE: 4

Met Glu Asp Lys Asn Ile Leu Tyr Gly Pro Glu Pro Phe His Pro Leu
 1               5                  10                  15
Ala Asp Gly Thr Ala Gly Glu Gln Met Phe Tyr Ala Leu Ser Arg Tyr
                20                  25                  30
Ala Asp Ile Ser Gly Cys Ile Ala Leu Thr Asn Ala His Thr Lys Glu
            35                  40                  45
Asn Val Leu Tyr Glu Glu Phe Leu Lys Leu Ser Cys Arg Leu Ala Glu
        50                  55                  60
Ser Phe Lys Lys Tyr Gly Leu Lys Gln Asn Asp Thr Ile Ala Val Cys
65                  70                  75                  80
Ser Glu Asn Gly Leu Gln Phe Phe Leu Pro Leu Ile Ala Ser Leu Tyr
                85                  90                  95
Leu Gly Ile Ile Ala Ala Pro Val Ser Asp Lys Tyr Ile Glu Arg Glu
                100                 105                 110
Leu Ile His Ser Leu Gly Ile Val Lys Pro Arg Ile Ile Phe Cys Ser
            115                 120                 125
```

-continued

```
Lys Asn Thr Phe Gln Lys Val Leu Asn Val Lys Ser Lys Leu Lys Tyr
    130                 135                 140
Val Glu Thr Ile Ile Ile Leu Asp Leu Asn Glu Asp Leu Gly Gly Tyr
145                 150                 155                 160
Gln Cys Leu Asn Asn Phe Ile Ser Gln Asn Ser Asp Ile Asn Leu Asp
                165                 170                 175
Val Lys Lys Phe Lys Pro Asn Ser Phe Asn Arg Asp Asp Gln Val Ala
            180                 185                 190
Leu Val Met Phe Ser Ser Gly Thr Thr Gly Val Ser Lys Gly Val Met
        195                 200                 205
Leu Thr His Lys Asn Ile Val Ala Arg Phe Ser His Cys Lys Asp Pro
    210                 215                 220
Thr Phe Gly Asn Ala Ile Asn Pro Thr Thr Ala Ile Leu Thr Val Ile
225                 230                 235                 240
Pro Phe His His Gly Phe Gly Met Thr Thr Thr Leu Gly Tyr Phe Thr
                245                 250                 255
Cys Gly Phe Arg Val Ala Leu Met His Thr Phe Glu Glu Lys Leu Phe
            260                 265                 270
Leu Gln Ser Leu Gln Asp Tyr Lys Val Glu Ser Thr Leu Leu Val Pro
        275                 280                 285
Thr Leu Met Ala Phe Phe Pro Lys Ser Ala Leu Val Glu Lys Tyr Asp
    290                 295                 300
Leu Ser His Leu Lys Glu Ile Ala Ser Gly Gly Ala Pro Leu Ser Lys
305                 310                 315                 320
Glu Ile Gly Glu Met Val Lys Lys Arg Phe Lys Leu Asn Phe Val Arg
                325                 330                 335
Gln Gly Tyr Gly Leu Thr Glu Thr Thr Ser Ala Val Leu Ile Thr Pro
            340                 345                 350
Asp Thr Asp Val Arg Pro Gly Ser Thr Gly Lys Ile Val Pro Phe His
        355                 360                 365
Ala Val Lys Val Val Asp Pro Thr Thr Gly Lys Ile Leu Gly Pro Asn
    370                 375                 380
Glu Thr Gly Glu Leu Tyr Phe Lys Gly Asp Met Ile Met Lys Ser Tyr
385                 390                 395                 400
Tyr Asn Asn Glu Glu Ala Thr Lys Ala Ile Ile Asn Lys Asp Gly Trp
                405                 410                 415
Leu Arg Ser Gly Asp Ile Ala Tyr Tyr Asp Asn Asp Gly His Phe Tyr
            420                 425                 430
Ile Val Asp Arg Leu Lys Ser Leu Ile Lys Tyr Lys Gly Tyr Gln Val
        435                 440                 445
Ala Pro Ala Glu Ile Glu Gly Ile Leu Leu Gln His Pro Tyr Ile Val
    450                 455                 460
Asp Ala Gly Val Thr Gly Ile Pro Asp Glu Ala Ala Gly Glu Leu Pro
465                 470                 475                 480
Ala Ala Gly Val Val Gln Thr Gly Lys Tyr Leu Asn Glu Gln Ile
                485                 490                 495
Val Gln Asn Phe Val Ser Ser Gln Val Ser Thr Ala Lys Trp Leu Arg
            500                 505                 510
Gly Gly Val Lys Phe Leu Asp Glu Ile Pro Lys Gly Ser Thr Gly Lys
        515                 520                 525
Ile Asp Arg Lys Val Leu Arg Gln Met Phe Glu Lys His Lys Ser Lys
    530                 535                 540
Leu
```

<210> SEQ ID NO 5
<211> LENGTH: 550
<212> TYPE: PRT
<213> ORGANISM: Photinus pyralis

<400> SEQUENCE: 5

```
Met Glu Asp Ala Lys Asn Ile Lys Lys Gly Pro Ala Pro Phe Tyr Pro
 1               5                  10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
 50                  55                  60

Glu Ala Met Lys Arg Tyr Gly Leu Asn Thr Asn His Arg Ile Val Val
 65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365
```

-continued

```
Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
                435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
                500                 505                 510

Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
    530                 535                 540

Gly Gly Lys Ser Lys Leu
545                 550
```

UNITED STATES PATENT AND TRADEMARK OFFICE
CERTIFICATE OF CORRECTION

PATENT NO. : 9,587,266 B2
APPLICATION NO. : 13/984506
DATED : March 7, 2017
INVENTOR(S) : Miller et al.

It is certified that error appears in the above-identified patent and that said Letters Patent is hereby corrected as shown below:

In the Specification

Column 1, Lines 16-19, delete:
"FEDERALLY FUNDED RESEARCH OR DEVELOPMENT
This invention was made with government support under Grant No. R21 CA127196-02 awarded by the National Institutes of Health. The government has certain rights in the invention."

And insert:
-- STATEMENT OF FEDERALLY SPONSORED RESEARCH
This invention was made with government support under Grant no. CA127196 awarded by the National Institutes of Health. The Government has certain rights in the invention. --

Signed and Sealed this
Second Day of May, 2017

Michelle K. Lee
*Director of the United States Patent and Trademark Office*